US009040058B2

(12) United States Patent
Blackkolb et al.

(10) Patent No.: US 9,040,058 B2
(45) Date of Patent: May 26, 2015

(54) FERMENTATION MEDIA FREE OF ANIMAL-DERIVED COMPONENTS FOR PRODUCTION OF DIPHTHERIA TOXOIDS SUITABLE FOR HUMAN VACCINE USE

(71) Applicant: Novartis AG, Basel (CH)

(72) Inventors: Friedrich Blackkolb, Marburg (DE); Bernd Becker, Bad Endbach (DE); Martha Reith, Rauschenberg (DE); Manfred Isenberg, Marburg (DE); Anne Katrin Hilbert, Giessen (DE)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 13/673,978

(22) Filed: Nov. 9, 2012

(65) Prior Publication Data
US 2013/0122040 A1 May 16, 2013

Related U.S. Application Data

(60) Provisional application No. 61/629,176, filed on Nov. 14, 2011.

(30) Foreign Application Priority Data

Nov. 11, 2011 (GB) .................................. 1119517.9

(51) Int. Cl.
A61K 39/05 (2006.01)
A61K 39/40 (2006.01)
A61K 39/00 (2006.01)
A61K 39/116 (2006.01)
C12N 5/00 (2006.01)
C12N 5/02 (2006.01)
C12N 1/20 (2006.01)
C07K 14/34 (2006.01)

(52) U.S. Cl.
CPC ........... C12N 1/20 (2013.01); A61K 2039/6037 (2013.01); A61K 39/05 (2013.01); C07K 14/34 (2013.01); A61K 2039/522 (2013.01); A61K 2039/55505 (2013.01)

(58) Field of Classification Search
CPC .................. A61K 2039/6037; A61K 39/0018; A61K 2039/70
See application file for complete search history.

(56) References Cited

U.S. PATENT DOCUMENTS 3,889,006 A 6/1975 Nagasawa et al.
4,624,918 A 11/1986 Hershberg
5,306,492 A 4/1994 Porro
6,013,264 A 1/2000 Petre et al.
2003/0099672 A1* 5/2003 Schultz ...................... 424/239.1
2004/0087775 A1 5/2004 Wolfe

FOREIGN PATENT DOCUMENTS

| CN | 101366945 A | 2/2009 |
|---|---|---|
| CN | 101380471 A | 3/2009 |
| EP | 0372501 A2 | 6/1990 |
| EP | 0378881 A1 | 7/1990 |
| EP | 0427347 A1 | 5/1991 |
| EP | 0471177 A2 | 2/1992 |
| EP | 0477508 A1 | 4/1992 |
| EP | 1645283 A1 | 4/2006 |
| EP | 1849860 A2 | 10/2007 |
| EP | 2228437 A1 | 9/2010 |
| GB | 314854 A | 4/1930 |
| GB | 969772 A | 9/1964 |
| KR | 20060121507 A | 11/2006 |
| WO | WO-91/01146 A1 | 2/1991 |
| WO | WO-9118926 A1 | 12/1991 |
| WO | WO-93/17712 A2 | 9/1993 |
| WO | WO-94/03208 A1 | 2/1994 |
| WO | WO-96/40242 A1 | 12/1996 |
| WO | WO-97/00697 A1 | 1/1997 |
| WO | WO-98/42721 A1 | 10/1998 |
| WO | WO-98/54296 A1 | 12/1998 |
| WO | WO-98/58668 A2 | 12/1998 |
| WO | WO-00/50449 A1 | 8/2000 |
| WO | WO-00/56360 A2 | 9/2000 |
| WO | WO-00/61761 A2 | 10/2000 |
| WO | WO-01/72337 A1 | 10/2001 |
| WO | WO-02/00249 A2 | 1/2002 |
| WO | WO-02/091998 A2 | 11/2002 |
| WO | WO-03/066094 A2 | 8/2003 |
| WO | WO-03/088946 A1 | 10/2003 |
| WO | WO-2004/041157 | 5/2004 |
| WO | WO-2005/056773 A1 | 6/2005 |

(Continued)

OTHER PUBLICATIONS

Largier, J Immunol 1957; 79:181-186.*
Bowie et al. (Science, 1990, 257:1306-1310).*
Lyng, Biologicals, 1990; 18: 11-17.*
Aggerbeck et al. (Jun. 1, 1992). "Detoxification of diphtheria and tetanus toxin with formaldehyde. Detection of protein conjugates," Biologicals 20(2):109-115.
European Examination Report mailed Jan. 22, 2013, for EP Application No. 11188902.8, 7 pages.
European Search Report and Opinion mailed Aug. 17, 2012, for EP Application No. 11188902.8, 14 pages.
Fass et al. (1995). "High-yield production of diphtheria toxin mutants by high-density culture of C7(β)tox+ strains grown in a non-deferrated medium," Appl Microbiol Biotechnol 43:83-88.

(Continued)

Primary Examiner — Gary Nickol
Assistant Examiner — Lakia Tongue
(74) Attorney, Agent, or Firm — Morrison & Foerster LLP

(57) ABSTRACT

The present invention relates to a fermentation medium for cultivating *Corynebacterium diphtheriae*. The present invention also relates to the use of the fermentation medium in processes for obtaining diphtheria toxin from the *Corynebacterium diphtheriae* bacteria being cultivated and the preparation of vaccines using the diphtheria toxin obtained in the processes. The present invention further relates to a purification and detoxification processes specifically adapted for preparing a diphtheria toxoid for inclusion into a vaccine.

23 Claims, 12 Drawing Sheets

(56) References Cited

FOREIGN PATENT DOCUMENTS

| WO | WO-2006/042542 A2 | 4/2006 |
| WO | WO-2006/113528 A2 | 10/2006 |
| WO | WO-2007/026249 A2 | 3/2007 |
| WO | WO-2007/054820 A2 | 5/2007 |
| WO | WO-2008/028956 A1 | 3/2008 |
| WO | WO-2008/028957 A2 | 3/2008 |

OTHER PUBLICATIONS

Hirai et al. (Jun. 1, 1966). "Toxin production by *Corynebacterium diphtheria* under growth-limiting conditions," Bikn Journal 9:19-31.

Paliwal et al. (1996). "Comparison of the conformation, hydrophobicity, and model membrane interactions of diphtheria toxin to those of formaldehyde-treated toxin (diphtheria toxoid): Formaldehyde stabilization of the native conformation inhibits changes that allow membrane insertion," Biochemistry 35(7):2374-2379.

United Kingdom Search Report and Examination Report mailed Mar. 9, 2012, for GB1119517.9, 7 pages.

International Search Report and Written Opinion mailed Apr. 4, 2013, for PCT/EP2012/072330 filed Nov. 9, 2012, 10 pages.

Tchorbanov et al (Oct. 2004). "Optimization of casein-based semisynthetic medium for growing of toxigenic *Corinebacterium diphtheria* in a fermenter," Canadian J Microbiol 50(10):821-826.

Tchorbanov et al. (Mar. 2004). "Molecular composition of diphtheria toxoid produced using semi-synthetic and meat extract-based broths," World J Microbiol & Biotechnol 20(2):211-217.

Bolgiano et al. (2000). "Monitoring of diphtheria pertussis and tetanus toxoids . . . " Dev Biol 103:51-59.

Cox (1975). "New method for the large-scale preparation of diphtheria toxoid: purification of toxin," Appl Microbiol 29:464-468.

Holt (1948). "The preparation of purified and concentrated diphtheria toxoid from a semi-synthetic medium," Br J Exp Pathol 29:335-346.

Isaka et al. (2004). "Recombinant cholera toxin B subunit (rCTH) as a mucosal adjuvant enhances induction of diphtheria and tetanus antitoxin antibodies . . . " Vaccine 22:3061-3068.

Metz et al. (2003). "Physiochemical and immunochemical techniques predict the quality of diphtheria toxoid vaccines," Vaccine 22:156-167.

Moghadam et al. (2008). "Application of fermentor technology in production of diphtheria toxin," Jundishapur J Microbiol 1:24-27.

United Kingdom Search Report and Examination Report mailed May 30, 2012, for GB1119517.9, 10 pages.

Arakawa et al. (2006). "Aggregation analysis of therapeutic proteins, Part 1," BioProcess Int 4(10):42-43.

Jackson et al. (2001). "Diphtheria antitoxin levels among children primed with a diphtheria and tetanus toxoids and acellular pertussis vaccine lot with a subpotent diphtheria toxoid component," J Infect Dis 183:1698-1700.

Kattan et al. (2011). "Anaphylaxis to diphtheria, tetanus, and pertussis vaccines among children with cow's milk allergy," J Allergy Clin Immunol 128(1):215-218.

Kersten et al. (1999). "Characterization of diphtheria toxoid," Pharm Pharmacol Comm 5:27-31.

Leenaars et al. (2001). "An in vitro approach in quality control of toxoid vaccines," Vaccine 19:2729-2733.

Linggood and Fenton. (1947). "The production of diphtheria toxin by submerged culture in shaking flasks," Br J Exp Pathol 28(5):354-364.

McVey et al. (2003). "A review of the effectiveness of vaccine potency control testing," Int J Parasitol 33:507-516.

Who (1990). "Requirements for diphtheria, tetanus, pertussis and combined vaccines," pp. 87-93.

Who (2000). "Adverse events following diphtheria, tetanus and pertussis vaccines," Section 4 in "Supplementary information on vaccine safety; Part 2: Background rates of adverse events following immunization", pp. 16-24.

DiMiceli et al. (2006). "Vaccination of yeast sensitive individuals: review of safety data in the US vaccine adverse event reporting system (VAERS)," Vaccine, 24(6):703-7.

Microscopy Today, Published Jan. 2000, Issue # 00-1, 32 pages, in particular, Kiernan, "Formaldehyde, Formalin, Paraformaldehyde and Glutaraldehyde: What They Are and What They Do," pp. 8-12.

Rappuoli (1997). "New and improved vaccines against diphtheria and tetanus," Chapter 31 in "New Generation Vaccines" 2nd ed., Levine et al. (eds.), Marcel Dekker, Inc., New York, pp. 417-436.

Ding et al. (2009). "Immune modulation by adjuvants combined with diphtheria toxoid administered topically in BALB/c mice after microneedle array pretreatment," Pharma Res 26(7):1635-1642.

European Office Action dated Feb. 16, 2015, for EP Application No. 11188902.8, 9 pages.

* cited by examiner

FIG. 1

```
         Yeast extract concentrate
        /          |              \
Working seed   Preculture    Fermentation medium
        \          |              /
           Preculture (fermenter)
                   |
              Fermentation
                   |
     Separation (harvest of the culture supernatant)
                   |
             Filtration cascade
                   |
   Addition of citrate buffer (final conc. 5 mM) and
   concentration (30 kDa regenerated cellulose)
                   |
   Diafiltration (5 volumes 5 mM citrate pH 6.5,
        30 kDa regenerated cellulose)
                   |
             0.2 µm filtration
                   |
     Diphtheria toxin concentrate 1 (storage)
                   |
   Buffer exchange (5 volumes 25 mM Tris-buffer
        pH 7.5, 30 kDa regenerated cellulose)
                   |
        Z carbon filtration, 0.2 µm filtration
                   |
         Diphtheria toxin concentrate 2
```

Loading scheme:

M: Marker p.I. range 4.5-6.5
1: No. 15 Ly 0.100M / FA 0.5% / pH 7.0
2: No. 7 Ly 0.025M / FA 1.0% / pH 7.0
3: No. 55 Ly 0.100M / FA 0.5% / pH 8.0
4: No. 47 Ly 0.025M / FA 1.0% / pH 8.0
5: No. 1 Ly 0.000M / FA 0.5% / pH 7.0
6: No. 41 Ly 0.000M / FA 0.5% / pH 8.0

7: Diph. Marburg production lot N° 316084
8: Diph. Marburg production lot N° 316095
9: Diph. Marburg production lot N° 316097

10: Diph. Siena production lot N° 388
11: Diph. Siena production lot N° 394
12: Diph. Siena production lot N° 395
13: Diph. Siena production lot N° 396

14: CRM197 treated with 0.7% formalin, 0.025M lysine, pH 7.4

02IE0008

1 Marker
2 (1)      Ly 0.000M / FA 0.50% / pH 7.0
3 (3)      Ly 0.025M / FA 0.50% / pH 7.0
4 (9)      Ly 0.050M / FA 0.50% / pH 7.0
5 (15)     Ly 0.100M / FA 0.50% / pH 7.0
6 (41)     Ly 0.000M / FA 0.50% / pH 8.0
7 (43)     Ly 0.025M / FA 0.50% / pH 8.0
8 (49)     Ly 0.050M / FA 0.50% / pH 8.0
9 (55)     Ly 0.100M / FA 0.50% / pH 8.0
10 Marker

02IE0009

1 Marker
2 (5)   Ly 0.025M / FA 0.75% / pH 7.0
3 (25)  Ly 0.025M / FA 0.75% / pH 7.5
4 (45)  Ly 0.025M / FA 0.75% / pH 8.0
5 (11)  Ly 0.050M / FA 0.75% / pH 7.0
6 (51)  Ly 0.050M / FA 0.75% / pH 8.0
7 (17)  Ly 0.100M / FA 0.75% / pH 7.0
8 (37)  Ly 0.100M / FA 0.75% / pH 7.5
9 (57)  Ly 0.100M / FA 0.75% / pH 8.0
10 Marker

02IE0013

1 Marker
2 (7)   Ly 0.025M / FA 1.00% / pH 7.0
3 (27)  Ly 0.025M / FA 1.00% / pH 7.5
4 (47)  Ly 0.025M / FA 1.00% / pH 8.0
5 (13)  Ly 0.050M / FA 1.00% / pH 7.0
6 (53)  Ly 0.050M / FA 1.00%  / pH 8.0
7 (19)  Ly 0.100M / FA 1.00%  / pH 7.0
8 (39)  Ly 0.100M / FA 1.00%  / pH 7.5
9 (59)  Ly 0.100M / FA 1.00%  / pH 8.0
10 Marker

02IE0011

1 Marker
2 Toxin, pH 7.0
3 (21)   Ly 0.000M / FA 0.50% / pH 7.5
4 (23)   Ly 0.025M / FA 0.50% / pH 7.5
5 (29)   Ly 0.050M / FA 0.50% / pH 7.5
6 (31)   Ly 0.050M / FA 0.75% / pH 7.5
7 (33)   Ly 0.050M / FA 1.00% / pH 7.5
8 (35)   Ly 0.100M / FA 0.50% / pH 7.5
9 Toxin, pH 8.0
10 Marker

FIG. 9
Starting concentration: 500 LF/ml
Detoxified with 1% Formalin
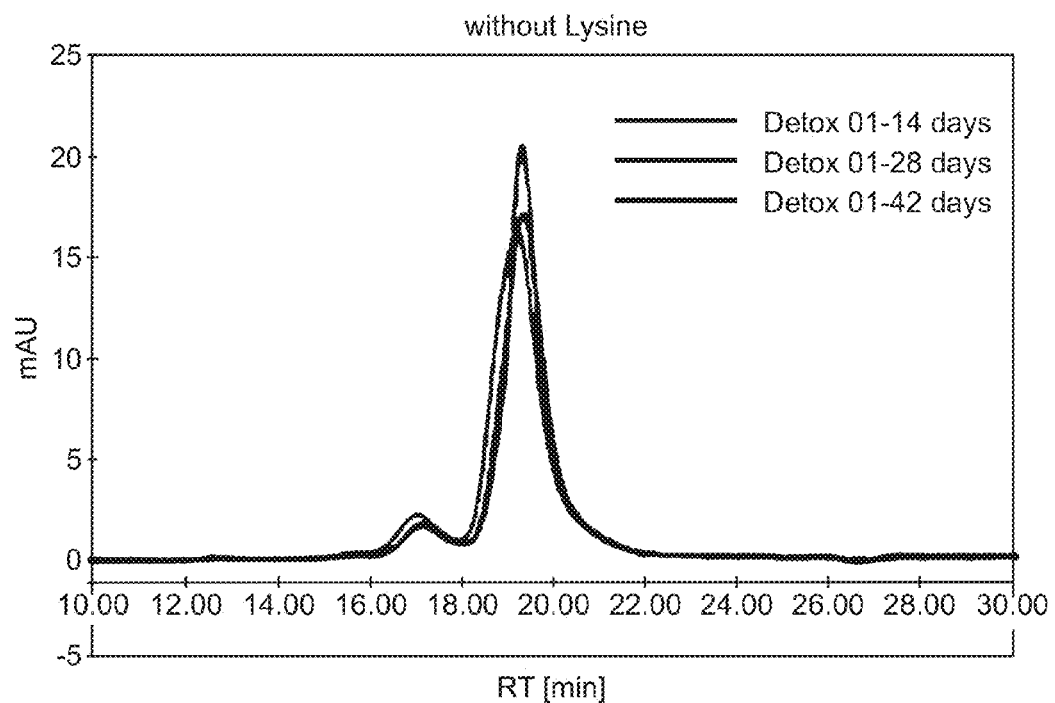
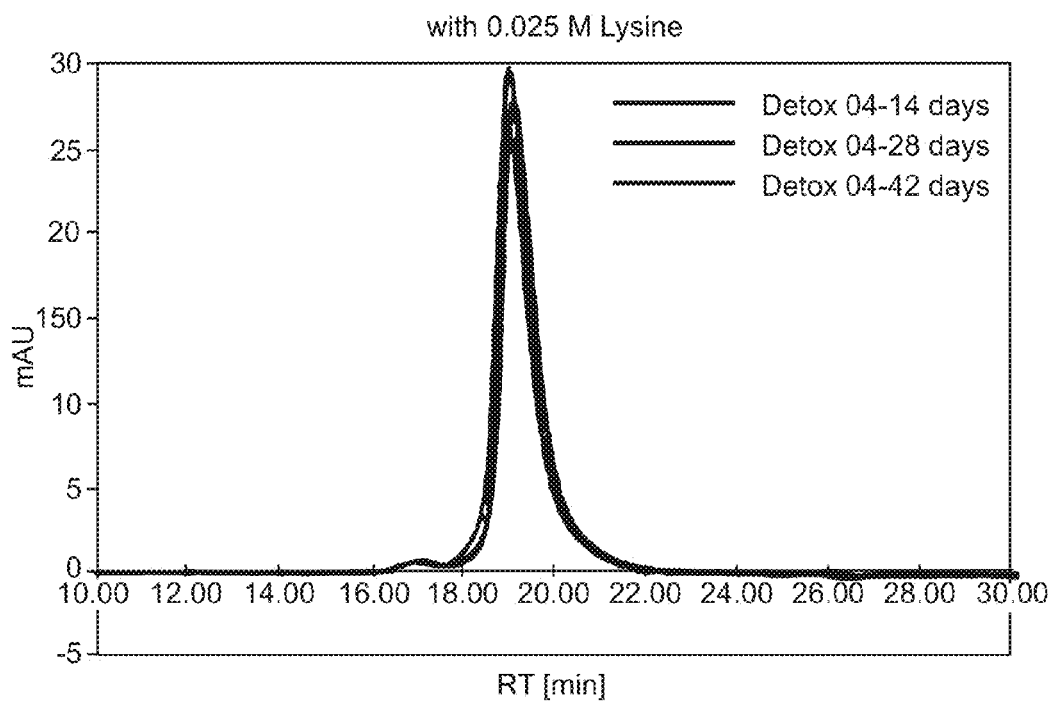

FIG. 10
Starting concentration: 2000 LF/ml
Detoxified with 1% Formalin
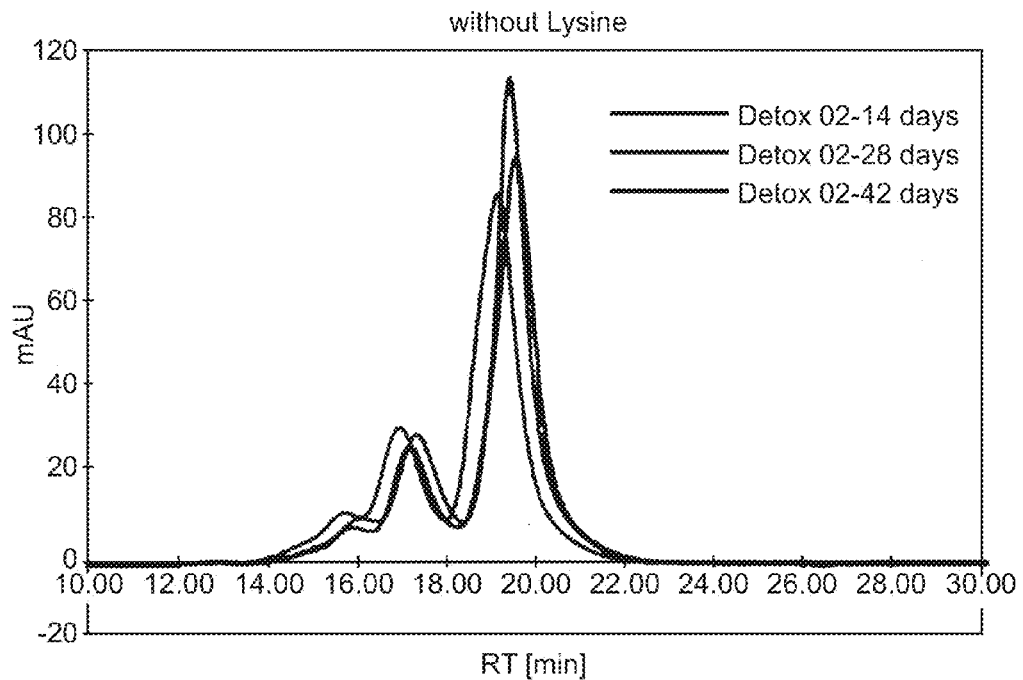
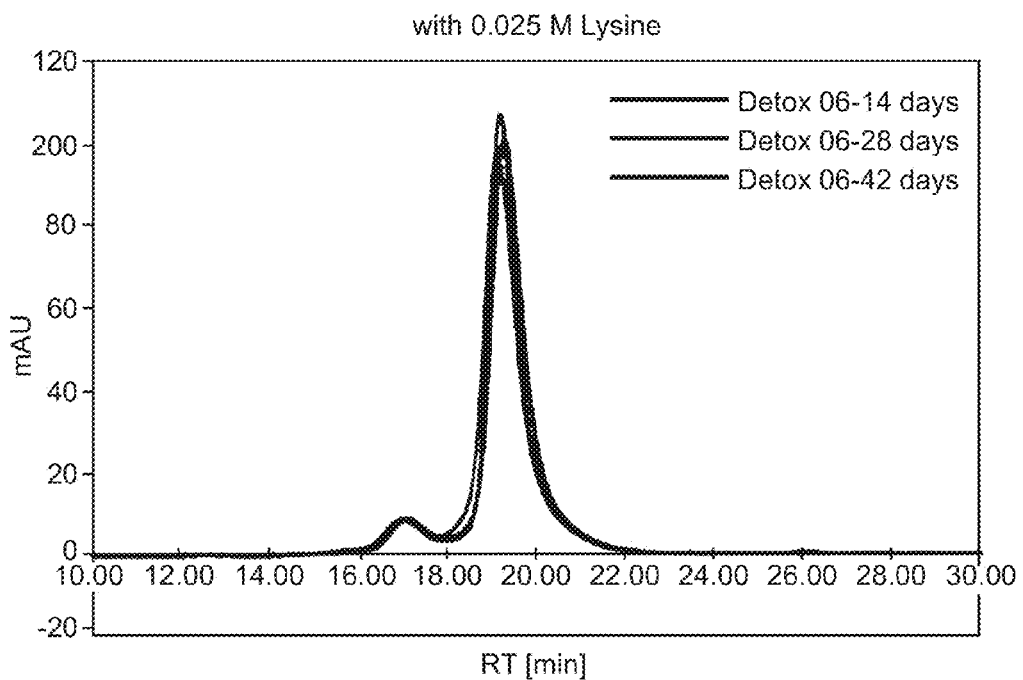

FIG. 11
Starting concentration: 5000 LF/ml
Detoxified with 1% Formalin
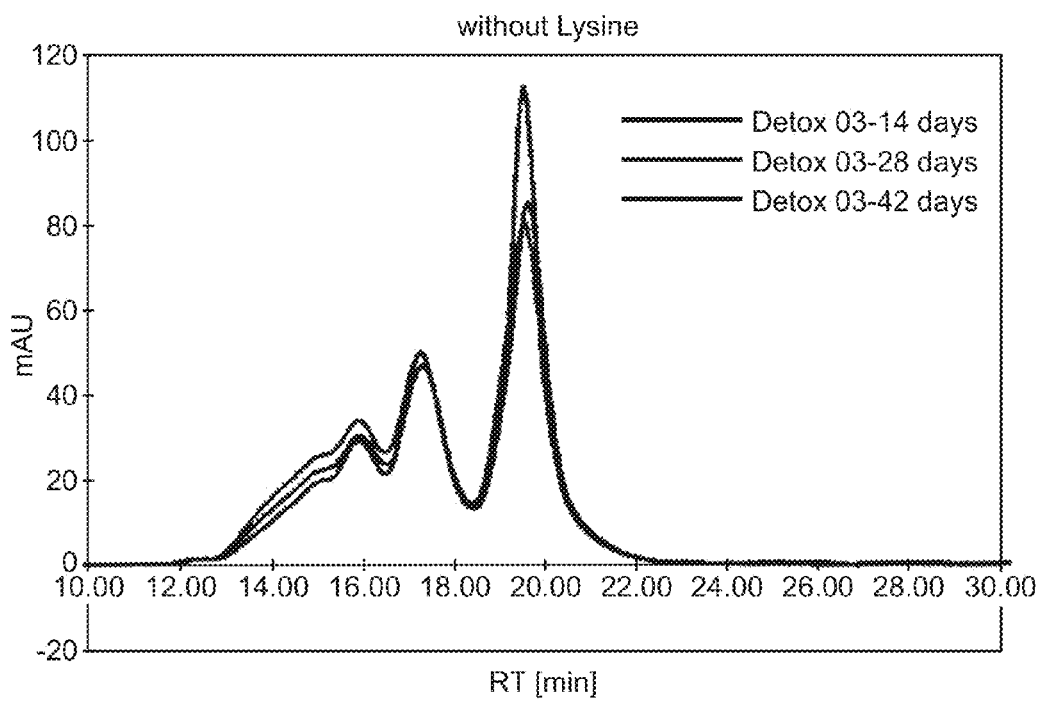
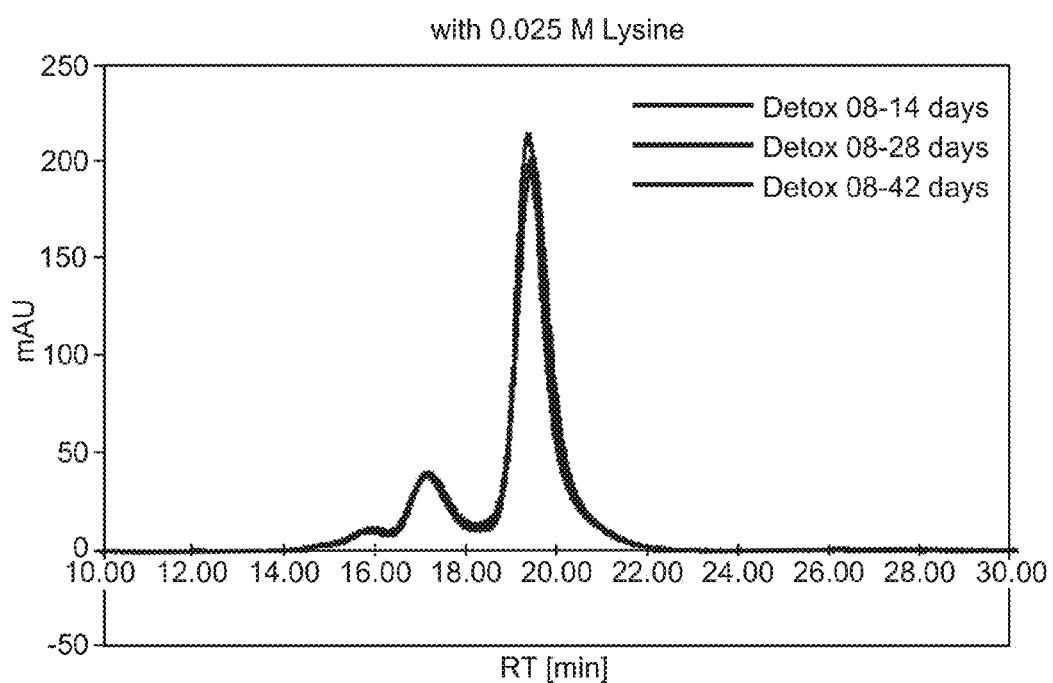

FIG. 12

```
┌─────────────────────────────────────────────────┐
│          Diphtheria toxin concentrate 2         │
└─────────────────────────────────────────────────┘
                        │
┌─────────────────────────────────────────────────┐
│   TMAE anion exchange column, elution of toxin  │
│      with 25 mM Tris, 90 mM NaCl, pH 7.5        │
└─────────────────────────────────────────────────┘
                        │
┌─────────────────────────────────────────────────┐
│           filtersterilization 0.22 μm           │
└─────────────────────────────────────────────────┘
                        │
┌─────────────────────────────────────────────────┐
│ Concentration to 1,000 LF/mL, diafiltration 30 kDa │
│      (0.1 M sodium phosphate buffer pH 7.5)     │
└─────────────────────────────────────────────────┘
                        │
┌─────────────────────────────────────────────────┐
│    Adjustment to 5,000 LF/mL in 0.1 M sodium    │
│            phosphate buffer pH 7.5              │
└─────────────────────────────────────────────────┘
                        │
┌─────────────────────────────────────────────────┐
│           filtersterilization 0.22 μm           │
└─────────────────────────────────────────────────┘
                        │
┌─────────────────────────────────────────────────┐
│     Detoxification, 1% formalin, 6 weeks, 37 °C │
└─────────────────────────────────────────────────┘
                        │
┌─────────────────────────────────────────────────┐
│            Particle filtration 0.45 μm          │
└─────────────────────────────────────────────────┘
                        │
┌─────────────────────────────────────────────────┐
│  Concentration to 10,000 LF/mL, diafiltration in │
│              NaCl solution 8.5 g/L              │
└─────────────────────────────────────────────────┘
                        │
┌─────────────────────────────────────────────────┐
│             pH adjustment to pH 7.5             │
└─────────────────────────────────────────────────┘
                        │
┌─────────────────────────────────────────────────┐
│           filtersterilization 0.22 μm           │
└─────────────────────────────────────────────────┘
                        │
┌─────────────────────────────────────────────────┐
│           Diphtheria toxoid concentrate         │
└─────────────────────────────────────────────────┘
```

FERMENTATION MEDIA FREE OF ANIMAL-DERIVED COMPONENTS FOR PRODUCTION OF DIPHTHERIA TOXOIDS SUITABLE FOR HUMAN VACCINE USE

CROSS REFERENCE TO RELATED APPLICATIONS

This application claims the benefit under 35 USC 119(e) of prior copending United Kingdom patent application Serial No. 1119517.9, filed Nov. 11, 2011, and U.S. Provisional patent application Ser. No. 61/629,176, filed Nov. 14, 2011, all of which are hereby incorporated by reference in the present disclosure in their entirety.

FIELD OF THE INVENTION

The invention relates to a fermentation medium for cultivating *Corynebacterium diphtheriae*. The invention also relates to the use of the fermentation medium in processes for obtaining diphtheria toxin from the *C. diphtheriae* bacteria being cultivated, to the preparation of vaccines using the diphtheria toxin obtained in the processes, and to the toxins themselves. The invention further relates to purification and detoxification processes for preparing diphtheria toxoids from the toxin e.g. for inclusion in a vaccine.

BACKGROUND

*Corynebacterium diphtheriae* causes diphtheria. The bacterium produces a toxic protein, diphtheria toxin, which can be treated (e.g. using formalin or formaldehyde) to remove toxicity while retaining the ability to induce protective antitoxin antibodies after injection. This treatment is referred to as "detoxification" or "toxoiding", and the detoxified toxin is referred to as a "toxoid." The diphtheria toxoids are used in diphtheria vaccines and are described in more detail in chapter 13 of the book "*Vaccines*" [1] and in chapter 31 of *New Generation Vaccines* [2].

Any therapeutic that is administered to humans and has been produced using a biological process has the potential for introducing harmful substances into the human body. Such harmful substances may be part of the medium used during the biological process. For example, animal-derived medium components such as fetal bovine serum bear the risk of containing aberrantly-folded proteins such as prions. Proteins derived from cow's milk have been suggested to cause severe allergic reactions in young children with cow's milk allergy, particularly after administration of DTP booster vaccines [3]. A similar risk may also exist in person with beef allergy [4]. Traditionally, diphtheria toxoid was obtained by growing *C. diphtheriae* in growth medium containing animal-derived components (e.g. in Linggoud & Fenton medium), such as bovine extract and/or casamino acids derived from cow milk.

The use of proteinaceous material of non-animal origin removes this risk. EP-B-1849860 discloses a medium for cultivating *C. diphtheriae* comprising at least 20% by dry weight of a non-animal proteinaceous material which is a yeast extract [5]. WO2005/056773 discloses a *C. diphtheriae* culture medium for the production of diphtheria toxin, which is substantially free of animal-derived components, and methods for producing the toxin [6]. WO2006/042542 discloses a fermentation medium for producing bacterial toxins using a non-animal and non-soya derived protein source [7]. WO00/50449 discloses a method of purifying diphtheria toxin comprising fermenting a microorganism strain capable of producing diphtheria toxin using glucose as a carbon source. In a preferred embodiment, this patent application discloses the use of a growth medium containing no more than 1% yeast extract [8].

Although these media are based on non-animal derived protein sources, and so can decrease contamination risks, none of them results in high yields of diphtheria toxin during industrial production (e.g. using fermenters in the 100-600 L range), and low yields are a drawback of these processes. Accordingly, none of these processes yield a cross-linked diphtheria toxoid free from animal-derived components with high enough potency to render the diphtheria toxoid suitable for human vaccine production.

It is thus an object of the invention to provide further and improved fermentation media suitable for use in industrial-scale, high-yield manufacturing of diphtheria toxin for production of a high potency vaccine suitable human administration.

In traditional processes to prepare diphtheria toxoid, the toxin is treated with formaldehyde in the presence of culture medium components e.g. see FIG. 4 of chapter 31 in reference 2. As well as cross-linking and detoxifying the diphtheria toxin, the formaldehyde causes covalent cross-linking of the medium components. This cross-linking means that the animal-derived components, if present in a growth medium, can be irreversibly locked into a human vaccine product. Higher purity toxoids for vaccine use can be obtained by purifying the toxin before the formaldehyde treatment. Patent Application GB-969772 discloses a method for producing toxoids from diphtheria toxin, comprising treating the toxin in an aqueous medium with formaldehyde in the presence of an aliphatic diamine of molecular weight below 200 which contains a primary or secondary amino group [9]. Frech et al. [10] discloses a physiochemical analysis of two purified diphtheria toxoids: the first was prepared by a conventional process in which the diphtheria toxin was formalinised and then purified; the second was first highly purified and then detoxified. WO2005/056773 discloses detoxification of an at least 75% pure diphtheria toxin. Even if high purity is achieved in a purification step preceding detoxification, however, residual animal-derived components of the fermentation medium used to prepare the diphtheria toxin (e.g. proteins, polypeptides, peptides and amino acids) are cross-linked by formaldehyde to the diphtheria toxoid obtained during the detoxification step.

It is a further object of the invention to provide a diphtheria toxoid that is free from crosslinked animal-derived components. It is another object of the invention to provide further improved processes in which diphtheria toxin is first highly purified and then detoxified.

Metz et al. [11] demonstrate that glycine and formaldehyde concentrations during detoxification of diphtheria toxin affects the antigenic properties of the resulting diphtheria toxoids. In particular, the formaldehyde concentration used during detoxification directly influences the immunogenicity of diphtheria toxoids leading to up to a 15-fold difference in potency between different diphtheria toxoid preparations.

An additional object of the invention is to provide a diphtheria toxoid that is free from crosslinked animal-derived components that has a consistently high potency and can be employed in the preparation of vaccines suitable for use in humans.

SUMMARY OF THE INVENTION

A. Fermentation Media

The invention provides various media for culturing *Corynebacterium diphtheriae*. These media allow diphtheria toxin production at an industrial scale in fermenters having production volumes of at least 300 liters, with yields being consistently in the range of 200 Lf/mL to 250 Lf/mL (or higher). The media and processes disclosed herein can even exceed the yields achieved with animal-derived media in producing diphtheria toxin.

In general, the invention provides a fermentation medium suitable for culturing a strain of *Corynebacterium diphtheriae* to produce diphtheria toxin or a derivative thereof, wherein the medium is free from animal-derived components and comprises a nitrogen source, a carbon source, an iron supplement, phosphorus, and growth factors. The medium is particularly useful for high yield, industrial-scale production of diphtheria toxin for preparing vaccines for human use.

In one aspect, the invention provides a fermentation medium suitable for culturing a strain of *Corynebacterium diphtheriae* to produce diphtheria toxin or a derivative thereof, wherein the medium is free of animal-derived components and comprises water, deferrated yeast extract and at least 0.08 M of a disaccharide as a carbon source. In one embodiment, the fermentation medium comprises between 0.08 M and 0.16 M of the disaccharide. In a specific embodiment, the fermentation medium comprises 0.15 M of the dissacharide.

In another aspect, the invention provides a fermentation medium suitable for culturing a strain of *Corynebacterium diphtheriae* to produce diphtheria toxin or a derivative thereof, wherein the medium is free of animal-derived components and comprises water, deferrated yeast extract, and a salt of Fe(III).

In a further aspect, the invention provides a fermentation medium suitable for culturing a strain of *Corynebacterium diphtheriae* to produce diphtheria toxin or a derivative thereof, wherein the medium is free of animal-derived components and comprises water and a low-mannan yeast extract. In one embodiment, the low-mannan yeast extract is deferrated.

In yet a further aspect, the invention provides a fermentation medium suitable for culturing a strain of *Corynebacterium diphtheriae* to produce diphtheria toxin or a derivative thereof, wherein the medium is free of animal-derived components and comprises water, yeast extract that is free of components with a molecular weight greater than 30 kDa, and a salt of Fe(II) or Fe(III) at a concentration between 1.5 µM and 30 µM.

In a specific embodiment, the fermentation medium is free from animal-derived components and comprises:
  (i) deferrated yeast extract as a nitrogen source;
  (ii) between 0.08 M and 0.16 M of a reducing disaccharide (e.g. cellobiose or maltose) as a carbon source;
  (iii) 10-14 µM soluble Fe2+/Fe3+ in form of a gel-like precipitate as an iron source;
  (iv) a mixture of growth factors comprising magnesium, copper, zinc, manganese, pimelic acid, nicotinic acid and β-alanine; and
  (v) water.

During preparation, ultrafiltration is typically used to remove all components with a molecular weight greater than 30 kDa from the yeast extract dissolved in water before additional medium components are added.

B. Processes for Preparing a Fermentation Medium

The invention further provides a process for preparing a fermentation medium of the invention, comprising adding to water (i) a nitrogen source, (ii) a carbon source, and (iii) an iron supplement.

In one aspect, the invention provides a process for preparing a fermentation medium comprises dissolving yeast extract in water to yield a yeast extract solution, deferrating the yeast extract solution to obtain a deferrated yeast extract solution, and adding at least 0.08 M of a disaccharide to the deferrated yeast extract solution to prepare the fermentation medium. In one embodiment, between 0.08 M and 0.16 M of the disaccharide is added to the deferrated yeast extract solution. In a specific embodiment, 0.15 M of the disaccharide is added to the deferrated yeast extract solution.

In another aspect, the invention provides a process for preparing a fermentation medium that comprises dissolving yeast extract in water to make a yeast extract solution; deferrating the yeast extract solution to obtain a deferrated yeast extract solution, and adding a salt of Fe(III) to the deferrated yeast extract solution to prepare the fermentation medium. In one embodiment, the salt of Fe(III) is added to the deferrated yeast extract solution in combination with phosphate and a calcium salt to promote formation of a slow-release formulation of iron.

In a further aspect, the invention provides a process for preparing a fermentation medium, wherein the process comprises preparing a low-mannan yeast extract, and dissolving the low-mannan yeast extract in water to prepare the fermentation medium. In one embodiment, the process further comprises deferrating the low-mannan yeast extract.

In yet a further aspect, the invention provides a process for preparing a fermentation medium, wherein the process comprises dissolving yeast extract in water to make a yeast extract solution, ultrafiltrating the yeast extract solution using a membrane with a molecular weight cut-off greater than 30 kDa to remove all components with a molecular weight>30 kDa, deferrating the yeast extract solution to obtain a deferrated yeast extract solution, and adding a salt of Fe(II) or Fe(III) to the deferrated yeast extract solution to a final concentration between 1.5 µM and 30 µM to prepare the fermentation medium.

C. Processes for Producing a Diphtheria Toxin or a Derivative Thereof.

The invention further provides a process for growing *Corynebacterium diphtheriae* comprising culturing a strain of *Corynebacterium diphtheriae* in a fermentation medium of the invention.

In one aspect, the invention provides a process for preparing a diphtheria toxin or a derivative thereof comprising growing a strain of *Corynebacterium diphtheriae* expressing a diphtheria toxin or a derivative thereof in the fermentation medium of the invention and separating the diphtheria toxin or the derivative from the fermentation medium.

In another aspect, the invention provides a process for producing a diphtheria toxin or a derivative thereof comprising preparing a culture of a strain of *Corynebacterium diphtheriae* expressing a diphtheria toxin or a derivative thereof in at least 100 L of a fermentation medium free of animal-derived components, growing the culture to a concentration of at least 140 Lf/mL of the diphtheria toxin or the derivative in the fermentation medium, and separating the diphtheria toxin or the derivative from the fermentation medium.

D. Processes for Producing a Diphtheria Toxoid

The invention provides various processes for producing diphtheria toxoids. These processes ideally involve purification prior to detoxification, thereby minimising or avoiding cross-linking of medium components to the toxoid. Where yeast extracts have been used in the culture medium, the process should remove most (ideally all) residual yeast extract components from the diphtheria toxin prior to treatment with a suitable detoxifying agent (preferably formaldehyde), thereby avoiding the cross-linking of potentially-allergenic yeast components to the diphtheria toxoid. The high purity of the final diphtheria toxoid is also advantageous as the addition of preservatives can be avoided which further reduces the potential for adverse reactions during vaccination.

Moreover, if the purified material is concentrated prior to detoxification then it is possible to use smaller volumes during the detoxification step (e.g. treatment with formaldehyde). This initial concentration can be achieved, for instance, by several diafiltration steps that result in a more concentrated diphtheria toxin solution. The use of smaller volumes during the detoxification procedure is advantageous as it saves time as well as storage capacity.

Thus, in yet another aspect, the invention provides a process for preparing a diphtheria toxoid comprising growing a culture of a strain of *Corynebacterium diphtheriae* which expresses a diphtheria toxin in a fermentation medium of the invention, purifying the diphtheria toxin from the fermentation medium to obtain a purified diphtheria toxin, adding a suitable detoxifying agent (preferably formaldehyde) to the purified diphtheria toxin, and incubating the purified diphtheria toxin from the previous step to obtain the diphtheria toxoid.

In a further aspect, the invention provides a process for preparing a diphtheria toxoid comprising: (i) growing a strain of *Corynebacterium diphtheriae* expressing a diphtheria toxin or a derivative thereof in a fermentation medium, preferably at a volume of at least 100 liters and/or to provide a yield of at least 140 Lf/ml of toxin/derivative; (ii) separating the diphtheria toxin or the derivative from the fermentation medium to obtain a diphtheria toxin solution; (iii) preparing a diphtheria toxin concentrate from the diphtheria toxin solution, wherein the concentration of the diphtheria toxin or the derivative in the concentrate is at least 20-fold higher than the concentration of the diphtheria toxin or the derivative either in the fermentation medium obtained at the end of step (i) or in the toxin solution obtained at the end of step (ii); (iv) adding to the concentrate an amine and a suitable detoxifying agent (preferably formaldehyde), and incubating the concentrate from step (iv) to obtain the diphtheria toxoid. In one embodiment, the concentration of the diphtheria toxin or the derivative in the concentrate in step (iii) is between 20-fold and 36-fold higher than the concentration of the diphtheria toxin or the derivative in the fermentation medium.

In yet a further aspect, the invention provides a process for producing a diphtheria toxoid comprising (i) growing a strain of *Corynebacterium diphtheriae* expressing a diphtheria toxin or a derivative thereof in a fermentation medium comprising yeast extract as the only source of all essential amino acids, (ii) purifying the diphtheria toxin or derivative from the fermentation medium to obtain a purified diphtheria toxin or derivative, (iii) adding a suitable detoxifying agent (preferably formaldehyde) to the purified diphtheria toxin or derivative, and (iv) incubating the purified diphtheria toxin or derivative from step (iii) to obtain the diphtheria toxoid.

In yet another aspect, the invention provides a process for producing a diphtheria toxoid for the preparation of a vaccine for human use comprising (i) growing a strain of *Corynebacterium diphtheriae* expressing a diphtheria toxin or a derivative thereof in a fermentation medium that is free of animal-derived components, optionally wherein the fermentation medium comprises yeast extract, (ii) purifying the diphtheria toxin or derivative from the fermentation medium to obtain a purified diphtheria toxin or derivative having a purity of at least 1500 Lf/mg nitrogen, (iii) adding a suitable detoxifying agent (preferably formaldehyde) to the purified diphtheria toxin or derivative, and (iv) incubating the purified diphtheria toxin or derivative from step (iii) to obtain the diphtheria toxoid.

In another aspect, the invention provides a process for producing a diphtheria toxoid comprising (i) growing a strain of *Corynebacterium diphtheriae* expressing a diphtheria toxin or a derivative thereof in a fermentation medium that is free of animal-derived components, optionally wherein the fermentation medium comprises yeast extract, (ii) purifying the diphtheria toxin or derivative from the fermentation medium to obtain a purified diphtheria toxin or derivative, wherein the purified toxin or derivative is at least 85% pure, (iii) adding a suitable detoxifying agent (preferably formaldehyde) to the purified diphtheria toxin or derivative, and (iv) incubating the purified diphtheria toxin or derivative from step (iii) to obtain the diphtheria toxoid.

In a further aspect, the invention provides a process for producing a diphtheria toxoid comprising (i) growing a strain of *Corynebacterium diphtheriae* expressing a diphtheria toxin or a derivative thereof in a fermentation medium that is free of animal-derived components, optionally wherein the fermentation medium comprises yeast extract, (ii) purifying the diphtheria toxin or derivative from the fermentation medium using anion exchange chromatography to obtain a purified diphtheria toxin or derivative, (iii) adding a suitable detoxifying agent (preferably formaldehyde) to the purified diphtheria toxin or derivative, and (iv) incubating the purified diphtheria toxin or derivative from step (iii) to obtain the diphtheria toxoid.

In one particular aspect, the invention provides a process for producing a diphtheria toxoid comprising (i) preparing a solution of a diphtheria toxin or a derivative thereof at a concentration of at least 2000 Lf/mL, (ii) adding to the solution (a) an amine at a final concentration of no more than 0.025 M and (b) a suitable detoxifying agent (preferably formalin) at a final concentration in the range of 0.5-1% (e.g. 0.75-1%), and (iii) incubating the solution from step (ii) to obtain the diphtheria toxoid. Typically, the concentration of the diphtheria toxin or its derivative in the solution is in the range between 2000 Lf/mL and 5000 Lf/mL In a specific embodiment, the toxin concentration of the solution prepared in step (i) is about 5000 Lf/mL. For example, the invention provides a process for producing a diphtheria toxoid comprising (i) preparing a solution of a diphtheria toxin at a concentration of at least 2000 Lf/mL, (ii) adding to the solution (a) no more than 5 nmol of an amine per Lf of the diphtheria toxin and (b) between 12 and 55 nmol, preferably between 18 and 25 nmol formaldehyde per Lf of the diphtheria toxin, and (iii) incubating the solution from step (ii) to obtain the diphtheria toxoid. Typically, the concentration of the diphtheria toxin or its derivative in the solution is in the range between 2000 Lf/mL and 5000 Lf/mL. In a specific embodiment, the toxin concentration of the solution prepared in step (i) is about 5000 Lf/mL. The amine is preferably lysine.

In a specific embodiment, the invention provides a process for preparing a diphtheria toxoid comprising (i) growing a culture of a strain of *Corynebacterium diphtheriae* expressing a diphtheria toxin in a fermentation medium comprising yeast extract, (ii) purifying the diphtheria toxin from the fermentation medium to obtain a diphtheria toxin solution, (iii) adjusting the concentration of diphtheria toxin in the diphtheria toxin solution to at least 2000 Lf/mL to obtain a diphtheria toxin concentrate, (iv) adding to the concentrate (a) an amine to a final concentration of no more than 0.025 M and (b) a suitable detoxifying agent (preferably formalin) to a final concentration in the range of 0.5-1% (e.g. 0.75-1%), and (v) incubating the concentrate from step (iv) to obtain the diphtheria toxoid. Typically, the concentration of the diphtheria toxin or its derivative in the solution is in the range between 2000 Lf/mL and 5000 Lf/mL In a specific embodiment, the toxin concentration is adjusted to 5000 Lf/mL in step (iii). In a preferred embodiment, the amine is lysine and the detoxifying agent is formalin.

In a more specific embodiment, the invention provides a process for preparing a diphtheria toxoid suitable for vaccination comprising (i) growing a culture of a strain of *Corynebacterium diphtheriae* expressing a diphtheria toxin in a fermentation medium comprising yeast extract, (ii) purifying the diphtheria toxin from the fermentation medium to obtain a diphtheria toxin solution, (iii) adjust the concentration of diphtheria toxin in the diphtheria toxin solution to at least 2000 Lf/mL to obtain a diphtheria toxin concentrate, (iv) adding to the concentrate (a) no more than 5 nmol of an amine per Lf of the diphtheria toxin and (b) between 12 and 55 nmol, preferably between 18 and 25 nmol, formaldehyde per Lf of the diphtheria toxin, and (v) incubating the concentrate from step (iv) to obtain the diphtheria toxoid. Typically, the concentration of the diphtheria toxin or its derivative in the solution is in the range between 2000 Lf/mL and 5000 Lf/mL. In a specific embodiment, the toxin concentration is adjusted to 5000 Lf/mL in step (iii). The amine is preferably lysine.

In one embodiment, the invention provides a process for preparing a combination vaccine for human use comprising:
(i) preparing a culture of a strain of *Corynebacterium diphtheriae* expressing a diphtheria toxin or a derivative thereof in at least 100 L of a fermentation medium free from animal-derived components, comprising
a nitrogen source;
at least 0.08 M of a carbon source;
1.5 µM-30 µM soluble $Fe^{2+}/Fe^{3+}$;
phosphorus; and
growth factors;
(ii) growing the culture in aerobic conditions to a concentration of at least 140 Lf/mL of the diphtheria toxin or the derivative in the fermentation medium;
(iii) separating the diphtheria toxin or the derivative from the fermentation medium, wherein the separation step comprises a centrifugation step and a filtration step;
(iv) purifying the diphtheria toxin or the derivative obtained in step (iii) using anion exchange chromatography to obtain a solution comprising a purified diphtheria toxin or derivative;
(v) adjusting the concentration of the purified diphtheria toxin or derivative in the solution to at least 2000 Lf/mL to obtain a diphtheria toxin concentrate;
(vi) adding to the concentrate (a) an amine to a final concentration of no more than 0.025 M and (b) a suitable detoxifying agent (preferably formalin) to a final concentration in the range of 0.5-1% (e.g. 0.75-1%); and
(vii) incubating the concentrate from step (vi) to obtain the diphtheria toxoid.

E. Diphtheria Toxoids

Processes of the invention provide diphtheria toxoids which are better suited for human vaccine use than those which are currently produced. The toxoids are analytically distinct from known toxoids e.g. by their cross-linking, by the absence of cross-linked medium components, by potency, and/or by purity. In preferred embodiments, the diphtheria toxoid obtained by the processes disclosed herein is free from formaldehyde-crosslinked animal-derived components, and preferably is free from all crosslinked animal-derived components.

In one aspect, the invention provides a diphtheria toxoid for use in human vaccination obtainable by growing a strain of *Corynebacterium diphtheriae* that expresses a diphtheria toxin in a fermentation medium free of animal-derived components, separating the diphtheria toxin from the fermentation medium, and incubating the diphtheria toxin in the presence of a suitable detoxifying agent (preferably formaldehyde) to yield the diphtheria toxoid. In a specific embodiment, the diphtheria toxoid obtainable in this way is cross-linked by the detoxifying agent (preferably formaldehyde) to at least one component of the fermentation medium. These one or more components may include proteins, polypeptides, peptides or amino acids of the fermentation medium. In a particular embodiment, these components have a molecular weight of ≤30 kDa. In a specific embodiment, these components are yeast-derived.

The invention also provides a diphtheria toxoid prepared from diphtheria toxin produced by a *Corynebacterium diphtheriae* bacterium that expresses a diphtheria toxin, wherein the bacterium was grown in a fermentation medium which is free from animal-derived components, and wherein the toxoid is crosslinked to at least one component of the fermentation medium. These one or more components may include proteins, polypeptides, peptides or amino acids of the fermentation medium. In a particular embodiment, these components have a molecular weight of ≤30 kDa. In a specific embodiment, these components are yeast-derived.

In another aspect, the invention provides a diphtheria toxoid for use in human vaccination obtainable by a process comprising (i) growing a strain of *Corynebacterium diphtheriae* expressing a diphtheria toxin or a derivative thereof in at least 100 L of a fermentation medium that is free from animal-derived components, optionally wherein the fermentation medium comprises yeast extract, (ii) purifying the diphtheria toxin or derivative from the fermentation medium to obtain a purified diphtheria toxin or derivative, wherein the purified toxin or derivative is at least 85% pure and/or has a purity of at least 1500 Lf/mg nitrogen, (iii) adding a suitable detoxifying agent (preferably formaldehyde) to the purified diphtheria toxin or derivative, and (iv) incubating the purified diphtheria toxin or derivative from step (iii) to obtain the diphtheria toxoid. In a specific embodiment, the diphtheria toxoid obtained by this process is cross-linked by the detoxifying agent (preferably formaldehyde) to at least one component of the fermentation medium. These one or more components may include proteins, polypeptides, peptides or amino acids of the fermentation medium. In a particular embodiment, these components have a molecular weight of ≤30 kDa. In a specific embodiment, these components are yeast-derived, i.e. diphtheria toxoid obtained by the process of the invention may be cross-linked by the detoxifying agent to yeast-derived components (e.g. yeast proteins, yeast-derived polypeptides etc.).

In a specific embodiment, the invention provides a diphtheria toxoid for use in human vaccination obtainable by a process comprising:
(i) preparing a fermentation medium that is free of animal-derived components by dissolving a low-mannan yeast extract in water to yield a yeast extract solution, deferrating the yeast extract solution to obtain a deferrated yeast extract solution, ultrafiltering the deferrated yeast extract solution using a membrane with a molecular weight cut-off greater than 30 kDa, and adding 50 g/L of maltose, a growth factor solution and a salt of Fe(III) at a concentration between 10-14 µM to the deferrated yeast extract solution to prepare the fermentation medium, wherein the salt of Fe(III) is added in combination with phosphate and a calcium salt to promote formation of a slow-release formulation of iron;

(ii) preparing a culture of a strain of *Corynebacterium diphtheriae* that expresses a diphtheria toxin in at least 100 L of the fermentation medium;
(iii) growing the culture to a concentration of at least 140 Lf/mL of the diphtheria toxin in the fermentation medium;
(iv) separating the diphtheria toxin from the fermentation medium by centrifugation to yield a diphtheria toxin solution;
(v) filter-sterilizing the diphtheria toxin solution to yield a sterile diphtheria toxin;
(vi) purifying the sterile diphtheria toxin to obtain a purified diphtheria toxin;
(vii) adding a suitable detoxifying agent (preferably formaldehyde) to the purified diphtheria toxin; and
(viii) incubating the purified diphtheria toxin from step (ix) to obtain the diphtheria toxoid.

In another specific embodiment, the invention provides a diphtheria toxoid for use in human vaccination obtainable by a process comprising:
(i) preparing a culture of a strain of *Corynebacterium diphtheriae* that expresses a diphtheria toxin in at least 100 L of a fermentation medium that is free of animal-derived components and components with a molecular weight greater than 30 kDa, wherein the fermentation medium comprises (a) water, (b) a deferrated low-mannan yeast extract, (c) 50 g/L of maltose, (d) a growth factor solution comprising magnesium, copper, zinc, manganese, pimelic acid, nicotinic acid and β-alanine, (e) ammonium ferric citrate at a starting concentration between 10-14 µM, and (0 phosphate;
(ii) growing the culture under aerobic conditions to a concentration of at least 200 Lf/mL of the diphtheria toxin in the fermentation medium;
(iii) separating the diphtheria toxin from the fermentation medium by centrifugation to yield a diphtheria toxin solution;
(iv) filter-sterilizing the diphtheria toxin solution to yield a sterile diphtheria toxin;
(v) purifying the sterile diphtheria toxin to obtain a purified diphtheria toxin;
(vi) concentrating the purified diphtheria toxin at least 20-fold over the concentration of the diphtheria toxin in the fermentation medium to obtain a diphtheria toxin concentrate;
(vii) adding formaldehyde and lysine to the diphtheria toxin concentrate; and
(viii) incubating the diphtheria toxin concentrate in the presence of formaldehyde and lysine to obtain the diphtheria toxoid.

In a further specific embodiment, the invention provides a diphtheria toxoid suitable for use in human vaccination obtainable by a process comprising:
(i) growing a culture of a strain of *Corynebacterium diphtheriae* expressing a diphtheria toxin in a fermentation medium;
(ii) purifying the diphtheria toxin from the fermentation medium using anion exchange chromatography to obtain a solution comprising a purified diphtheria toxin having at least 2000 Lf/mg nitrogen;
(iii) adjusting the concentration of the purified diphtheria toxin in the solution to 5000 Lf/mL using diafiltration to obtain a diphtheria toxin concentrate;
(iv) adding to the concentrate (a) lysine to a final concentration of 0.025 M and (b) formalin to a final concentration of 1%;
(v) incubating the concentrate from the preceding step to obtain a diphtheria toxoid concentrate;
(vi) sterile-filtering the diphtheria toxoid concentrate to obtain a sterile solution;
(vii) adjusting the concentration of the diphtheria toxoid in the sterile solution to 10000 Lf/mL using diafiltration to obtain a concentrated solution; and
(viii) adjusting the pH of the concentrated solution to pH 7.5 to obtain a diphtheria toxoid suitable for use in human vaccination.

In another aspect, the invention provides a diphtheria toxoid obtainable by detoxification of a diphtheria toxin (e.g. using formaldehyde treatment) having a concentration of at least 2000 Lf/mL. Detoxification can involve (as disclosed elsewhere herein) adding to a solution of the toxin (a) an amine at a final concentration of no more than 0.025 M and (b) a suitable detoxifying agent (preferably formalin) at a final concentration in the range of 0.5-1% (e.g. 0.75-1%). For example, detoxification can involve (as disclosed elsewhere herein) adding to a solution of the toxin (a) no more than 5 nmol of an amine per Lf of the diphtheria toxin and (b) between 12 and 55 nmol, preferably between 18 and 25 nmol, formaldehyde per Lf of the diphtheria toxin. The amine is preferably lysine. These amounts of formaldehyde (and, optionally, of the amine e.g. lysine) are known in the art, but not for treatment of toxin at such a high concentration. The altered ratio provides a toxoid which is molecularly distinct from known toxoids.

The invention also provides a diphtheria toxoid obtainable by a process of the invention as described herein. In particular, the invention provides a diphtheria toxoid obtainable by a process as disclosed in the examples herein (e.g. obtainable by growing a *C. diphtheriae* in the medium of Table 3, purifying toxin, and detoxifying the toxin, as disclosed herein).

F. Compositions Suitable for Human Vaccination

The invention provides a composition suitable for human vaccination comprising a diphtheria toxoid which is free from formaldehyde-crosslinked animal-derived components (and preferably free from all crosslinked animal-derived components) and has a potency of at least 60 IU/ml Similarly, the invention provides a composition suitable for human vaccination, comprising a diphtheria toxoid purified from *Corynebacterium diphtheriae* grown in a culture medium free from animal-derived components and having a potency of at least 60 IU/ml. In one embodiment, the composition has a monomer:dimer ratio of the diphtheria toxoid in the range of 3:1 to 10:1, preferably in the range of 3:1 to 6:1 (or 4:1 to 9:1), and the diphtheria toxoid can have an isoelectric point in the range of 4.0 to 5.0. In another embodiment, at least 70% of the toxoid is in monomeric form. In a further embodiment, the composition comprises a protective antigen from at least one pathogen other than *Corynebacterium diphtheriae*. For example, the protective antigen may be selected from hepatitis B virus surface antigen (HBsAg), tetanus antigen, pertussis antigen, *H. influenzae* type B capsular saccharide, a *N. meningitidis* capsular saccharide, *S. pneumoniae* capsular saccharide, and IPV.

The invention also provides a composition suitable for human vaccination, comprising a crosslinked diphtheria toxoid with an isoelectric point in the range of 4.0 to 5.0 and which is free from crosslinked animal-derived components, wherein at least 70% of the toxoid is in monomeric form. The invention also provides a composition suitable for human vaccination, comprising a crosslinked diphtheria toxoid which is free from crosslinked animal-derived components, wherein at least 70% of the toxoid is in monomeric form. For example, the composition may comprise a formaldehyde-linked diphtheria toxoid which is free from formaldehyde-linked animal-derived components, wherein at least 70% of the toxoid is in monomeric form. Preferably, a composition suitable for human vaccination comprises a formaldehyde-linked diphtheria toxoid with an isoelectric point in the range of 4.0 to 5.0 that is free from formaldehyde-linked animal-derived components, wherein at least 70% of the toxoid is in monomeric form. As discussed above, these compositions can include a protective antigen from at least one pathogen other than *C. diphtheriae*.

The percentage of toxoid in monomeric form can be determined by size-exclusion chromatography. The area under the curve is used to calculate the percentage of toxoid in monomeric form using the following formula:

$$\% \text{ monomer} = \text{area}_{monomer}/(\text{area}_{dimer} + \text{area}_{monomer}) \times 100$$

In one specific embodiment, the invention provides a composition suitable for human vaccination, comprising a diphtheria toxoid free of formaldehyde-crosslinked animal-derived components (and preferably free from all crosslinked animal-derived components) and at least one protective antigen from a pathogen other than *Corynebacterium diphtheriae*. In another specific embodiment, the invention provides a composition suitable for human vaccination, comprising a diphtheria toxoid which is free from formaldehyde-crosslinked animal-derived components (and preferably free from all crosslinked animal-derived components) and which has a monomer:dimer ratio in the range of 3:1 to 8:1, more preferably in the range of 3:1 to 6:1, and wherein the diphtheria toxoid has an isoelectric point in the range of 5.0 to 4.0. In a further specific embodiment, the invention provides a composition suitable for human vaccination, comprising a diphtheria toxoid which is free from formaldehyde-crosslinked animal-derived components (and preferably free from all crosslinked animal-derived components) and wherein at least 70% of the diphtheria toxoid is in monomeric form.

In yet another embodiment, the invention provides a composition for use in preparing a human vaccine, comprising: (i) between 100-250 Lf/ml diphtheria toxoid which is free from formaldehyde-crosslinked animal-derived components (and preferably free from all crosslinked animal-derived components); (ii) between 40-100 Lf/ml tetanus toxoid; wherein the ratio of diphtheria toxoid to tetanus toxoid in the composition is between 2:1 and 3:1. In a particular embodiment, the composition does not comprise any other antigens except diphtheria toxoid and tetanus toxoid.

In a further embodiment, the invention provides a composition suitable for human vaccination, comprising a diphtheria toxoid of the invention adsorbed to an insoluble aluminium salt adjuvant (e.g. aluminium hydroxide). For instance, the invention provides a composition suitable for human vaccination, comprising a diphtheria toxoid which is free from formaldehyde-crosslinked animal-derived components (and preferably free from all crosslinked animal-derived components) and which is adsorbed to an insoluble aluminium salt adjuvant (e.g. aluminium hydroxide) Similarly, the invention provides a composition suitable for human vaccination, comprising a diphtheria toxoid purified from *Corynebacterium diphtheriae* grown in a culture medium free from animal-derived components and having a potency of at least 60 IU/ml, which is adsorbed to an insoluble aluminium salt adjuvant (e.g. aluminium hydroxide).

Diphtheria toxoids of the invention can be used as carrier proteins in saccharide conjugates. Thus, in a further aspect, the invention provides a conjugate of a bacterial saccharide and a diphtheria toxoid carrier protein, wherein the diphtheria toxoid which is as variously defined above (e.g. which is free from formaldehyde-crosslinked animal-derived components or, preferably, free from all crosslinked animal-derived components).

In yet a further aspect, the invention provides vaccine formulations comprising the diphtheria toxoid of the invention and compositions comprising the same.

In a specific embodiment, the invention provides a combination vaccine comprising (i) a diphtheria toxoid which is free from formaldehyde-crosslinked animal-derived components (and preferably free from all crosslinked animal-derived components) and has a potency of at least 60 IU/ml, and (ii) a protective antigen from at least one pathogen other than *Corynebacterium diphtheriae*. The protective antigen may be selected from hepatitis B virus surface antigen (HBsAg), a *H. influenzae* type B capsular saccharide, and a *N. meningitidis* capsular saccharide. Preferably, the HBsAg is free from animal-derived components. Preferably, the *H. influenzae* type B capsular saccharide is free from animal-derived components. Preferably, the *N. meningitidis* capsular saccharide is free from animal-derived components.

The invention also provides a combination vaccine comprising (i) a diphtheria toxoid obtainable by detoxification of a diphtheria toxin (e.g. using formaldehyde treatment) having a concentration of at least 2000 Lf/mL, as described above; and (ii) a protective antigen from at least one pathogen other than *Corynebacterium diphtheriae*, as described above.

In general, the invention also provides a human vaccine comprising a diphtheria toxoid of the invention, wherein (i) the toxoid is adsorbed to an insoluble aluminium salt adjuvant and/or (ii) the vaccine includes a protective antigen from at least one pathogen other than *C. diphtheriae.*

G. Processes for Preparing Compositions Suitable for Human Vaccination

In a further aspect, the invention provides a process for preparing a composition suitable for human vaccination, comprising steps of combining: (i) a diphtheria toxoid which is free from formaldehyde-crosslinked animal-derived components (and preferably free from all crosslinked animal-derived components); (ii) HBsAg which is free from animal-derived components; (iii) *H. influenzae* type B capsular saccharide which is free from animal-derived components; and (iv) *N. meningitidis* capsular saccharide which is free from animal-derived components.

In one embodiment, the invention provides a process for preparing a human vaccine, comprising mixing a composition that comprises (i) between 100-250 Lf/ml diphtheria toxoid which is free from formaldehyde-crosslinked animal-derived components (and preferably free from all crosslinked animal-derived components), and (ii) between 40-100 Lf/ml tetanus toxoid, wherein the ratio of diphtheria toxoid to tetanus toxoid in the composition is between 2:1 and 3:1, with at least one further antigen-containing composition. In a specific embodiment, the process results in a human vaccine that comprises between 20-30 Lf/ml diphtheria toxoid and between 5-15 Lf/ml tetanus toxoid.

The invention also provides a process for preparing a composition suitable for human vaccination, comprising steps of combining: (i) a diphtheria toxoid purified from *Corynebacterium diphtheriae* grown in a culture medium free from animal-derived components; (ii) HBsAg which is free from animal-derived components; (iii) *H. influenzae* type B capsular saccharide which is free from animal-derived components; and (iv) *N. meningitidis* capsular saccharide which is free from animal-derived components. The composition can include diphtheria toxoid with a potency of at least 60 IU/ml.

DETAILED DESCRIPTION OF THE INVENTION

Fermentation Media

In one aspect, the invention relates to fermentation media that are suitable for culturing a strain of *C. diphtheriae* to produce diphtheria toxin or a derivative thereof. In order to support bacterial growth, the medium should include a nitrogen source, a carbon source, a phosphorus source, and growth factors. In order to support toxin production by the bacterium, the medium should contain a suitable source of iron.

In preferred embodiments the medium is free from animal-derived components. Thus all components in the medium should be prepared from non-animal sources. The components may, for instance, be prepared from plant sources (e.g. from soy), or may be synthetic, but meat and milk components are not used.

Nitrogen Source

The nitrogen source of the fermentation medium of the invention is preferably a yeast extract. Yeast extracts are generally obtained by salt-free autolysis of primary yeast and subsequent extensive purification, which renders the yeast extract free from undesired components such as spores and DNA.

In one embodiment, the yeast extract is low in mannans. Methods for preparing low-mannan yeast extracts are known in the art. For example, a low-mannan yeast extract can be prepared by removing polysaccharides from a conventionally prepared yeast extract through ultrafiltration. Alternatively, a low-mannan yeast extract may be prepared from a yeast strain that expresses reduced amounts of mannans. A yeast strain that expresses reduced amounts of mannans (e.g., less than 70% of wild-type levels) is partially deprived of its cell wall integrity, easily releases its intracellular content, and is therefore especially suitable to prepare yeast extracts with little variation from batch to batch. Ideally, a low-mannan yeast strain is able to grow in liquid medium to be suitable for yeast extract preparation on an industrial scale. Such a yeast strain may be a yeast strain in which one or more genes required for mannan expression have been mutated. Alternatively, a naturally occurring yeast strain that expresses low levels of mannans may be used to prepare yeast extract. Examples for yeast strains with a cell wall having a low mannan content and methods for producing the same are disclosed in references 12 and 13. In particular, naturally occurring yeast strains or chemically or physically mutagenised yeast strains may be screened for low-mannan content in the cell wall using Gram-staining. Gram-positive strains that are also low in electron density of the outer layer of cell wall by electron microscopic inspection are likely to have a low mannan content. Mannan content may be determined by chemical analysis. Alternatively, the low mannan content of the cell wall of the yeast can be confirmed with mannan-specific antibodies or lectins such as concanavalin A.

In another embodiment, the yeast extract is an ultrafiltered yeast extract e.g. the product of ultrafiltration of a crude yeast extract. For instance, a step of ultrafiltration can be included during preparation of the yeast extract solution, or an existing yeast extract solution can be subjected to ultrafiltration prior to its use in preparing a fermentation medium of the invention. In a specific embodiment, ultrafiltration is used to remove all components with a molecular weight greater than 30 kDa from the yeast extract solution. By removing high-molecular weight components from the yeast extract, spores as well as proteins and DNA that were not sufficiently hydrolysed are removed minimizing batch-to-batch variation between different yeast extract preparations and guaranteeing a highly reproducible fermentation process.

In a further embodiment, the yeast extract is deferrated. As explained below, high iron concentrations inhibit the expression of the diphtheria toxin during the growth of *C. diphtheriae*. Methods for deferrating a yeast extract are commonly known to the skilled person. For example, the process described by Stainer & Scholte [14] may be used to precipitate iron from the yeast extract prior to its use in a fermentation medium. Iron can be precipitated by dissolving yeast extract in water, adjusting the pH to 9.3, adding $Na_2HPO_4$ and $KH_2PO_4$ to the yeast extract solution, heating the solution to 85° C., and adding $CaCl_2$. The precipitate is then formed by slowly cooling the solution. Particularly good results were achieved by dissolving yeast extract in water, adjusting the pH to 9.3, heating the solution to 60° C., adding $Na_2HPO_4$ and $KH_2PO_4$ to the yeast extract solution, further heating the solution to 79° C., adding $CaCl_2$, further heating the solution to 85° C., and then cooling the solution to 25° C. over a period of three hours to allow the iron precipitate to form. The precipitate can be removed e.g. by filtration or centrifugation.

In a preferred embodiment, ultrafiltration and deferratation of the yeast extract are combined. It was found that the combination of both ultrafiltration and deferratation of the yeast extract prior to the addition of both the growth factors and an iron supplement resulted in a fermentation medium that yields diphtheria toxin of about 200 Lf/ml or more when used to grow *C. diphtheriae*.

In another preferred embodiment, the yeast extract is the sole source of all essential amino acids in the fermentation medium. While some amino acids such as β-alanine and L-cysteine may be added separately as part of the growth factors, yeast extract can provide all amino acids required for the growth of *C. diphtheriae* and therefore reduces the number of components needed to prepare the fermentation medium as well the overall cost of providing a chemically defined medium.

In a further embodiment, instead of using a yeast extract, the nitrogen source of the fermentation medium can be selected from a rice wheat peptone, a rice peptone, a wheat peptone, a soy peptone, a cotton peptone, a pea peptone, and a potato peptone. In some embodiments, however, a fermentation medium does not include soy peptone. In other embodiments, a fermentation medium in accordance with the invention does not include any plant- or animal derived materials.

The use of yeast extract as the nitrogen source in the fermentation medium of the invention is particularly preferred. Plant-derived components such as plant peptones are agricultural products and so, if proper procedures are not followed, cannot be guaranteed to be e.g. free from adventitious viruses. For example, parvoviruses can be found in the faeces of their host animals such as cows. Parvovirus-contaminated faeces may be used as fertilizer and therefore may contaminate a plant peptone derived from a plant grown in the presence of parvovirus-contaminated faeces. Parvoviruses can infect tissue culture cells and may interfere with quality control assays such as the Vero cell assay used to determine the residual toxicity of diphtheria toxoid preparations after detoxification. In addition, the presence of viral components in diphtheria toxoid prepared with plant-derived components may cause adverse reactions in human subjects receiving a vaccine comprising the toxoid. Where proper controls are in place, however, plant-derived components can be used.

Carbon Source

Various carbon sources have been used to grow *C. diphtheriae* including glucose and glycerol. The addition of a separate carbon source is not absolutely necessary if a carbon-containing nitrogen source is used (*C. diphtheriae* can assimilate carbon from amino acids), but growth rates are much higher during fermentation if an additional carbon source is present.

In general, the higher the concentration of the carbon source, the higher the yield of toxin that can be achieved during culture. However, high concentrations of monosaccharides such as glucose can cause problems due to the increased osmolality of the medium. In addition, *C. diphtheriae* produces lactic acid as a by-product of anaerobic fermentation that may occur when the bacteria encounter low oxygen conditions during the fermentation process (e.g. due to insufficient aeration). The use of monosaccharaides as the carbon source leads to a large pH drop due to the accumulation of lactic acid in the fermentation medium. Low pH of the fermentation medium reduces or inhibits toxin production and therefore should be avoided if high yields of toxin are desired. Using a disaccharide in place of the monosaccharide leads to a smaller decrease in pH under low oxygen conditions and therefore increases toxin yield. Thus, in order to provide maximal amounts of a carbon source for optimal growth of *C. diphtheriae* under fermentation conditions, the use of a dissacharide in the fermentation medium is preferred.

In one embodiment, the fermentation medium comprises at least 0.08 M of a disaccharide as carbon source. In another embodiment, the fermentation medium comprises between 0.08 M and 0.16 M of a disaccharide as a carbon source. In a further embodiment, the fermentation medium comprises between 0.1 M and 0.15 M of a disaccharide as a carbon source. In a specific embodiment, the concentration of the disaccharide in the fermentation medium of the invention is about 0.15 M.

Various disaccharides may be used in the fermentation medium of the invention and in the process of preparing the fermentation medium. Suitable disaccharides include sucrose, lactulose, lactose, maltose, trehalose, and cellobiose. In a specific embodiment, the disaccharide of the fermentation medium is a reducing disaccharide such as cellobiose or maltose. In a particular embodiment, the disaccharide is maltose.

Excellent yields of diphtheria toxin were achieved, when *C. diphtheriae* was grown in a fermentation medium supplemented with 50 g/L maltose.

Phosphorus

Phosphorus in form of phosphate is an essential component of many biomolecules. For example, DNA, RNA and the phospholipids that form the cell membrane contain phosphate. Therefore, phosphorus is an essential component of the fermentation medium of the invention. If yeast extract is used as a nitrogen source, the addition of phosphorus to the fermentation medium is typically not required because yeast extract contains sufficient sources of phosphate in form of e.g., nucleotides and phospholipids.

Growth Factors

During rapid growth of *C. diphtheriae* in a fermenter, certain components of the fermentation may become rate-limiting. By supplementing the fermentation medium with these components the yield of diphtheria toxin can further be improved. Therefore, these components are generally referred to as "growth factors."

Suitable growth factors include magnesium, copper, zinc, manganese, pimelic acid, nicotinic acid and β-alanine. In some embodiments, magnesium is provided in form of $MgSO_4 \cdot 7H_2O$, copper is provided in form of $CuSO_4 \cdot 5H_2O$, zinc is provided in form of $ZnSO_4 \cdot 7H_2O$, and manganese is provided in form of $MnCl_2 \cdot 4H_2O$.

Iron Source

High iron concentrations in a culture medium inhibit the expression of the diphtheria toxin during growth of *C. diphtheriae*. Removing excess iron from the medium is therefore necessary to give high-yield toxin production during fermentation of *C. diphtheriae*. Methods for deferrating culture media are commonly known to the skilled person e.g. as described by Stainer & Scholte [14]. For example, iron can be removed from a yeast extract solution by precipitating the iron present in the solution and removing the precipitate by centrifugation and/or ultrafiltration.

If levels of iron are too low, however, growth of *C. diphtheriae* is negatively affected. After deferration, therefore, a fermentation medium should still provide a source of iron during growth, but not at levels which prevent the production of diphtheria toxin. The main source of iron in the fermentation medium can stem from the material used as a nitrogen source, which traditionally has been animal-derived. If a yeast extract is used as a source of nitrogen, it may be deferrated to lower the iron concentration to a level that allows high-yield diphtheria toxin production during fermentation. However, if iron levels are so low that bacterial growth is inhibited (e.g. after total deferration) the fermentation medium must be supplemented with iron to support growth of *C. diphtheriae*.

In one embodiment, a fermentation medium comprises a salt of Fe(III). One example of a salt of Fe(III) is ammonium ferric citrate. In another embodiment, the fermentation medium comprises a salt of Fe(II). One example for a salt of Fe(II) is ferrous sulphate heptahydrate. In one embodiment, the starting Fe(II) or Fe(III) concentration in a fermentation medium is between 1.5 µM and 30 µM. In another embodiment, the starting Fe(II) or Fe(III) concentration is between 3-15 µM. In a further embodiment, the starting Fe(II) or Fe(III) concentration is between 5-13 µM. In a specific embodiment, the starting Fe(II) or Fe(III) concentration is between 10-14 µM.

In order to allow sufficient amounts of iron to be present throughout the fermentation process, but without reaching concentrations which inhibit toxin production, an iron supplement is generally added as a slow-release formulation. Thus, in a specific embodiment, the fermentation medium is supplemented with a slow-release formulation of iron. A slow-release formulation of iron to supplement the fermentation medium can be produced by adding an ammonium ferric citrate solution and a phosphate solution to the fermentation medium prior to its use and by precipitating the iron through addition of a calcium chloride solution. This leads to the formation of a gel-like precipitate that slowly releases iron into the fermentation medium during the fermentation process. Other ways of obtaining a slow-release formulation of iron will be apparent to the skilled person and are likewise encompassed by the invention.

Media Forms

Fermentation media can be prepared as liquid medium or as solid medium. Alternatively, the fermentation medium may be prepared as dried powder. In one embodiment, solid medium may be prepared by the addition of agar to a liquid medium. A solid medium prepared in accordance with the invention might be especially useful to prepare a master seed bank of *C. diphtheriae*. The master seed may be used to prepare a working seed. The working seed in turn is used to inoculate the fermentation medium of the invention for growing large amounts of *C. diphtheriae* in the preparation of diphtheria toxin for use in vaccines.

Media Preparation

In one aspect the invention relates to a process for preparing the fermentation medium of the invention. In one embodiment, a process for preparing the fermentation medium of the invention comprises adding to water (or to another aqueous liquid) a nitrogen source and a carbon source. Depending on iron levels of the material used as nitrogen source, the process may also comprise adding an iron supplement. Further, the process may comprise adding growth factors and phosphorus.

In a particular embodiment, a process for preparing a fermentation medium of the invention comprises dissolving yeast extract in water, deferrating the yeast extract, and adding a disaccharide to a final concentration of at least 0.08 M (see above).

In another embodiment, the invention relates to a process for preparing a fermentation medium, wherein the process comprises dissolving yeast extract in water, deferrating the yeast extract, and adding a salt of Fe(II) or Fe(III). The salt of Fe(II) or Fe(III) may be added in such a way that a slow release formulation of iron is formed (see above).

In another embodiment, a process for preparing a fermentation medium of the invention can include a step of ultrafiltrating a yeast extract.

In yet another embodiment, the invention relates to a process for preparing a fermentation medium, wherein the process comprises preparing a low-mannan yeast extract and dissolving the yeast extract in water.

Any of the processes described above may be combined to prepare the fermentation medium of the invention. For example, in addition to dissolving yeast extract in water, deferrating the yeast extract, and adding between 0.08 M and 0.16 M of disaccharide, the process for preparing the fermentation medium of the invention may further comprise one or more ultrafiltration step. Alternatively or in addition, a salt of Fe(II) or Fe(III) may be added to the fermentation medium prior to its use.

Uses of Media

Fermentation media may be used in a process for growing *C. diphtheriae* comprising culturing a strain of *C. diphtheriae* in a fermentation medium of the invention. Various diphtheria toxin-producing *C. diphtheriae* strains can be used in practicing the invention. *C. diphtheriae* strain Park-Williams no. 8 (PW8), which produces exceptionally large amounts of diphtheria toxin, is typically used in vaccine production to obtain diphtheria toxin [15]. This strain is particularly suitable for achieving high yields of diphtheria toxin when using the fermentation medium of the invention.

In a preferred embodiment, the process for growing *C. diphtheriae* comprises inoculating a fermentation medium of the invention with a working seed that is free of animal-derived components and has been prepared without the use of animal-derived components. In the most preferred embodiment, the entire process from creating a master seed bank to growing *C. diphtheriae* in a fermentation medium, via to preparation of a working seed, is performed in the absence of animal-derived components. In another embodiment, the master seed bank and the working seed have been produced by a traditional process using a fermentation medium comprising animal-derived components, but fermentation of *C. diphtheriae* is performed in medium free from animal-derived components.

*C. diphtheriae* is cultured in aerobic conditions. Sufficient aeration is important to achieve high growth rates. Sufficient aeration is achieved e.g., by agitation at 580 to 620 rpm in a 300 L vortex fermenter. Pressurized air may be added to the fermenter at a rate of 60 L/min. An antifoam agent such as an active silicone polymer (e.g., antifoam A) may be added to prevent foam-formation due to agitation.

Industrial fermentation of *C. diphtheriae* in the past did not achieve high yields of diphtheria toxin when a fermentation medium free of animal-derived components was used. Reference 5 discloses that growing *C. diphtheriae* in 100 mL of a fermentation medium free of animal-derived components, comprising yeast extract as the nitrogen source, yielded only 60 Lf/mL of diphtheria toxin. Reference 6 grew *C. diphtheriae* in 240 L of a fermentation medium free of animal-derived components comprising yeast extract and all 20 essential amino acids as nitrogen source and yielded only maximally 100 Lf/mL of diphtheria toxin. In reference 7, 200 mL of a fermentation medium free of animal-derived components and comprising rice-wheat peptone as the main nitrogen source yielded no more than 118 Lf/mL of diphtheria toxin. When yeast extract was used in place of the rice-wheat peptone, the concentration was even lower at 59 Lf/mL.

In contrast, fermentation media of the present invention are particularly suitable for growing *C. diphtheriae* to achieve a concentration of diphtheria toxin (or derivative) of at least 140 Lf/mL. Routinely, toxin concentrations of at least 200 Lf/mL can be achieved. Typical yields are in the range between 200 Lf/mL and 250 Lf/mL. In certain embodiment, the concentration of the diphtheria toxin or the derivative in the fermentation medium exceeds 200 Lf/mL and is equal to or greater than 250 Lf/mL.

Accordingly, in one aspect, the invention also relates to a process for high-yield, industrial scale production of diphtheria toxin or a derivative thereof. Such a process comprises culturing a strain of *C. diphtheriae* in 100 L or more of a fermentation medium free of animal-derived components, growing the culture to provide a toxin (or derivative) concentration of at least 140 Lf/ml in the fermentation medium, and separating the diphtheria toxin or the derivative from the fermentation medium. In a preferred embodiment, such a process is used to prepare a diphtheria toxin suitable for use in human vaccine production. In another embodiment, the process is used to prepare a derivative of a diphtheria toxin e.g., a mutant diphtheria toxin such as CRM197.

In certain embodiments, volumes of at least 100 L of fermentation medium are used with the invention. For instance, the volume of fermentation medium can be at least 200 L, at least 250 L, at least 300 L, at least 500 L, or at least 600 L. These industrial-scale volumes are suitable for human vaccine production.

In a particular embodiment, the process of the invention yields a concentration of at least 140 Lf/mL of diphtheria toxin or the derivative in the fermentation medium. For instance, a process of the invention can yield a concentration of at least 150 Lf/mL, of at least 200 Lf/mL, or of at least 250 Lf/mL of diphtheria toxin or the derivative in the fermentation medium.

In a particular embodiment, the invention relates to a process for preparing diphtheria toxin or a derivative thereof comprising growing a strain of *Corynebacterium diphtheriae* expressing a diphtheria toxin or a derivative thereof in the fermentation medium of the invention and separating the diphtheria toxin or the derivative from the fermentation medium.

In one embodiment, separation of the bacteria from the fermentation medium containing the diphtheria toxin or the derivative may be achieved by centrifugation. In another embodiment, separation of the bacteria from the fermentation medium containing the diphtheria toxin or the derivative is achieved by filtration. For example, the fermentation medium containing the diphtheria toxin or the derivative may be sterilized by means of filtration. In some embodiments, centrifugation and filtration are both applied in combination to separate the bacteria from the fermentation medium containing the diphtheria toxin or the derivative. In a particular embodiment, separation by centrifugation takes place prior to filter-sterilization of the fermentation medium containing the diphtheria toxin or the derivative. In one embodiment, the filter used for filter-sterilization is not capable of shedding fibres. In another embodiment, the filter used for filter-sterilization comprises a membrane with a pore-size equal to or less than 0.22 nm. In a further embodiment, a preservative other than phenol is added to the filter-sterilized fermentation medium containing the diphtheria toxin or the derivative. In a preferred embodiment, no preservative is added to the filter-sterilized fermentation medium containing the diphtheria toxin or the derivative.

Toxin Purification

In a specific aspect of the invention, the diphtheria toxin used to prepare a diphtheria toxoid is purified prior to the detoxification step. Purifying the diphtheria toxin prior to toxoiding reduces cross-linking of components derived from the fermentation medium (e.g., proteins and/or peptides) to the diphtheria toxin during detoxification. Cross-linking of medium components is disadvantageous because it leads to a less homogenous product, which may lead to problems during quality control, and it also has the potential to trap allergens in the toxoid. Purification of the diphtheria toxin prior to detoxification reduces or avoids these disadvantages. The avoidance of animal-derived components in a culture medium, combined with pre-detoxification purification, gives a potent toxoid of very high purity. Even where pre-detoxification purification has been used [10], residual animal-derived components from the *C. diphtheriae* culture medium will still become covalently cross-linked to the toxin during toxoiding, even though such cross-linked materials might not be readily detectable by routine analytical assays.

In one embodiment of the invention, the diphtheria toxin used for preparing the diphtheria toxoid is at least 85% pure. In a specific embodiment, the diphtheria toxin used for preparing the diphtheria toxoid is at least 90% pure. In another specific embodiment, the diphtheria toxin used for preparing the diphtheria toxoid is at least 95% pure.

In one embodiment, the diphtheria toxin used for preparing the diphtheria toxoid according to the invention has a purity of greater than 1500 Lf/mg nitrogen. In a specific embodiment, the diphtheria toxin used for preparing the diphtheria toxoid has a purity of at least 2000 Lf/mg nitrogen. In another specific embodiment, the diphtheria toxin used for preparing the diphtheria toxoid has a purity of at least 2100 Lf/mg nitrogen. In a further specific embodiment, the diphtheria toxin used for preparing the diphtheria toxoid has a purity of at least 2700 Lf/mg nitrogen.

The diphtheria toxin or the derivative may be purified from the fermentation medium in a number of ways known to the skilled person. In one embodiment, purification is performed by a method comprising ammonium sulphate precipitation. In a particular embodiment, purification of the diphtheria toxin or derivative from the fermentation medium is performed by a method comprising anion exchange chromatography, ideally without any further downstream chromatography steps. In a further embodiment, the purification process includes one or more ultrafiltration steps.

In a further embodiment, the purified bulk diphtheria toxin obtained after purification is filter-sterilized and concentrated by means of diafiltration. These steps make it possible to store the purified bulk diphtheria toxin prior to detoxification without degradation due to microbial contamination and loss in activity. Concentrating the bulk has the additional advantage that less cold storage space is needed resulting in energy savings.

Diphtheria Toxin and Derivatives Thereof.

The invention is defined herein by reference to "diphtheria toxin or a derivative thereof". Such derivatives are those which are immunologically cross-reactive with diphtheria toxin i.e. when administered to a guinea pig, the derivative elicits antibodies which cross-react with diphtheria toxin. Many such derivatives are known in the art and are often referred to as numbered "CRM" proteins (cross-reacting material) e.g. CRM9, CRM45, CRM102, CRM103, CRM107 [8]. Typically such derivatives are diphtheria toxin mutants which differ from the wild-type toxin by only a few (e.g. 1, 2, 3, 4, or 5) amino acid mutations (single amino acid insertions, substitutions, or deletions), but truncation mutants (e.g. CRM45) are also known. These mutations can be in the A and/or B subunit of the mature toxin (the A subunit is responsible for the toxin's enzymatic activity, whereas the B subunit is responsible for binding to target host cells).

Where the invention involves a diphtheria toxin derivative, the preferred derivative is CRM197 [16,17] in which a the wild-type residue Gly-52 in the A subunit is substituted by glutamate, leading to a loss of the toxin's NAD:EF2 ADP-ribosyltransferase activity. In preferred embodiments, however, the invention is used for production of diphtheria toxin (which may subsequently be toxoided) rather than for production of diphtheria toxin derivatives, so the references to derivatives of diphtheria toxin would be ignored.

Detoxification

In one aspect the invention relates to a process for detoxifying a diphtheria toxin to prepare a diphtheria toxoid. In one embodiment, the invention relates to a process for preparing a diphtheria toxoid, wherein the process comprises (i) growing a culture of a strain of *C. diphtheriae* expressing a diphtheria toxin in a fermentation medium that is free of animal-derived components, (ii) purifying the diphtheria toxin from the fermentation medium to obtain a purified diphtheria toxin, (iii) adding a suitable detoxifying agent (preferably formaldehyde) to the purified diphtheria toxin, and (iv) incubating the purified diphtheria toxin in the presence of the detoxifying agent (preferably formaldehyde) to obtain the diphtheria toxoid.

Non-toxic derivatives of diphtheria toxin (e.g. CRM197) can also be subjected to "detoxification" although in such circumstances the purpose of cross-linking with a suitable detoxifying agent (preferably formaldehyde) is generally to stabilise the protein rather than to remove toxic activity.

In one embodiment, the fermentation medium comprises yeast extract. In a specific embodiment, the yeast extract is the only source of all essential amino acids. In a further specific embodiment, the fermentation medium is a fermentation medium of the invention.

The invention also relates to a process for preparing a diphtheria toxoid comprising the steps of (i) growing a strain of *C. diphtheriae* expressing a diphtheria toxin or a derivative thereof in a fermentation medium, (ii) separating the diphtheria toxin or the derivative from the fermentation medium to obtain a diphtheria toxin solution, (iii) preparing a diphtheria toxin concentrate from the diphtheria toxin solution, (iv) adding to the concentrate an amine and a suitable detoxifying agent (preferably formaldehyde), and (v) incubating the concentrate in the presence of the amine and the detoxifying agent to obtain the diphtheria toxoid.

Toxin Concentration

The concentration of the diphtheria toxin or derivative during detoxification is of particular importance in providing a streamlined and efficient industrial process to provide large amounts of diphtheria toxoid for vaccine production. For safety reasons, detoxification is generally performed over a six-week period. Thus, having large volumes during detoxification requires additional storage space. In addition, detoxification is performed at 36±2° C. in an incubator. Hence, using smaller volumes drastically reduces the energy used during the detoxification process. The higher the concentration of the diphtheria toxin or the derivative is during the detoxification step, the smaller is the volume that may be used for detoxification. A 20-fold reduction in volume due to concentration means that the diphtheria toxin or derivative from a 300 L incubator can easily be treated in a 20 L bottle. Thus, the purified bulk diphtheria toxin obtained after purification is preferably concentrated prior to detoxification.

In one embodiment, the concentration of the diphtheria toxin or the derivative in the concentrate is at least 20-fold higher than the concentration of the diphtheria toxin or derivative in the final fermentation medium. In another embodiment, the concentration is at least 25-fold higher e.g. at least 30-fold higher, or at least 35-fold higher.

Typically, the concentration of the diphtheria toxin or its derivative in the concentrate will be in the range between 2000 Lf/ml and 5000 Lf/ml. In a specific embodiment, the concentration of the diphtheria toxin or the derivative in the concentrate that is detoxified is at least 2000 Lf/mL. In a further specific embodiment, the concentration is at least 3000 Lf/mL. In a particular embodiment, the concentration is at least 5000 Lf/mL. These concentrations can be achieved by concentrating the diphtheria toxin solution obtained after purification from a *Corynebacterium diphtheriae* culture using e.g. ultrafiltration or other processes known in the art.

In a preferred embodiment, the starting material of the detoxification process (i.e., the diphtheria toxin or derivative thereof) is obtained by growing a culture of a strain of *Corynebacterium diphtheriae* expressing a diphtheria toxin in a fermentation medium which is free from animal-derived components e.g. which comprises yeast extract (such as the fermentation medium of the invention). In a further preferred embodiment, the diphtheria toxin is prepared using a fermentation medium that is also free of plant-derived components.

Amine Concentration

The inclusion of an amine during detoxification with a suitable detoxifying agent such as formaldehyde can prevent the cross-linking of diphtheria toxin to give multimeric complexes. However, high concentrations of an amine generally require higher concentrations of the detoxifying agent. Due to the toxicity of detoxifying agents such as formaldehyde, lower concentrations of an amine during toxoiding are therefore preferred as this results in the use of less detoxifying agent and therefore the production of smaller amounts of toxic waste during vaccine production.

In one embodiment, the concentration of the amine added during detoxification is no more than 0.1 M. In another embodiment, the concentration is no more than 0.05 M. In a further embodiment, the concentration is no more than 0.025 M. In a particular embodiment, the concentration of the amine used for detoxification is in the range of 0.025 M and 0.1 M. In a specific embodiment, the concentration is about 0.025 M.

In a particular embodiment, the amine is aliphatic diamine with a molecular weight below 200 Daltons containing primary or secondary amino groups. For example, an amino acid such as glycine, alanine, arginine or lysine may be used. Preferably, the amino acid has two basic amino groups. Most preferably, the amino acid is lysine. Lysine is particularly suitable for preparing a diphtheria toxoid having an isoelectric point in the range of 4.0 to 5.0.

Generally, the use of naturally occurring amines such as amino acids is preferred because of their greater biocompatibility and the reduced risk of adverse reactions when they form part of a vaccine. Alternatively, an amine such as ethylenediamine may be used in practicing the invention.

It was found that using 0.025 M lysine in combination with 1% formalin (40% (v/v) formaldehyde) reduces the formation of multimeric complexes and results in a particularly preferred diphtheria toxoid composition in which the vast majority of the diphtheria toxoid is present in monomeric form.

Detoxifying agents To prevent adverse reactions during vaccination due to the toxicity of diphtheria toxin, toxicity is destroyed e.g. by incubating the diphtheria toxin concentrate in the presence of a suitable detoxifying agent. If too high concentrations of a detoxifying agent are used, the final vaccine prepared with the bulk diphtheria toxoid may contain levels of the detoxifying agent which are unacceptable for human use. Thus, only certain ranges in the concentration of the detoxifying agent may be acceptable to prepare a bulk diphtheria toxoid suitable for use in manufacturing a human vaccine.

Any agent that leads to the inactivation of microorganisms such as viruses and bacteria may also be suitable for the detoxification of proteins. As a rule of thumb, the concentration of the agent for detoxification of a protein is about 10 to 20-fold higher than the agent's concentration used for the inactivation of e.g. a virus. For example, if 0.05% formalin (40% (v/v) formaldehyde) is sufficient to inactivate a virus, 1% formalin is required for detoxification of a protein by formaldehyde treatment. In addition, the temperature used for detoxification may be higher than the temperature used for inactivating a virus. However, agents, concentrations and temperatures that lead to the denaturation of proteins and hence a reduction or loss of immunogenicity of protein antigens are not suitable for the preparation of diphtheria toxoids used in human vaccination.

Suitable detoxifying agents include formaldehyde, alkylating agents such as glutaraldehyde and β-propiolactone (BPL), and peroxides including hydroperoxides. Particularly suitable multifunctional organic peroxides are described in reference 18. The use of BPL as a detoxifying agent is described in more detail in reference 19.

Treatment of diphtheria toxin with formaldehyde, glutaraldehyde, β-propiolactone (BPL) and peroxides such as hydroperoxides results in the formation of intramolecular bonds. These bonds are formed when amino acid side chains within the diphtheria toxin are cross-linked with each other Amines present during detoxification as well as residual components from the fermentation medium are also cross-linked to diphtheria toxin in the presence of the detoxifying agent. Thus, particularly suitable and hence preferred detoxifying agents are also cross-linking agents.

In one embodiment, the concentration of a suitable detoxifying agent (preferably formalin) during detoxification is in the range of 0.5% and 1%. In another embodiment, the concentration is in the range of 0.75% and 1%. In a specific embodiment, the final concentration of the detoxifying agent is about 1%.

The use of formaldehyde as detoxifying agent is preferred. It has been found that a final concentration of 0.5-1% formalin (i.e. 40% (v/v) formaldehyde) is sufficient to destroy the toxicity of the diphtheria toxin at concentrations of at least 2000 Lf/mL. Even at concentrations of 5000 Lf/mL diphtheria toxin, no retoxification was observed after 6 weeks storage at 37° C. when 1% formalin was used for detoxification.

Based on these findings, amine concentrations per Lf of diphtheria toxin and formaldehyde concentrations per Lf of diphtheria toxin can be calculated. In a more specific embodiment, the invention therefore relates to a process for preparing a diphtheria toxoid comprising preparing a solution of a diphtheria toxin at a concentration of at least 2000 Lf/mL; adding to the solution no more than 5 nmol of an amine per Lf of the diphtheria toxin and between 12 and 55 nmol, preferably between 18 and 25 nmol, formaldehyde per Lf of the diphtheria toxin; and incubating the resulting solution to obtain the diphtheria toxoid. Typically, the concentration of the diphtheria toxin or its derivative in the solution is in the range between 2000 Lf/mL and 5000 Lf/mL. In a specific embodiment, the diphtheria toxin concentration in the solution is 5000 Lf/mL. The amine is preferably lysine.

Formaldehyde for detoxification is typically used in the form of formalin i.e. as an aqueous solution. Formalin typically is a saturated aqueous solution containing about 40% (v/v) formaldehyde. Formalin can also include small amounts of stabilizers, such as methanol, to limit oxidation and polymerization.

If formaldehyde is used as detoxifying agent, the diphtheria toxoid solution resulting from detoxification process of the invention comprises no more than 0.2 g/L free formaldehyde (i.e. formaldehyde in solution that has not formed cross-links with proteins). For example, the diphtheria toxoid solution resulting from the detoxification process of the invention may comprise between 0.1 and 0.15 g/L free formaldehyde.

Further Processing Steps

A process for preparing a diphtheria toxoid in accordance with the invention may further comprise one or more filter-sterilization step(s). In one embodiment, the diphtheria toxin concentrate used for detoxification is filter-sterilized prior to the addition of a suitable detoxifying agent (preferably formaldehyde). In another embodiment, the diphtheria toxoid resulting from the detoxification process of the invention is filter-sterilized. In a further embodiment, both the diphtheria toxin concentrate and the diphtheria toxoid are filter-sterilized. Applying one or more filter-sterilization step(s) during preparation of the diphtheria toxoid has the advantage that the use of a preservative to prevent contaminating bacterial growth may be avoided. The avoidance of a preservative may prevent adverse reactions caused by the preservative when a vaccine comprising the diphtheria toxoid of the invention is administered to a human. If a preservative is added to the diphtheria toxoid for storage, a preservative other than phenol is preferred. In a preferred embodiment, no preservative is added to the diphtheria toxoid.

In one embodiment, the process for preparing the diphtheria toxoid may further comprise a particle filtration step.

In another embodiment, the process may further comprise a step for concentrating the diphtheria toxoid for storage. High protein concentration during storage is preferred as it results in less degradation of the bulk diphtheria toxoid than if the bulk diphtheria toxoid is stored in diluted form. In a specific embodiment, concentration is done by diafiltration. In a particular embodiment, the final concentration of the diphtheria toxoid for storage is 10,000 Lf/mL. Thus the invention also provides a method for storing diphtheria toxoid in concentrated aqueous form (e.g. for a period of at least 1 week, at least 1 month, or at least 3 months) wherein the concentration of diphtheria toxoid is at least 5,000 Lf/ml e.g. at least 7,500 Lf/ml, at least 10,000 Lf/ml, etc.

In some embodiments, the process for preparing the diphtheria toxoid further comprises a step in which pH of the resulting diphtheria toxoid solution is adjusted to between 6.0 and 8.0. At this pH, the diphtheria toxoid is stable and suitable for administration to a human. In a specific embodiment, the pH of the final diphtheria toxoid solution is adjusted to 7.2-7.8. In a more specific embodiment, the pH of the final diphtheria toxoid solution is adjusted to 7.5.

Diphtheria Toxoid Compositions

Employing a process for detoxifying a diphtheria toxin or derivative disclosed herein results in the provision of a diphtheria toxoid that is of higher purity than toxoids prepared in the prior art. In particular, the diphtheria toxoid produced by the methods of the invention is free from crosslinked animal-derived components. Avoidance of animal-derived components in the fermentation medium and in the detoxification procedure means that the final material is absolutely free from animal-derived components, so that no such components can become covalently cross-linked to the toxin during toxoiding, whereas prior art toxoids produced after growth in media containing animal-derived components will inevitably contain cross-linked animal-derived components, even though these might not be readily detectable by routine analytical assays. Thus these toxoids of the invention are advantageous because they have a homogeneous composition which is free of materials such as prions etc.

In some embodiments, the fermentation medium used in the production of diphtheria toxin, in addition to being free of animal-derived components, also does not comprise plant-derived components, e.g. a plant peptone. Using fermentation medium free of plant-derived components has the additional advantage that no adventitious viruses are introduced which may be present on the surface of plant material that is used to prepare a plant-derived peptone. Thus, in a specific embodiment of the invention, the diphtheria toxoid is free of both animal-derived and plant-derived components.

In a specific embodiment, a process for detoxifying a diphtheria toxin or derivative yields a diphtheria toxoid that is at least 90% pure (i.e. diphtheria toxoid is at least 90% by mass of the protein in the purified material e.g. as assessed by peak areas in HPLC analysis). In further specific embodiment, a process for detoxifying a diphtheria toxin or derivative disclosed herein yields a diphtheria toxoid that is at least 95% pure. In another specific embodiment, a process for detoxifying a diphtheria toxin or derivative disclosed herein results in a diphtheria toxin that contains yeast components in trace amounts insufficient to cause an allergic reaction.

In another embodiment, a process for detoxifying a diphtheria toxin or derivative yields a diphtheria toxoid with greater than 1500 Lf/mg nitrogen. Thus a preferred diphtheria toxoid solution resulting from the detoxification process of the invention can comprise greater than 1500 Lf/mg nitrogen. In a particular embodiment, the diphtheria toxoid solution resulting from the detoxification process of the invention comprises greater than 2000 Lf/mg nitrogen. In a specific embodiment, the diphtheria toxoid solution resulting from the detoxification process of the invention comprises greater than 2100 Lf/mg nitrogen. In a further specific embodiment, the diphtheria toxoid solution resulting from detoxification process of the invention comprises greater than 2700 Lf/mg nitrogen.

The invention also relates to combinations of any of the processes described therein. For example, the process for preparing diphtheria toxin or a derivative thereof comprising culturing a strain of *C. diphtheriae* in the fermentation medium of the invention may be combined with a process for preparing a diphtheria toxoid disclosed herein. Combining these processes is particularly advantageous since it results in a very high-yield industrial production process for providing a highly purified, defined diphtheria toxoid without the need for employing any animal-derived components in the process.

The processes of the invention yield a composition that is suitable for the manufacture of a human vaccine, has a volume of at least 5 L, and comprises cross-linked diphtheria toxoid free from animal-derived components which has a specific purity of at least 1500 Lf/mg protein nitrogen. In some embodiments, such a bulk composition has a diphtheria toxoid concentration greater than 500 Lf/mL (e.g. ≥1000 Lf/mL, ≥2000 Lf/mL, ≥3000 Lf/mL, ≥4000 Lf/mL, ≥5000 Lf/mL). A typical diphtheria toxoid concentration in the bulk composition is in the range of 2000 Lf/mL to 5000 Lf/mL. In other embodiments, such a bulk composition has a potency of greater than 2000 IU/mL (e.g. ≥3000 IU/mL, ≥5000 IU/mL, ≥8000 IU/mL, ≥10,000 IU/mL). Bulk compositions may range in volume between 5 L and 2000 L, preferably between 100-1000 L. Typical bulk volumes are e.g. 50 L, 100 L, 500 L, and 1000 L. The large volumes of the highly concentrated and potent diphtheria toxoid bulk with the specified level of purity distinguish the present invention from any of the prior art processes, which did not yield compositions suitable for the manufacture of a human vaccine at the volumes, concentration, potency and level of purity achievable by the processes of the present invention.

In a further aspect, the invention relates to a diphtheria toxoid, wherein the diphtheria toxoid has a monomer:dimer ratio in the range of 3:1 to 8:1 and an isoelectric point in the range of 4.0 to 5.0. In one embodiment, the diphtheria toxin of the invention comprises yeast components in trace amounts insufficient to cause an allergic reaction, but in another embodiment, the diphtheria toxoid of the invention is essentially free from both animal-derived components and from yeast components. In a particular embodiment, the diphtheria toxoid of the invention is free from animal-derived components. Preferably, the diphtheria toxoid is free of detectable amounts of residual free (i.e. non-crosslinked) detoxifying agent. In some instances, residual amounts of free detoxifying agent may be present. For example, the diphtheria toxoid of the invention may comprise less than 0.001 g/L free formaldehyde. Preferably, the diphtheria toxoid of the invention comprises less than 0.0001 g/L free formaldehyde.

In one embodiment, compositions of the invention comprise a diphtheria toxoid in both monomeric and dimeric form, wherein at least 80% of the diphtheria toxoid is in monomeric form and wherein the composition is free from animal-derived components.

In one aspect, the invention relates to a composition suitable as a vaccine for human use comprising a diphtheria toxoid free of crosslinked animal-derived components, wherein said composition has a potency of at least 30 IU per unit dose. In one specific embodiment, a composition of the invention has a monomer:dimer ratio of the diphtheria toxoid in the range of 3:1 to 8:1 and wherein the diphtheria toxoid comprised in the composition has an isoelectric point in the range of 4.0 to 5.0. In another specific embodiment, a composition of the invention comprises the diphtheria toxoid both in monomeric and dimeric form and wherein at least 70% of the diphtheria toxoid is in monomeric form. In some embodiments, a composition of the invention comprises at least one protective antigen from a pathogen other than *Corynebacterium diphtheriae*. The protective antigen may be selected from hepatitis B virus surface antigen, tetanus antigen, pertussis antigen, Hib antigen, meningococcal antigen, pneumococcal antigen, and IPV antigen.

Vaccine Formulations

The invention also encompasses vaccine compositions which comprise a diphtheria toxoid of the invention, or which are made by a process using a diphtheria toxoid of the invention. In these compositions, the potency of the diphtheria toxoid should be at least 20 IU per single unit dose. In a typical composition, the potency of the diphtheria toxoid is at least 25 IU/dose e.g. at least 50 IU/ml. The vaccine compositions of the invention are particularly suitable for administration to patients who previously have shown an adverse reaction to a vaccine composition including diphtheria toxoid prepared from medium comprising animal-derived components. The vaccine compositions of the invention are also suitable for the administration to patients who are at risk of developing an adverse allergic reaction. This includes patients who have been diagnosed with allergies to animal-derived components, e.g. patients with beef allergy or cow's milk allergy.

These vaccine compositions will generally be combination vaccines, i.e. including at least one protective antigen from a pathogen other than *C. diphtheriae*. A process for making a combination vaccine in accordance with the invention typically comprises mixing cross-linked diphtheria toxoid, which is free from animal-derived components and has a specific purity of at least 1500 Lf/mg protein nitrogen, with a protective antigen from at least one pathogen other than *Corynebacterium diphtheria*. Typically, both the diphtheria toxoid bulk and the bulk vaccine comprising the protective antigen are present as aqueous solutions prior to mixing. Bulk diphtheria toxoid compositions containing a high concentration of diphtheria toxoid may require dilution in an aqueous component such as water or buffer before being combined with further protective antigens. Single unit doses are prepared by dividing the final mixture of diphtheria toxoid and at least one protective antigen into single dose vials.

For example, a process for preparing at least 1000 single unit doses of a combination vaccine may comprise mixing cross-linked diphtheria toxoid, which is free from animal-derived components and has a specific purity of at least 1500 Lf/mg protein nitrogen with a protective antigen from at least one pathogen other than *Corynebacterium diphtheriae* to obtain the combination vaccine and dividing the combination vaccine into at least 1000 single unit doses, whereby care is taken that each single unit dose obtained in this way includes at least 20 IU of diphtheria toxoid and is suitable for human injection.

The invention also provides a process for preparing a combination vaccine in unit dose form, comprising the steps of: mixing bulk diphtheria toxoid with bulk of one or more further non-diphtheria antigen(s) (e.g. antigens for tetanus, pertussis, hepatitis B virus, IPV, etc., as discussed above), to give a bulk combination vaccine; and preparing at least 1000 unit doses (e.g. >10,000, >50,000, etc.) of the combination vaccine from the bulk combination vaccine; wherein (a) each unit dose is suitable for human injection and includes at least 20 IU of the diphtheria toxoid; and (b) the bulk diphtheria toxoid comprises cross-linked diphtheria toxoid, which is free from animal-derived components, has a specific purity of at least 1500 Lf/mg protein nitrogen, and has a potency of at least 2000 IU/ml. The step of mixing the bulk diphtheria toxoid with bulks of other antigen(s) can also include mixing with an aqueous diluent to provide material having the desired antigen concentrations.

The additional protective antigen(s) can be viral and/or bacterial. Typical bacterial pathogens include, but are not limited to: *Clostridium tetani; Bordetella pertussis; Haemophilus influenzae* type b; *Neisseria meningitidis*, including serogroups A, B, C, W135 and/or Y; and *Streptococcus pneumoniae*, including serotypes 6B, 14, 19F, and 23F. Typical viral pathogens include, but are not limited to: poliovirus; hepatitis A virus; measles virus; mumps virus; rubella virus; and varicella zoster virus.

Tetanus

*Clostridium tetani* causes tetanus. Tetanus toxin can be treated to give a protective toxoid. The toxoids are used in tetanus vaccines, and are disclosed in more detail in chapter 27 of reference 1. Thus a combination vaccine of the invention can include a tetanus toxoid. Preferred tetanus toxoids are those prepared by formaldehyde treatment. The tetanus toxoid can be obtained by growing *C. tetani* in growth medium (e.g. a Latham medium derived from bovine casein), followed by formaldehyde treatment, ultrafiltration and precipitation. The material may then be treated by a process comprising sterile filtration and/or dialysis.

Quantities of tetanus toxoid can be expressed in 'Lf' units (see below), defined as the amount of toxoid which, when mixed with one International Unit of antitoxin, produces an optimally flocculating mixture [74]. The NIBSC supplies 'The 1st International Reference Reagent for Tetanus Toxoid For Flocculation Test' [20] which contains 1000 Lf per ampoule, by which measurements can be calibrated.

The immunizing potency of tetanus toxoid is measured in international units (IU), assessed by comparing the protection afforded by a composition in laboratory animals (typically guinea pigs) with a reference vaccine e.g. using NIBSC's 'Tetanus Toxoid Adsorbed Third International Standard 2000' [21,22], which contains 469 IU per ampoule. The potency of tetanus toxoid in a composition of the invention should be at least 35 IU per dose e.g. at least 70 IU/ml.

Pertussis

*Bordetella pertussis* causes whooping cough. Pertussis antigens in vaccines are either cellular (whole cell, in the form of inactivated *B. pertussis* cells; 'wP') or acellular ('aP'). Thus a combination vaccine of the invention can include a cellular pertussis antigen or an acellular pertussis antigen.

Preparation of cellular pertussis antigens is well documented (e.g. see chapter 21 of reference 1) e.g. it may be obtained by heat inactivation of phase I culture of *B. pertussis*. Where acellular antigens are used, one, two or (preferably) three of the following antigens are included: (1) detoxified pertussis toxin (pertussis toxoid, or 'PT'); (2) filamentous hemagglutinin ('FHA'); (3) pertactin (also known as the '69 kiloDalton outer membrane protein'). These three antigens are preferably prepared by isolation from *B. pertussis* culture grown in modified Stainer-Scholte liquid medium. PT and FHA can be isolated from the fermentation broth (e.g. by adsorption on hydroxyapatite gel), whereas pertactin can be extracted from the cells by heat treatment and flocculation (e.g. using barium chloride). The antigens can be purified in successive chromatographic and/or precipitation steps. PT and FHA can be purified by hydrophobic chromatography, affinity chromatography and size exclusion chromatography. Pertactin can be purified by ion exchange chromatography, hydrophobic chromatography and size exclusion chromatography. FHA and pertactin may be treated with formaldehyde prior to use according to the invention. PT is preferably detoxified by treatment with formaldehyde and/or glutaraldehyde. As an alternative to this chemical detoxification procedure the PT may be a mutant PT in which enzymatic activity has been reduced by mutagenesis [23], but detoxification by chemical treatment is more usual.

Quantities of wP antigens can be expressed in international units (IU). For example, the NIBSC supplies the 'Third International Standard For Pertussis Vaccine' [24], which contains 46 IU per ampoule. Each ampoule contains the freeze-dried residue of 2.0 ml aliquots of an aqueous solution which contained 10 liters of bacterial suspension (equivalent to 180 opacity units in terms of the U.S. Opacity Standard) diluted with eight liters of M/15 Sorensen's buffer pH 7.0. As an alternative to the IU system, the 'OU' unit ("opacity units") is also used (e.g. 4 OU may be about 1 IU). The concentration of wP antigen in a composition of the invention is typically at least 8 IU/ml e.g. 4 IU/dose.

Quantities of aP antigens are typically expressed in μg. The concentration of PT in a vaccine is typically 5 μg/ml, 16 μg/ml, 20 μg/ml or 50 μg/ml. The concentration of FHA in a vaccine is typically 10 μg/ml, 16 μg/ml or 50 μg/ml. The concentration of pertactin in a vaccine is typically 5 μg/ml, 6 μg/ml or 16 μg/ml.

Hib

*Haemophilus influenzae* type b ('Hib') causes bacterial meningitis. Hib vaccines are typically based on the capsular saccharide antigen (e.g. chapter 14 of ref. 1), the preparation of which is well documented (e.g. references 25 to 34). The *H. influenzae* bacteria can be cultured in the absence of animal-derived components. The Hib saccharide is conjugated to a carrier protein in order to enhance its immunogenicity, especially in children. Typical carrier proteins in these conjugates are tetanus toxoid, diphtheria toxoid, the CRM197 derivative of diphtheria toxin, or an outer membrane protein complex from serogroup B meningococcus. Thus a combination vaccine of the invention can include a Hib capsular saccharide conjugated to a carrier protein.

Tetanus toxoid is the preferred carrier, as used in the product commonly referred to as 'PRP-T'. PRP-T can be made by activating a Hib capsular polysaccharide using cyanogen bromide, coupling the activated saccharide to an adipic acid linker (such as (1-ethyl-3-(3-dimethylaminopropyl) carbodiimide), typically the hydrochloride salt), and then reacting the linker-saccharide entity with a tetanus toxoid carrier protein. The saccharide moiety of the conjugate may comprise full-length polyribosylribitol phosphate (PRP) as prepared from Hib bacteria, and/or fragments of full-length PRP. Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5. In preferred vaccines, however, the weight ratio of saccharide to carrier protein is between 1:2.5 and 1:3.5. In vaccines where tetanus toxoid is present both as an antigen and as a carrier protein then the weight ratio of saccharide to carrier protein in the conjugate may be between 1:0.3 and 1:2 [35]. Administration of the Hib conjugate preferably results in an anti-PRP antibody concentration of ≥0.15 μg/ml, and more preferably ≥1 μg/ml, and these are the standard response thresholds.

Quantities of Hib antigens are typically expressed in ng of saccharide. The concentration of saccharide in a vaccine is typically between 10-30 μg/ml e.g. 20 μg/ml.

Meningococcus

*Neisseria meningitidis* causes bacterial meningitis. Based on the organism's capsular polysaccharide, various serogroups of *N. meningitidis* have been identified, including A, B, C, H, I, K, L, 29E, W135, X, Y & Z. The *N. meningitidis* bacteria can be cultured in the absence of animal-derived components. The serogroups most associated with disease are A, B, C, W135 and Y. Current vaccines against serogroups A, C, W135 and Y are based on the capsular saccharide antigens, but this approach is not suitable for serogroup B, and so protein antigens and outer-membrane vesicles are used instead [36]. The capsular saccharides are conjugated to carrier proteins in order to enhance immunogenicity. Typical carrier proteins are tetanus toxoid (as in the NIMENRIX™ product), diphtheria toxoid (as in the MENACTRA™ product), and the CRM197 derivative of diphtheria toxin (as in the MENVEO™ product). Thus a combination vaccine of the invention can include one or more (e.g. 2, 3, or 4) of capsular saccharides, conjugated to a carrier protein, selected from: (1) serogroup A *N. meningitidis*; (2) serogroup C *N. meningitidis*; (3) serogroup W135 *N. meningitidis*; and/or (4) serogroup Y *N. meningitidis*;

The saccharide moiety of the conjugate may comprise full-length saccharide as prepared from meningococci, and/or fragments thereof. Serogroup C saccharides may be prepared from either OAc+ or OAc− strains. For serogroup A saccharides, preferably at least 50% (e.g. at least 60%, 70%, 80%, 90%, 95% or more) of the mannosamine residues are O-acetylated at the C-3 position. Meningococcal conjugates with a saccharide:protein ratio (w/w) of between 1:10 (i.e. excess protein) and 10:1 (i.e. excess saccharide) may be used e.g. ratios between 1:5 and 5:1, between 1:2.5 and 2.5:1, or between 1:1.25 and 1.25:1 Administration of a conjugate preferably results in an increase in serum bactericidal assay (SBA) titre for the relevant serogroup of at least 4-fold, and preferably at least 8-fold. SBA titres can be measured using baby rabbit complement or human complement [37].

Quantities of meningococcal antigens are typically expressed in µg of saccharide. The concentration of saccharide in a vaccine is typically between 5-30 µg/ml per serogroup e.g. 10 µg/ml or 20 µg/ml.

Pneumococcus

*Streptococcus pneumoniae* causes bacterial meningitis. Like Hib and meningococcus, existing vaccines are based on capsular saccharides. The *S. pneumoniae* bacteria can be cultured in the absence of animal-derived components. Thus a combination vaccine of the invention can include a pneumococcal capsular saccharide conjugated to a carrier protein.

It is preferred to include saccharides from more than one serotype of *S. pneumoniae*, and particularly at least serotypes 6B, 14, 19F and 23F. Further serotypes are preferably selected from: 1, 3, 4, 5, 7F, 9V and 18C. For example, mixtures of polysaccharides from 23 different serotype are widely used, as are conjugate vaccines with polysaccharides from between 5 and 11 different serotypes [38]. For example, PREVNAR™ [39] contains conjugated saccharides from seven serotypes (4, 6B, 9V, 14, 18C, 19F, and 23F), and SYNFLORIX™ contains conjugated saccharides from ten serotypes (1, 4, 5, 6B, 7F, 9V, 14, 18C, 19F, 23F). Saccharides are preferably conjugated to carrier proteins [e.g. refs. 40 to 42]. Typical carrier proteins are tetanus toxoid, diphtheria toxoid, the CRM197 derivative of diphtheria toxin, and *H. influenzae* protein D. Saccharides in the PREVNAR™ product are individually conjugated to CRM197 by reductive amination, with 2 µg of each saccharide per 0.5 ml dose (4 µg of serotype 6B). SYNFLORIX™ uses three different carrier proteins and a mixture of different saccharide quantities for the different serogroups.

Quantities of pneumococcal antigens are typically expressed in µg of saccharide. The concentration of a pneumococcal conjugate, measured as saccharide, is typically between 2 and 20 µg/ml for each serotype.

Hepatitis B Virus

Hepatitis B virus (HBV) is a cause of viral hepatitis. The HBV virion consists of an inner core surrounded by an outer protein coat or capsid, and the viral core contains the viral DNA genome. The major component of the capsid is a protein known as HBV surface antigen or, more commonly, 'HBsAg', which is typically a 226-amino acid polypeptide with a molecular weight of ~24 kDa. All existing hepatitis B vaccines contain HBsAg, and when this antigen is administered to a normal vaccinee it stimulates the production of anti-HBsAg antibodies which protect against HBV infection. Thus a combination vaccine of the invention can include HBsAg.

For vaccine manufacture, HBsAg can be made in two ways. The first method involves purifying the antigen in particulate form from the plasma of chronic hepatitis B carriers, as large quantities of HBsAg are synthesized in the liver and released into the blood stream during an HBV infection. The second way involves expressing the protein by recombinant DNA methods. HBsAg for use with the method of the invention should be recombinantly expressed in yeast cells. Suitable yeasts include *Saccharomyces* (such as *S. cerevisiae*), *Hanensula* (such as *H. polymorpha*) or *Pichia* hosts. The yeasts can be cultured in the absence of animal-derived components.

Unlike native HBsAg (i.e. as in the plasma-purified product), yeast-expressed HBsAg is generally non-glycosylated, and this is the most preferred form of HBsAg for use with the invention. Yeast-expressed HBsAg is highly immunogenic and can be prepared without the risk of blood product contamination. Many methods for purifying HBsAg from recombinant yeast are known in the art.

The HBsAg will generally be in the form of substantially-spherical particles (average diameter of about 20 nm), including a lipid matrix comprising phospholipids. Yeast-expressed HBsAg particles may include phosphatidylinositol, which is not found in natural HBV virions. The particles may also include a non-toxic amount of LPS in order to stimulate the immune system [43]. The particles may retain non-ionic surfactant (e.g. polysorbate 20) if this was used during disruption of yeast [44].

The HBsAg is preferably from HBV subtype adw2.

A preferred method for HBsAg purification involves, after cell disruption: ultrafiltration; size exclusion chromatography; anion exchange chromatography; ultracentrifugation; desalting; and sterile filtration. Lysates may be precipitated after cell disruption (e.g. using a polyethylene glycol), leaving HBsAg in solution, ready for ultrafiltration.

After purification HBsAg may be subjected to dialysis (e.g. with cysteine), which can be used to remove any mercurial preservatives such as thimerosal that may have been used during HBsAg preparation [45].

Quantities of HBsAg are typically expressed in micrograms. The concentration of HBsAg in a composition of the invention is preferably less than 60 µg/ml e.g. ≤55 µg/ml, ≤50 µg/ml, ≤45 µg/ml, ≤40 µg/ml, etc. A concentration of about 20 µg/m' is typical e.g. 10 µg per dose.

Poliovirus

Poliovirus causes poliomyelitis. Inactivated polio virus vaccine (IPV), as disclosed in more detail in chapter 24 of reference 1, has been known for many years. Thus a combination vaccine of the invention can include an inactivated poliovirus antigen.

Polioviruses may be grown in cell culture, and a preferred culture uses a Vero cell line, derived from monkey kidney. Vero cells can conveniently be cultured microcarriers. After growth, virions may be purified using techniques such as ultrafiltration, diafiltration, and chromatography. Where animal (and particularly bovine) materials are used in the culture of cells, they should be obtained from sources that are free from transmissible spongiform encephalopathies (TSEs), and in particular free from bovine spongiform encephalopathy (BSE). Preferably, polioviruses are grown in cells cultured in medium free of animal-derived components.

Prior to administration to patients, polioviruses must be inactivated, and this can be achieved by treatment with formaldehyde. Poliomyelitis can be caused by one of three types of poliovirus. The three types are similar and cause identical symptoms, but they are antigenically very different and infection by one type does not protect against infection by others. It is therefore preferred to use three poliovirus antigens with the invention: poliovirus Type 1 (e.g. Mahoney strain), poliovirus Type 2 (e.g. MEF-1 strain), and poliovirus Type 3 (e.g. Saukett strain). The viruses are preferably grown, purified and inactivated individually, and are then combined to give a bulk trivalent mixture for use with the invention. Quantities of IPV are typically expressed in the 'DU' unit (the "D-antigen unit" [46]). It is preferred to use between 1-100 DU per polioviral type per dose e.g., about 40 DU of type 1 poliovirus, about 8 DU of type 2 poliovirus, and about 32 DU of type 3 poliovirus (but it is possible to use lower doses than these [47,48] e.g. 10-20 DU for type 1, 2-4 DU for type 2, and 8-20 DU for type 3.

Where an IPV component is used, and the polioviruses were grown on Vero cells, a vaccine composition preferably contains less than 10 ng/ml, preferably ≤1 ng/ml e.g. ≤500 pg/ml or ≤50 pg/ml of Vero cell DNA e.g. less than 10 ng/ml of Vero cell DNA that is ≥50 base pairs long.

Preparing a Combination Vaccine

Antigenic components from these pathogens for use in vaccines are commonly referred to by abbreviated names: 'D' for diphtheria toxoid; 'T' for tetanus toxoid; 'P' for pertussis antigens, with 'Pa' being acellular (e.g. including at least PT, FHA and pertactin) and 'Pw' being cellular; 'Hib' for conjugated $H.$ $influenzae$ b capsular saccharide; 'MenA', 'MenB', 'MenC', 'MenW' and 'MenY' for the respective meningococcal serogroups, separately conjugated to carrier proteins; 'IPV' for 3-valent inactivated poliovirus; and 'Spn' for pneumococcus.

The following combination vaccines are preferred embodiments of the invention, wherein the 'D' component is a diphtheria toxoid prepared as disclosed herein:

D, T, HBsAg
D, T, Pw, HBsAg
D, T, Pw, HBsAg, Hib
D, T, Pw, HBsAg, Hib, MenA, MenC
D, T, Pw, HBsAg, Hib, MenA, MenC, MenW135
D, T, Pw, HBsAg, Hib, MenA, MenC, MenY
D, T, Pw, HBsAg, Hib, MenA, MenC, MenW135, MenY
D, T, Pa, HBsAg
D, T, Pa, Hib
D, T, Pa, HBsAg, Hib
D, T, Pa, HBsAg, IPV
D, T, Pa, HBsAg, IPV, Hib
D, T, Pa, HBsAg, IPV, Hib, Spn
D, T, Pa, HBsAg, IPV, Hib, MenC
D, T, Pa, HBsAg, IPV, Hib, MenC, MenA
D, T, Pa, HBsAg, IPV, Hib, MenC, MenY
D, T, Pa, HBsAg, IPV, Hib, MenC, MenW135
D, T, Pa, HBsAg, IPV, Hib, MenC, MenA, MenW135, MenY

These combination vaccines may consist of the antigens listed, or may further include antigens from additional pathogens. Thus they can be used separately, or as components of further vaccines.

When combining antigenic components to prepare a multivalent composition, the antigens can be added individually, or they can be pre-mixed. Where a combination vaccine comprises D and T antigens and additional antigens, it is preferred to use a pre-mixed D-T component in the preparation of the combination vaccine. This bivalent component can be combined with further antigens. Where D, T and Pw antigens are used, it is preferred to use a pre-mixed D-T-Pw component, and then to use this component in the preparation of the combination vaccine.

Where a D-T mixture is used, the ratio of diphtheria toxoid to tetanus toxoid in the mixture is usually between 2:1 and 3:1 (measured in Lf units), preferably between 2.4:1 and 2.6:1, e.g. preferably 2.5:1.

Carrier Proteins for Conjugates

Conjugated saccharide antigens include a carrier protein, to which the saccharide is covalently attached, either directly or via a linker. General information on conjugation techniques can be found in ref. 34.

Various proteins are known for use as carriers, and preferred carrier proteins are bacterial toxoids, such as diphtheria toxoid (e.g. produced according to the invention) or tetanus toxoid. Other suitable carrier proteins include, but are not limited to, the CRM197 mutant of diphtheria toxin [49,50], the $N.$ $meningitidis$ outer membrane protein [51], synthetic peptides [52, 53], heat shock proteins [54,55], pertussis proteins [56,57], cytokines [58], lymphokines [58], hormones [58], growth factors [58], artificial proteins comprising multiple human $CD4^+$ T cell epitopes from various pathogen-derived antigens [59] such as N19 [60], protein D from $H.$ $influenzae$ [61,62], pneumococcal surface protein PspA [63], pneumolysin [64], iron-uptake proteins [65], toxin A or B from $C.$ $difficile$ [66], $S.$ $agalactiae$ proteins [67], etc.

Attachment of a saccharide to a carrier is preferably via a $-NH_2$ group e.g. in the side chain of a lysine residue in a carrier protein, or of an arginine residue. Attachment to —SH groups (e.g. in the side chain of a cysteine) is also possible.

Conjugates with a saccharide:protein ratio (w/w) of between 1:5 (i.e. excess protein) and 5:1 (i.e. excess saccharide) are preferred.

Compositions may include a small amount of free carrier. Ignoring any carrier included as a separate antigen, unconjugated carrier is preferably no more than 5% of the total amount of the carrier protein in the composition as a whole, and more preferably present at less than 2% by weight.

As in the SYNFLORIX™ product, it is possible to include more than one type of carrier protein in a composition e.g. to reduce the risk of carrier suppression.

Amounts of conjugates are generally given in terms of mass of saccharide (i.e. the dose of the conjugate as a whole (i.e. carrier+saccharide) is higher than the stated dose) in order to avoid variation due to choice of carrier.

Adjuvants

Vaccines of the invention will generally include an adjuvant. The most usual adjuvant for inclusion is an aluminium salt, such as an aluminium hydroxide and/or an aluminium phosphate. Antigens in a combination vaccine can be adsorbed (partially or totally) to aluminium salts.

The adjuvants commonly known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 $cm^{-1}$ and a strong shoulder at 3090-3100 $cm^{-1}$ (chapter 9 of ref. 68). The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants e.g. with needle-like particles with diameters about 2 nm. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

The adjuvants commonly known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a $PO_4$/Al molar ratio between 0.3 and 1.2. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls (chapter 9 of ref. 68). The $PO_4/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4$/Al molar ratio between 0.84 and 0.92, included at 0.6 mg $Al^{3+}$/ml. The aluminium phosphate will generally be particulate (e.g. plate-like morphology as seen in transmission electron micrographs, with primary particles in the range of 50 nm). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The PZC of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range of $Al^{+++}$ in a composition of the invention is between 0.3 and 1 mg/ml or between 0.3-0.5 mg/ml. A maximum of 0.85 mg/dose is typical.

In one embodiment, diphtheria toxoid is adsorbed onto an aluminium salt adjuvant e.g. is adsorbed to an aluminium hydroxide adjuvant.

In a combination vaccine comprising a tetanus toxoid, the tetanus toxoid may be adsorbed onto an aluminium hydroxide adjuvant, but this is not necessary (e.g. adsorption of between 0-10% of the total tetanus toxoid can be used).

In a combination vaccine comprising a whole-cell pertussis antigen, the wP antigen is preferably combined with an aluminium hydroxide adjuvant and/or an aluminium phosphate adjuvant.

In a combination vaccine comprising acellular pertussis antigen(s), the pertussis antigen(s) may be adsorbed onto one or more aluminium salt adjuvants, or may be added in an unadsorbed state. Where pertactin is present in a composition then it is preferably adsorbed onto an aluminium hydroxide adjuvant before being used in the process of the invention. PT and FHA may be adsorbed onto an aluminium hydroxide adjuvant or an aluminium phosphate before being used in the process of the invention. In preferred embodiments, PT, FHA and pertactin are separately pre-adsorbed to aluminium hydroxide prior to being used in the process of the invention.

In a combination vaccine comprising Hib antigens and an aluminium salt, the Hib conjugate may be unadsorbed or can be adsorbed (e.g. adsorbed to an aluminium phosphate adjuvant [69]). Adsorption in this way is particularly useful in vaccines comprising D-T-Pw-Hib-HBsAg antigens. Other conjugated antigens (e.g. meningococcus, pneumococcus) can similarly be adsorbed to an aluminium salt (e.g. a phosphate) or can be unadsorbed [70].

IPV antigens are typically not adsorbed to any adjuvant before being used in a process of the invention, but they can become adsorbed onto aluminium adjuvant(s) originating with other components.

In a combination vaccine comprising HBsAg, the HBsAg can be adsorbed onto aluminium phosphate using the methods described in ref. 71. Adsorption to aluminium phosphate contrasts with the well-known ENGERIX-B™ product (where HBsAg is adsorbed to aluminium hydroxide). As mentioned in reference 72, aluminium phosphate can be a better adjuvant for HBsAg than aluminium hydroxide.

Where a process of the invention utilises a component in which diphtheria and tetanus toxoids have been mixed prior to their being combined with HBsAg, this D-T mixture preferably contains an aluminium hydroxide adjuvant, to which the D and T antigens are both adsorbed.

Where a process of the invention utilises a component in which diphtheria toxoid, tetanus toxoid and whole-cell pertussis antigen have been mixed prior to their being combined with HBsAg, this D-T-Pw mixture preferably contains both an aluminium hydroxide adjuvant, to which the D and T antigens are adsorbed, and an aluminium phosphate adjuvant.

When an adjuvant is included in a vaccine of the invention, it can be added at various stages. Antigens can be combined with adjuvants before being used in preparing combination vaccines (e.g. a bivalent D-T mixture can be adsorbed to aluminium salt adjuvant(s) before being used in a process of the invention), but it is also possible to add adjuvant after the antigens have been mixed, or to add a sequence of antigens to an adjuvant (e.g. to start with an aqueous adjuvant, then to add antigens, either individually or pre-mixed).

Further Non-Antigen Components

Vaccine compositions of the invention may comprise carriers, excipients, buffers, etc.

To control tonicity, a composition may include a physiological salt, such as a sodium salt. Sodium chloride (NaCl) is preferred, which may be present at between 1 and 20 mg/ml. In a specific embodiment, the sodium chloride concentration is between 8 and 9 mg/ml (e.g. about 8.5 mg/ml).

Compositions will generally have an osmolality of between 200 mOsm/kg and 400 mOsm/kg, preferably between 240-360 mOsm/kg, and will more preferably fall within the range of 280-320 mOsm/kg. Osmolality has previously been reported not to have an impact on pain caused by vaccination [73], but keeping osmolality in this range is nevertheless preferred.

Compositions of the invention may include one or more buffer(s). Typical buffers include: a phosphate buffer; a Tris buffer; a borate buffer; a succinate buffer; a histidine buffer; or a citrate buffer. Buffers will typically be included in the 5-20 mM range.

Compositions of the invention may include one or more preservative(s), but in some embodiments the compositions are preservative-free. Preferred compositions are substantially free from mercurial preservatives (e.g. thimerosal) e.g. they contain less than 0.1 µg/ml of mercury, and preferably contains no detectable mercury. This will generally be achieved by removing the mercurial preservative from an antigen preparation prior to its addition in the process of the invention or by avoiding the use of thimerosal during the preparation of the components used to make the composition. However, the presence of trace amounts of a mercurial preservative may be unavoidable if a component (particularly HBsAg) was treated with such a preservative before being used in the composition of the invention. For safety, however, it is preferred that the final composition contains less than about 25 ng/ml mercury.

In some embodiments, the composition comprising the diphtheria toxoid of the invention contains a preservative other than phenol. In one embodiment, the preservative is sodium thimerfonate. In another embodiment, the preservative is 2-phenoxyethanol (2-PE). If 2-PE is used, it is preferably present (a) between 2.5 mg and 3.5 mg (e.g. about 3 mg) for every 100 Lf of diphtheria toxoid, and/or (b) between 7 mg and 8 mg (e.g. about 7.5 mg) for every 100 Lf of tetanus toxoid. A 2-PE concentration of between 3 g/l and 8 g/l (e.g. between 4-6 g/l, or about 5 g/l) in the composition of the invention is preferred. In a particular embodiment, the composition of the invention comprises 167 Lf diphtheria toxoid; 67 Lf tetanus toxoid; 5 mg 2-PE.

A composition of the invention can be substantially free from surfactants. In particular, the composition of the invention can be substantially free from polysorbate 80 e.g. it contains less than 0.1 µg/ml of polysorbate 80, and preferably contains no detectable polysorbate 80. Where a composition includes HBsAg, however, it will usually include polysorbate 20 e.g. if it was used during yeast disruption [44].

The pH of a composition of the invention will generally be between 5.0 and 7.5, and more typically between 5.0 and 6.0 for optimum stability or, where a diphtheria toxoid and/or tetanus toxoid is present, between 6.0 and 7.0. A process of the invention may therefore include a step of adjusting the pH of the bulk vaccine prior to packaging.

Compositions of the invention are preferably non-pyrogenic e.g. containing <1 EU (endotoxin unit, a standard measure; 1 EU is equal to 0.2 ng FDA reference standard Endotoxin EC-2 'RSE') per dose, and preferably <0.1 EU per dose.

Compositions of the invention are preferably gluten free.

Compositions of the invention are preferably sterile.

Compositions of the invention are preferably in aqueous form. During manufacture, dilution of the antigens to give desired final concentrations will usually be performed with WFI (water for injection).

Residual material from individual antigenic components may also be present in trace amounts in a final vaccine composition of the invention. For example, if formaldehyde is used to prepare the toxoids of diphtheria, tetanus and pertussis then the final vaccine product may retain trace amounts of formaldehyde (e.g. less than 10 µg/ml, preferably <5 µg/ml). Media or stabilizers may have been used during poliovirus preparation (e.g. Medium 199), and these may carry through to the final vaccine Similarly, free amino acids (e.g. alanine, arginine, aspartate, cysteine and/or cystine, glutamate, glutamine, glycine, histidine, proline and/or hydroxyproline, isoleucine, leucine, lysine, methionine, phenylalanine, serine, threonine, tryptophan, tyrosine and/or valine), vitamins (e.g. choline, ascorbate, etc.), disodium phosphate, monopotassium phosphate, calcium, glucose, adenine sulfate, phenol red, sodium acetate, potassium chloride, etc. may be retained in the final vaccine at ≤100 µg/ml, preferably <10 µg/ml, each. Other components from antigen preparations, such as neomycin (e.g. neomycin sulfate, particularly from the IPV component), polymyxin B (e.g. polymyxin B sulfate, particularly from the IPV component), etc. may also be present at sub-nanogram amounts per dose. A further possible component of the final vaccine which originates in the antigen preparations arises from less-than-total purification of antigens Small amounts of *B. pertussis, C. diphtheriae, C. tetani* and *S. cerevisiae* proteins and/or genomic DNA may therefore be present. To minimize the amounts of these residual components, antigen preparations are preferably treated to remove them prior to the antigens being used in the process of the invention.

Packaging Compositions of the Invention

The invention can provide bulk material which is suitable for packaging into individual doses, which can then be distributed for administration to patients. Concentrations mentioned above are typically concentrations in final packaged dose, and so concentrations in bulk vaccine may be higher (e.g. to be reduced to final concentrations by dilution). Concentrated bulk diphtheria toxoid compositions are typically diluted in an aqueous component such as water or buffer before being combined with other materials, such as other antigens, adjuvants, etc.

Human intramuscular vaccines are generally administered as an individual dosage volume of 0.5 ml. Processes of the invention may thus comprise a step of extracting and packaging a 0.5 ml sample of the mixture into a container. References to 0.5 ml doses will be understood to include normal variance e.g. 0.5 ml±0.05 ml. For multidose situations, multiple dose amounts will be extracted and packaged together in a single container e.g. 5 ml for a 10-dose multidose container (or 5.5 ml with 10% overfill).

Processes of the invention may comprise a step of packaging the vaccine into containers for use. Suitable containers include vials and disposable syringes (preferably sterile ones).

Where a composition of the invention is packaged into vials, these are preferably made of a glass or plastic material. The vial is preferably sterilized before the composition is added to it. To avoid problems with latex-sensitive patients, vials are preferably sealed with a latex-free stopper. The vial may include a single dose of vaccine, or it may include more than one dose (a 'multidose' vial) e.g. 10 doses. When using a multidose vial, each dose should be withdrawn with a sterile needle and syringe under strict aseptic conditions, taking care to avoid contaminating the vial contents. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where the composition is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of butyl rubber. If the syringe and needle are packaged separately then the needle is preferably fitted with a butyl rubber shield. Grey butyl rubber is preferred. Preferred syringes are those marketed under the trade name "Tip-Lok"™.

Where a glass container (e.g. a syringe or a vial) is used, then it is preferred to use a container made from a borosilicate glass rather than from a soda lime glass.

After a composition is packaged into a container, the container can then be enclosed within a box for distribution e.g. inside a cardboard box, and the box will be labeled with details of the vaccine e.g. its trade name, a list of the antigens in the vaccine (e.g. 'hepatitis B recombinant', etc.), the presentation container (e.g. 'Disposable Prefilled Tip-Lok Syringes' or '10×0.5 ml Single-Dose Vials'), its dose (e.g. 'each containing one 0.5 ml dose'), warnings (e.g. 'For Adult Use Only' or 'For Pediatric Use Only'), an expiration date, an indication, a patent number, etc. Each box might contain more than one packaged vaccine e.g. five or ten packaged vaccines (particularly for vials). If the vaccine is contained in a syringe then the package may show a picture of the syringe.

The vaccine may be packaged together (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

A packaged vaccine is preferably stored at between 2° C. and 8° C. It should not be frozen.

Vaccines can be provided in full-liquid form (i.e. where all antigenic components are in aqueous solution or suspension) during manufacture, or they can be prepared in a form where some components are in liquid form and others are in a lyophilized form. Thus a final vaccine can be prepared extemporaneously at the time of use by mixing together two components: (a) a first component comprising aqueous antigens; and (b) a second component comprising lyophilized antigens. The two components are preferably in separate containers (e.g. vials and/or syringes), and the invention provides a kit comprising components (a) and (b). This format is particularly useful for vaccines that include a conjugate component, particularly Hib and/or meningococcal and/or pneumococcal conjugates, as these may be more stable in lyophilized form (whereas D, T, P and HBsAg components are preferably in liquid form). Thus conjugates may be lyophilised prior to their use with the invention. Further components may also be added prior to freeze-drying e.g. as stabilizers. Preferred stabilizers for inclusion are lactose, sucrose and mannitol, as well as mixtures thereof e.g. lactose/sucrose mixtures, sucrose/mannitol mixtures, etc. The final vaccine may thus contain lactose and/or sucrose. Using a sucrose/mannitol mixture can speed up the drying process.

Thus the invention provides a process for preparing a two-container combination vaccine, comprising the following steps:
preparing an aqueous combination vaccine as described above, but wherein the said one or more antigens does not include a conjugated capsular saccharide antigen;
packaging said aqueous combination vaccine in a first container (e.g. a syringe);
preparing a conjugated capsular saccharide antigen in lyophilised form;
packaging said lyophilised antigen in a second container (e.g. a vial); and
packaging the first container and second container together in a kit.

The kit can then be distributed to physicians.

Methods of Treatment and Administration of the Vaccine

Compositions of the invention are suitable for administration to human patients, and the invention provides a method of raising an immune response in a patient, comprising the step of administering a composition of the invention to the patient. Compositions of the invention are preferably administered to patients in 0.5 ml doses (as discussed above).

The invention also provides a composition of the invention for use in medicine. The invention also provides the use of the composition of the invention in the prevention of at least an infection with C. diphtheriae. Compositions of the invention are preferably vaccines for use in the prevention and/or treatment of at least an infection with C. diphtheriae. The compositions of the invention are particularly useful in patients with allergies against animal-derived components. For example, patients with beef allergy or cow's milk allergy may be particularly susceptible to allergic reactions in response to diphtheria toxoid prepared from medium comprising animal-derived components. Allergic reactions may only occur not occur after the first administration of such a diphtheria toxoid, but only during subsequent booster vaccination. The composition of the invention is therefore particularly useful when used for booster vaccination. Both children and adults being at risk for allergic reactions benefit from the composition of the invention.

The invention also provides the use of antigenic components as described herein (including diphtheria toxoids of the invention) for use in the manufacture of a vaccine.

In order to have full efficacy, a typical primary immunization schedule for a child may involve administering more than one dose. For example, doses may be at: 0 & 6 months (time 0 being the first dose); at 0, 1, 2 & 6 months; at day 0, day 21 and then a third dose between 6 & 12 months; at 2, 4 & 6 months; at 3, 4 & 5 months; at 6, 10 & 14 weeks; or at 0, 1, 2, 6 & 12 months.

Compositions can also be used as booster doses e.g. for children, in the second year of life.

Compositions of the invention can be administered by intramuscular injection e.g. into the arm or leg Vaccines produced by the invention may be administered to patients at the same time as a separate vaccine e.g. at the same time as a pneumococcal conjugate vaccine such as Prevnar™, at the same time as an influenza vaccine, at the same time as a rotavirus vaccine, at the same time as a MMR vaccine, etc.

Where compositions of the invention include an aluminium-based adjuvant, settling of components may occur during storage. The composition should therefore be shaken prior to administration to a patient. The shaken composition will be a turbid white suspension.

Quantitative Units for Diphtheria Toxoid Measurement

Quantities of diphtheria toxin and/or toxoid in a composition are generally measured in the 'Lf' unit ("flocculating units", or the "limes flocculating dose", or the "limit of flocculation"), defined as the amount of toxin/toxoid which, when mixed with one International Unit of antitoxin, produces an optimally flocculating mixture [74,75]. For example, the NIBSC supplies 'Diphtheria Toxoid, Plain' [76], which contains 300 Lf per ampoule, and also supplies 'The 1st International Reference Reagent For Diphtheria Toxoid For Flocculation Test' [77] which contains 900 Lf per ampoule. The concentration of diphtheria toxin or toxoid in a composition can readily be determined using a flocculation assay by comparison with a reference material calibrated against such reference reagents.

Purity of a protein preparation can be expressed by the ratio of specific protein to total protein. The purity of diphtheria toxin/toxoid in a composition is generally expressed in units of Lf diphtheria toxoid per unit mass of protein (nondialysable) nitrogen. For instance, a very pure toxin/toxoid might have a purity of more than 1700 Lf/mg N, indicating that most or all of the protein in the composition is diphtheria toxin/toxoid [78].

The immunizing potency of diphtheria toxoid in a composition is generally expressed in international units (IU). The potency can be assessed by comparing the protection afforded by a composition in laboratory animals (typically guinea pigs) with a reference vaccine that has been calibrated in IUs. NIBSC supplies the 'Diphtheria Toxoid Adsorbed Third International Standard 1999' [79,80], which contains 160 IU per ampoule, and is suitable for calibrating such assays.

A three-dilution assay can be used to determine the potency of the compositions of the invention. After immunization, the guinea-pigs are bled or challenged either by the subcutaneous or by the intradermal route. In an alternative embodiment, mice are used in place of guinea pigs. When guinea pigs or mice are bled, the antitoxin levels of the individual animals are titrated by means of toxin neutralization tests performed using in vivo or in vitro serological methods that have been validated on vaccines of the types being tested. In one embodiment, diphtheria toxoids produced in fermentation medium comprising animal-derived components are used for validation. The potency of the composition of the invention is calculated using appropriate statistical methods. For three-dilution assays, the limits of the 95% confidence intervals of the estimate of potency is within 50-200% of the estimated potency unless the lower limit of the 95% confidence interval of the estimated potency is greater than 30 IU per single human dose. In a preferred embodiment, the potency of the composition of the invention is at least 30 IU per single dose. When one-dilution tests are performed, the potency of the test vaccine is demonstrated to be significantly greater than 30 IU per human dose.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where an antigen is described as being "adsorbed" to an adjuvant, it is preferred that at least 50% (by weight) of that antigen is adsorbed e.g. 50%, 60%, 70%, 80%, 90%, 95%, 98% or more. It is preferred that diphtheria toxoid and HBsAg are both at least 90% adsorbed, and ideally are totally adsorbed i.e. none is detectable in supernatant after centrifugation.

The compositions described herein are preferably free from diphtheria toxoid which includes cross-linked animal-derived components.

DESCRIPTION OF THE DRAWINGS

FIG. 1: Flow chart of a fermentation process according to the invention

FIG. 9: Chromatogram of samples with a diphtheria toxin starting concentration of 500 Lf/mL after detoxification with 1% formalin in the absence of lysine or in the presence of 0.025 M lysine FIG. 10: Chromatogram of samples with a diphtheria toxin starting concentration of 2000 Lf/mL after detoxification with 1% formalin in the absence of lysine or in the presence of 0.025 M lysine FIG. 11: Chromatogram of samples with a diphtheria toxin starting concentration of 5000 Lf/mL after detoxification with 1% formalin in the absence of lysine or in the presence of 0.025 M lysine FIG. 12: Flow chart of a purification and detoxification process according to the invention.

MODES FOR CARRYING OUT THE INVENTION

Example 1

Preparation of Deferrated Yeast Extract Solution

Figure 2:
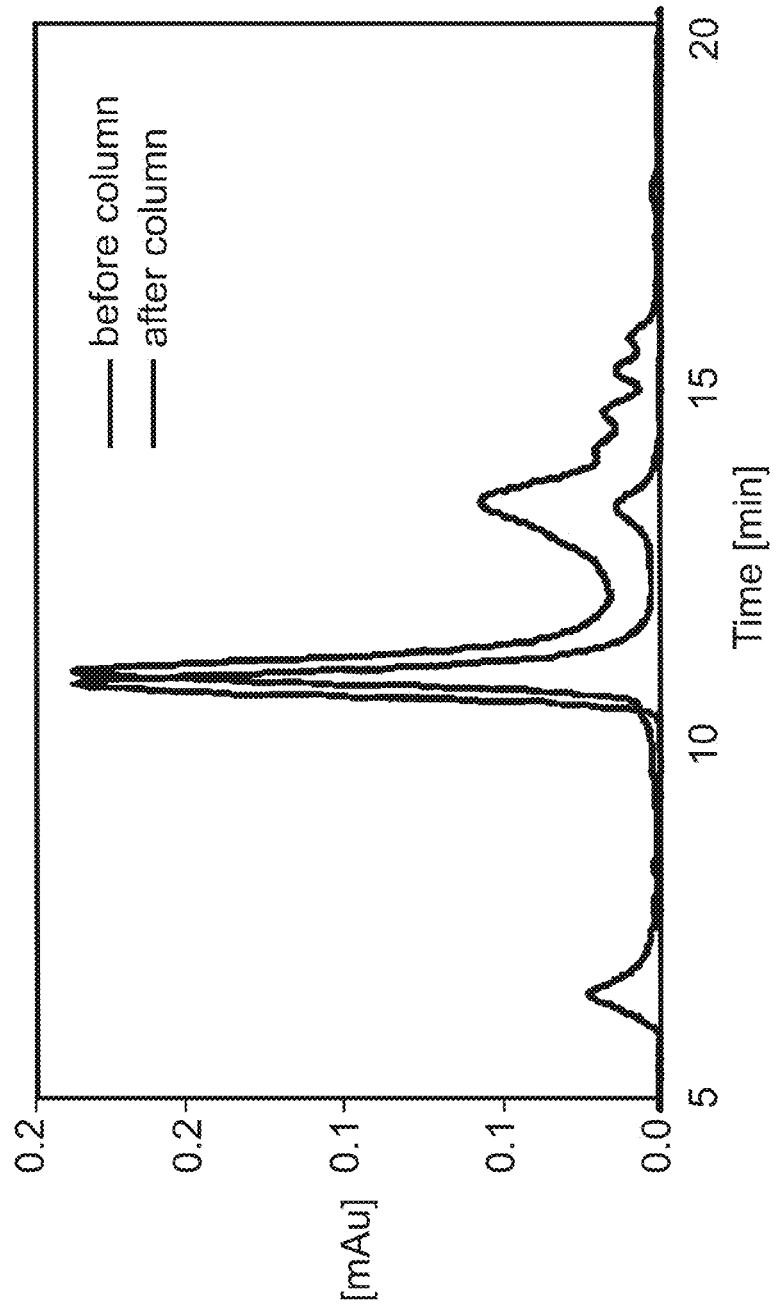
FIG. 2: Chromatograms of the diphtheria toxin solution before and after anion exchange chromatography
Figure 3:
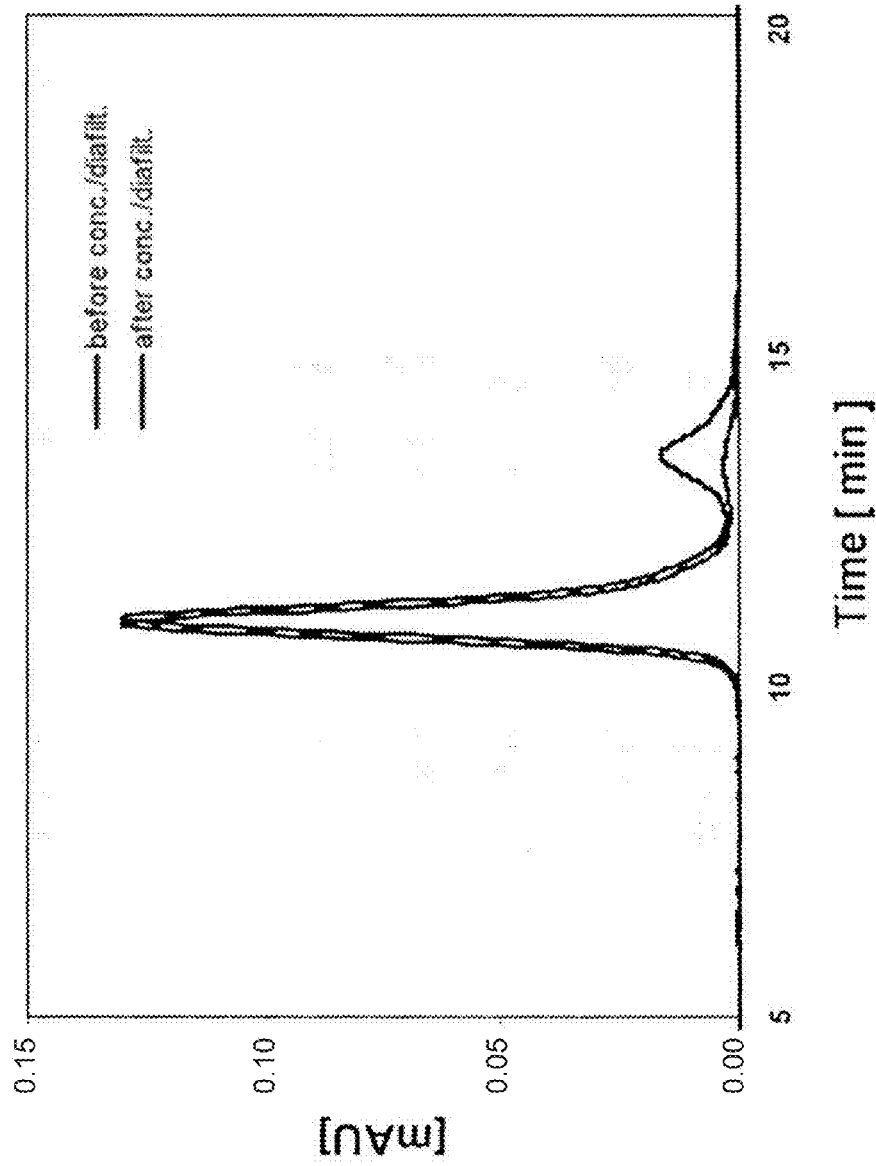
FIG. 3: Chromatograms of the diphtheria toxin solution before and after concentration/diafiltration

PTK yeast extract was purchased from Ohly GmbH (Germany) and deferrated by a process modified from reference 14 as summarized in the following paragraphs.

A solution was prepared by dissolving the commercially available PTK yeast extract in water. The yeast extract solution was then heated to 60° C. and $Na_2HPO_4.2H_2O$ and $KH_2PO_4$ was added. The pH of the solution was adjusted to 9.3 by the addition of sodium hydroxide. The solution was further heated to 79° C., and $CaCl_2$ solution was added. Subsequently, the solution was heated to 85° C. and incubated for 10 min. Afterward the yeast extract solution was allowed to cool to 25° C. over 3 hours.

Any precipitate that had formed was removed by centrifugation. The pH of the deferrated yeast extract solution was adjusted to 8.4 by the addition of acetic acid. The solution was subjected to ultrafiltration and subsequent sterilization in an autoclave for 90 min at 134° C. The final composition of the deferrated yeast extract solution is summarized in Table 1.

TABLE 1

Composition of the deferrated yeast extract solution

| Component | Amount | |
|---|---|---|
| PTK yeast extract | 102.48 | g |
| $Na_2HPO_4 \cdot 2H_2O$ | 5.02 | g |
| $KH_2PO_4$ | 1.33 | g |
| $CaCl_2 \cdot 2H_2O$ | 4.21 | g |
| Sodium hydroxide solution | 31.10 | ml |
| Acetic acid solution (100%) | 13.96 | ml |
| Water | Ad 1000 | ml |

Example 2

Preparation of the Fermentation Medium

In order to prepare the fermentation medium, maltose monohydrate dissolved in water, sodium lactate solution, growth factor solution, water and L-cysteine solution were added to the deferrated yeast extract in the order as listed. In a further step, ammonium Fe(III) citrate solution and phosphate solution (also in the order as listed) were added. The further addition of calcium chloride solution led to the precipitation of the iron and the formation of an iron-containing gel, which slowly releases iron into the fermentation medium during bacterial growth without inhibiting toxin production. In a final step, the pH of the fermentation medium was adjusted to 7.3 by adding 20% acetic acid solution or 10% ammonium solution as needed. The composition of the growth factor solution is provided in Table 2.

TABLE 2

Composition of the growth factor solution

| Component | Amount | |
|---|---|---|
| $MgSO_4 \cdot 7H_2O$ | 225 | g |
| β-alanine | 2.3 | g |
| Pimelic acid | 150 | mg |
| Nicotinic acid | 4.6 | g |
| $CuSO_4 \cdot 5H2O$ | 500 | mg |
| $ZnSO_4 \cdot 7H_2O$ | 500 | mg |
| $MnCl_2 \cdot 4H_2O$ | 240 | mg |
| HCl 25% | 2.6 | ml |
| Water | Ad 1000 | ml |

The final composition of the fermentation medium is shown in Table 3. After all components had been added, the fermentation medium was sterilized in an autoclave for 90 min at 134° C. The autoclaved fermentation medium was filter sterilized and stored at 2° C. to 10° C.

TABLE 3

Components of the fermentation medium

| Component | Amount | |
|---|---|---|
| PTK yeast extract | 34.38 | g |
| $Na_2HPO_4 \cdot 2H_2O$ | 1684.13 | mg |
| $KH_2PO_4$ | 497.48 | mg |
| $CaCl_2 \cdot 2H_2O$ | 2.13 | g |
| Sodium hydroxide solution | 10.43 | ml |
| Acetic acid solution (100%) | 4.69 | ml |
| Maltose monohydrate | 49.68 | g |
| Sodium lactate solution | 2.07 | ml |
| $MgSO_4 \cdot 7H_2O$ | 1.8 | g |
| β-alanine | 18.41 | mg |
| Pimelic acid | 1.20 | mg |

TABLE 3-continued

Components of the fermentation medium

| Component | Amount | |
|---|---|---|
| Nicotinic acid | 36.83 | mg |
| $CuSO_4 \cdot 5H2O$ | 4.00 | mg |
| $ZnSO_4 \cdot 7H_2O$ | 4.00 | mg |
| $MnCl_2 \cdot 4H_2O$ | 1.92 | mg |
| HCl 25% | 0.70 | ml |
| L-cysteine solution | 280.19 | mg |
| Ammonium Fe(III) citrate solution | 3.23 | mg |
| $K_2HPO_4 \cdot 3H_2O$ | 201.48 | mg |
| Water | Ad 1000 | ml |

Example 3

Preparation of Crude Diphtheria Toxin

The fermentation medium was inoculated with *Corynebacterium diphtheriae* from a working seed to prepare a preculture. Both the working seed and the master seed were prepared using the fermentation medium described above.

A fermenter with a total capacity of 300 L was filled with fermentation medium, and the preculture was diluted into the fermentation medium to prepare the main culture. The main culture was incubated at 36° C. at 560 rpm for 20 hours. Thereon after incubation was continued at 620 rpm for an additional 24 hours. The fermentation process yielded diphtheria toxin in a concentration of 200 Lf/ml to 250 Lf/ml.

The culture medium was separated from the bacteria by centrifugation, and the culture supernatant was passed through a filtration cascade starting with a 0.5 nm filter and ending with a 0.2 nm filter. Citrate buffer was then added to the resulting crude diphtheria toxin solution and adjusted to a final concentration of 5 mM of citrate. The solution was concentrated by diafiltration against 5 volumes of 5 mM citrate pH 6.5 using a regenerated cellulose membrane with a 30 kDa cut-off. This reduced the volume from about 300 L to about 50 L. The retained concentrated diphtheria toxin solution was passed through a 0.2 nm filter. The resulting sterile concentrated diphtheria toxin solution was designated "diphtheria toxin concentrate 1" and was stored until further use.

Prior to purification, a buffer exchange was performed. The diphtheria toxin concentrate 1 was diafiltered against 5 volumes of 25 mM tris-buffer pH 7.5 using a regenerated cellulose membrane with a 30 kDa cut-off. The tris-buffered solution was filtered using Z carbon filtration and passed through a 0.2 nm filter. The resulting sterile, tris-buffered diphtheria toxin solution was designated "diphtheria toxin concentrate 2."

A flow chart of the process described in Example 3 is provided in FIG. 1.

Example 4

Purification of the Crude Diphtheria Toxin

To further purify the crude diphtheria toxin produced in the fermentation process described in the preceding example, anion exchange chromatography was applied. 50 L fermenter harvests could reproducibly purified using the method described below.

The diphtheria toxin concentrate was loaded onto a Factogel EMD TMAE anion exchange gel matrix column purchased from Merck Chemicals. The purified diphtheria toxin was eluted with 25 mM tris/90 mM NaCl buffer pH 7.5.80% of the protein loaded on the column could be recovered by a simple elution step with the NaCl buffer. The initial volume of 50 l of crude diphtheria toxin solution was reduced to 10 l purified diphtheria toxin solution. The eluate from the anion exchange column was over 85% pure. A representative chromatogram of the diphtheria toxin solution before loading onto and after elution from the anion exchange TABLE 6-continued HPLC SEC/Retention time of the major peak [min, in bold]

| Lysine concentration | pH 7.0 | | pH 7.5 | | pH 8.0 | | Formalin content |
|---|---|---|---|---|---|---|---|
| 0.05M | 9 | 10 | 29 | 30 | 49 | 50 | 0.50% |
| | | 19.40 | | 19.33 | | 19.40 | |
| | 11 | 12 | 31 | 32 | 51 | 52 | 0.75% |
| | | 19.35 | | 19.27 | | 19.37 | |
| | 13 | 14 | 33 | 34 | 53 | 54 | 1.00% |
| | | 19.13 | | 19.20 | | 19.22 | |
| 0.1M | 15 | 16 | 35 | 36 | 55 | 56 | 0.50% |
| | | 19.72 | | 19.67 | | 19.62 | |
| | 17 | 18 | 37 | 38 | 57 | 58 | 0.75% |
| | | 19.65 | | 19.50 | | 19.58 | |
| | 19 | 20 | 39 | 40 | 59 | 60 | 1.00% |
| | | 19.47 | | 19.37 | | 19.52 | |

TABLE 7

HPLC SEC/Degree of dimerization [%, in bold]

| Lysine concentration | pH 7.0 | | PH 7.5 | | pH 8.0 | | Formalin content |
|---|---|---|---|---|---|---|---|
| 0M | 1 | 2 | 21 | 22 | 41 | 42 | 0.50% |
| | | 12.2 | | 13.6 | | 13.0 | |
| 0.025M | 3 | 4 | 23 | 24 | 43 | 44 | 0.50% |
| | | 9.4 | | 11.0 | | 9.2 | |
| | 5 | 6 | 25 | 26 | 45 | 46 | 0.75% |
| | | 9.8 | | 8.7 | | 7.7 | |
| | 7 | 8 | 27 | 28 | 47 | 48 | 1.00% |
| | | 8.6 | | 7.6 | | 7.9 | |
| 0.05M | 9 | 10 | 29 | 30 | 49 | 50 | 0.50% |
| | | 10.2 | | 11.0 | | 7.2 | |
| | 11 | 12 | 31 | 32 | 51 | 52 | 0.75% |
| | | 9.6 | | 9.2 | | 5.7 | |
| | 13 | 14 | 33 | 34 | 53 | 54 | 1.00% |
| | | 8.9 | | 9.3 | | 4.4 | |
| 0.1M | 15 | 16 | 35 | 36 | 55 | 56 | 0.50% |
| | | 10.7 | | 16.6 | | 9.8 | |
| | 17 | 18 | 37 | 38 | 57 | 58 | 0.75% |
| | | 9.4 | | 13.5 | | 9.4 | |
| | 19 | 20 | 39 | 40 | 59 | 60 | 1.00% |
| | | 9.2 | | 9.5 | | 7.6 | |

The influence of lysine was more pronounced than that of FA, due to the broader variation of this parameter. In the studied range, the pH seemed to have no influence.

Samples devoid of lysine did not behave according to the general trends. They showed longer elution times and higher amounts of dimers, compared to those with 0.025M lysine. In the presence of lysine, FA preferably generates N-hydroxymethylated lysine. This intermediate seems to have a better reactivity with the toxin than FA alone, explaining for the better formylation and the reduced dimerization.

Looking at the samples No. 2, 3, 7, 15 and 47 on a Superdex 200 HR 10/30 column gave the same trends. Formylation worked best with 1% FA 40% and 0.025M lysine.

IEF

Isoelectric focusing (IEF) was employed to evaluate the extent of FA treatment. Since FA reacts with positive charged amino groups, acidic groups become more prominent. As a result, the pI drops.

Figure 4:
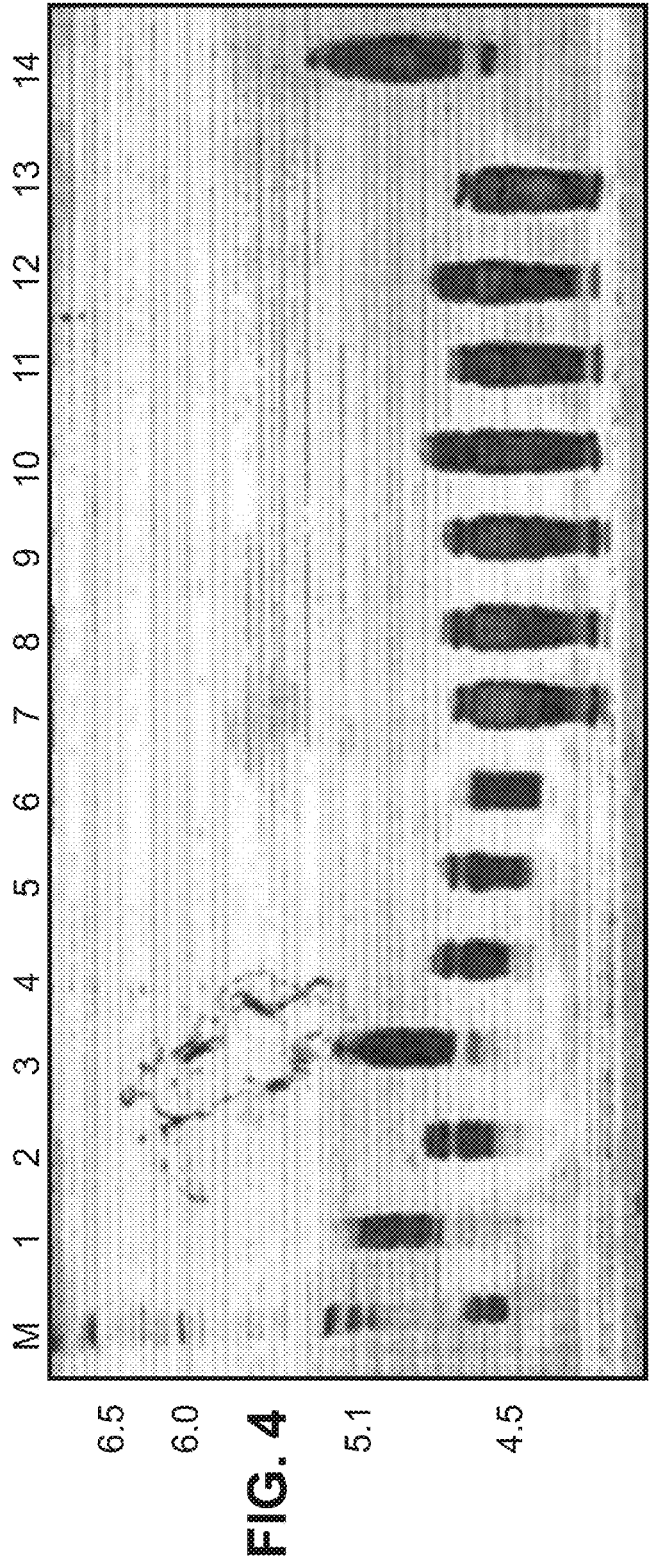
FIG. 4: Electric focusing gel for samples no. 1, 7, 15, 41, 47 and 55 in comparison to samples prepared by a conventional process in which the crude diphtheria toxin is detoxified prior to purification
Figure 5:
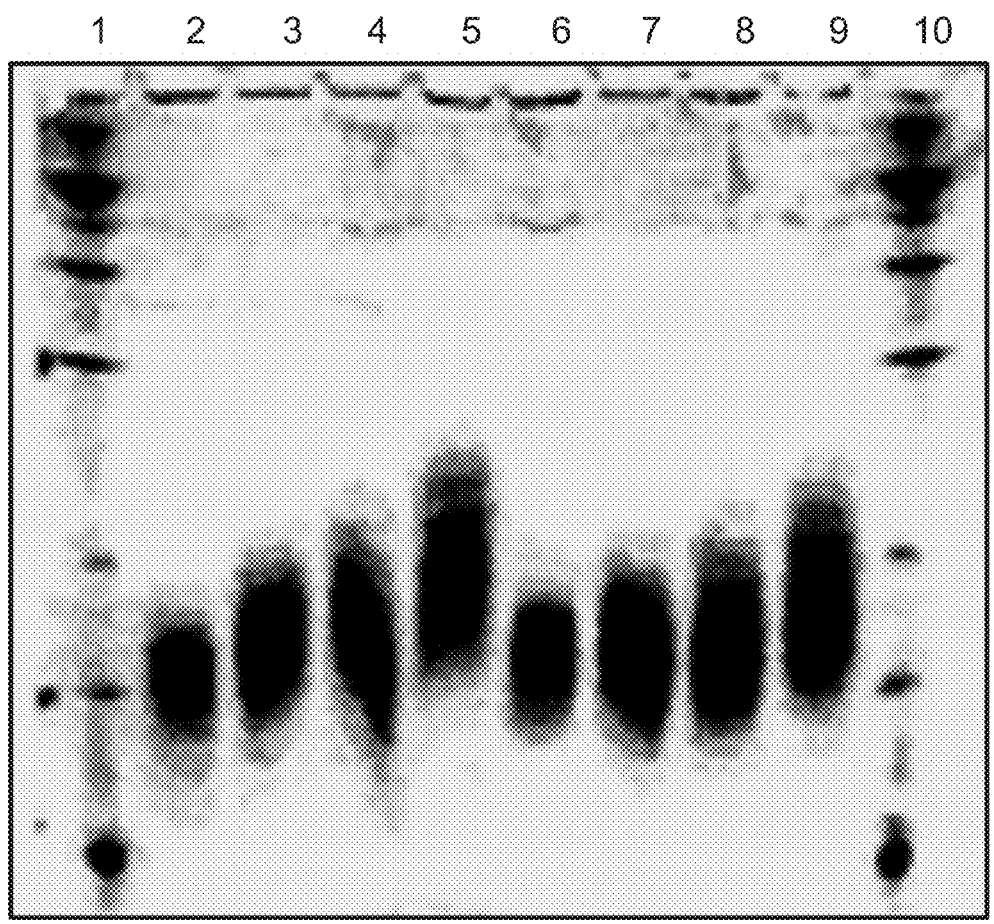
FIG. 5: Electric focusing gel for samples no. 1, 3, 9, 15, 41, 43, 49 and 55
Figure 6:
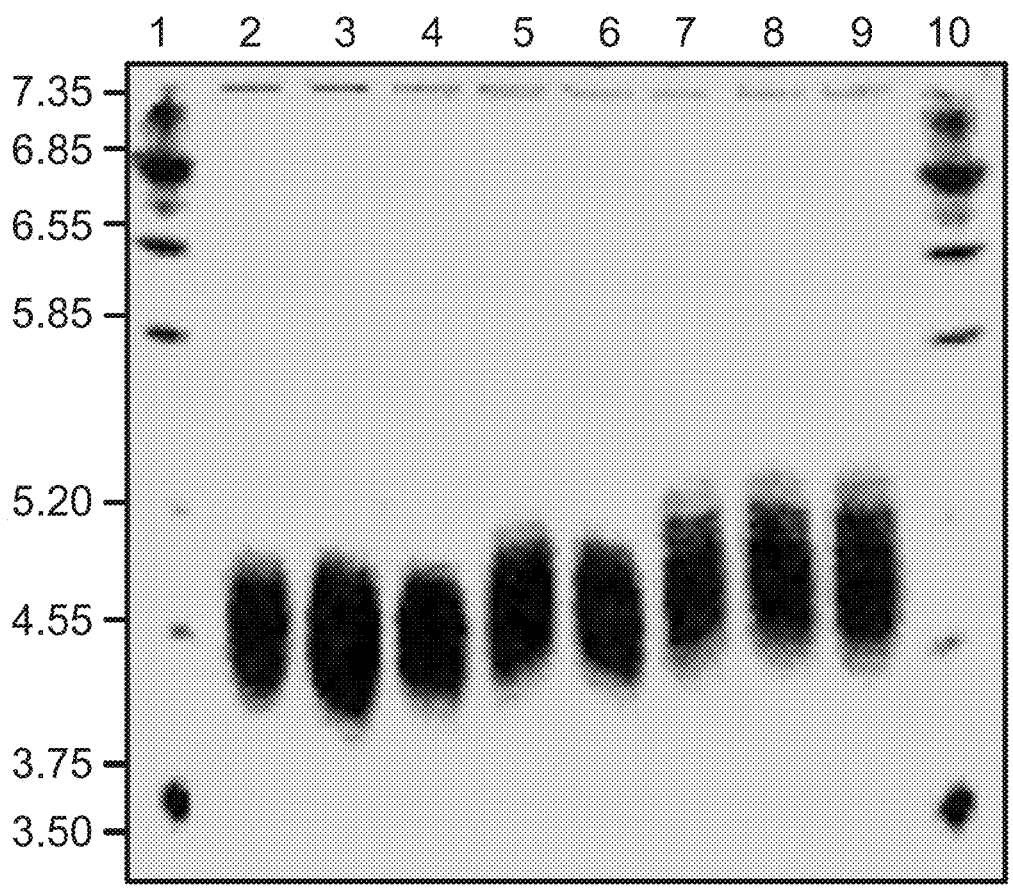
FIG. 6: Electric focusing gel for samples no. 5, 25, 45, 11, 51, 17, 37 and 57
Figure 7:
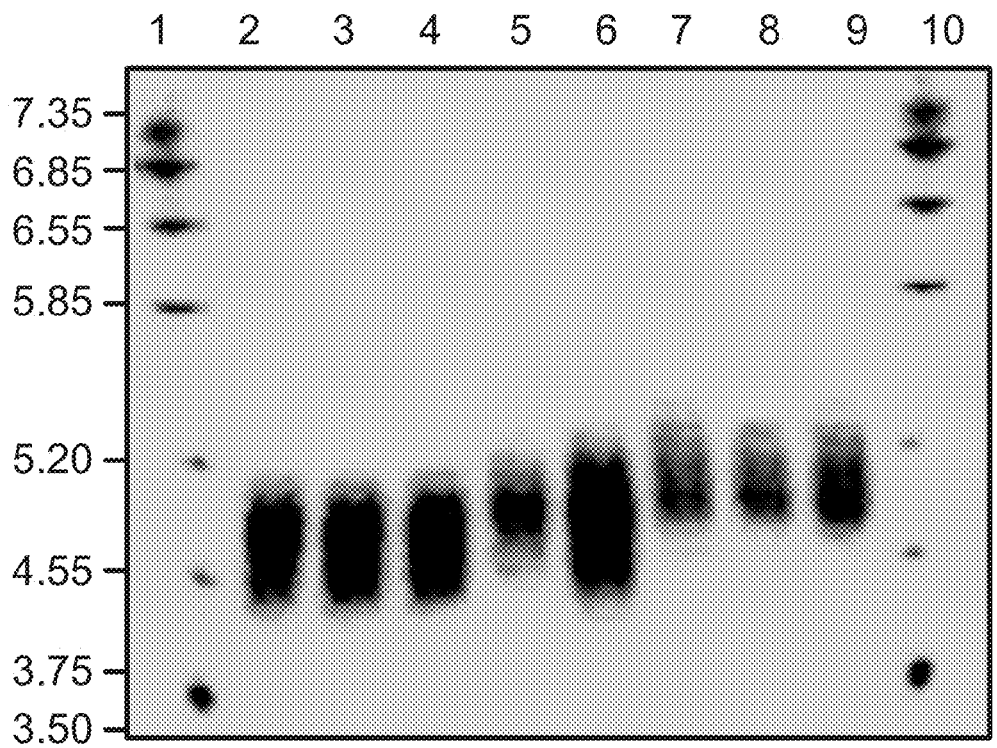
FIG. 7: Electric focusing gel for samples no. 7, 27, 47, 13, 53, 19, 39 and 59
Figure 8:
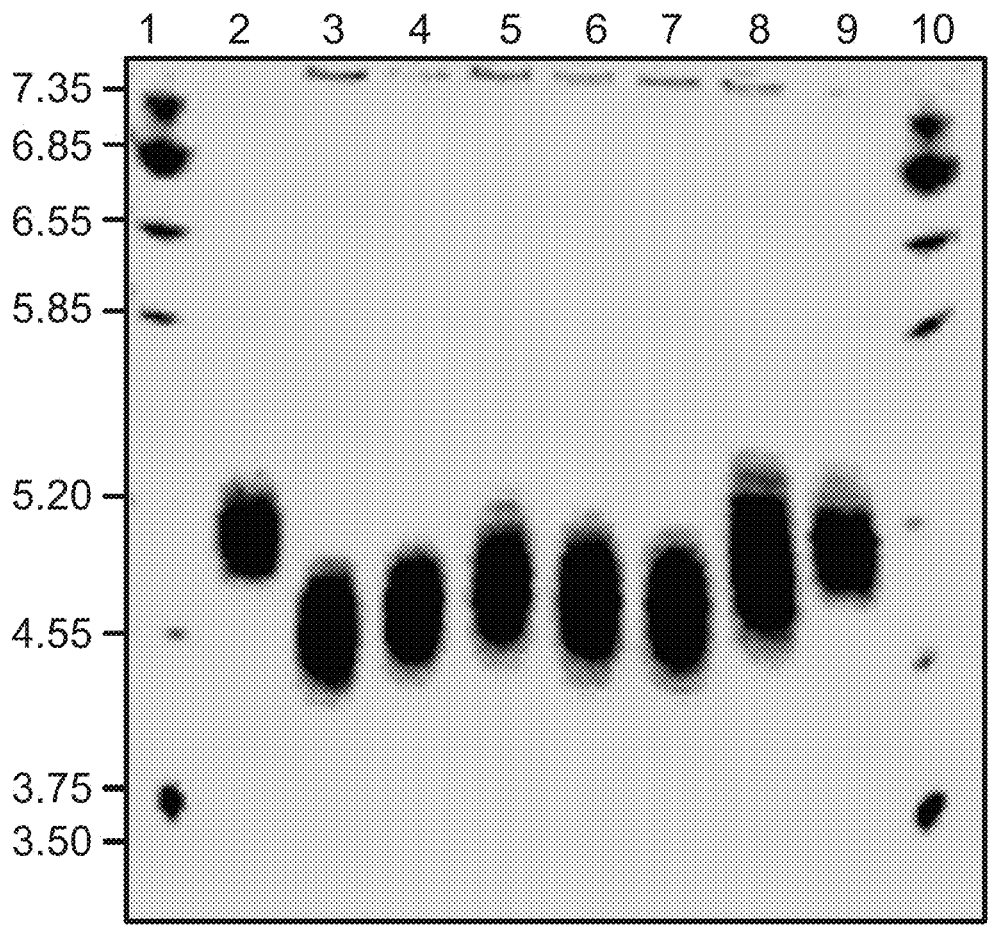
FIG. 8: Electric focusing gel for samples no. 21, 23, 29, 31, 33 and 35 in comparison to toxin prior to detoxification buffered at pH7 (lane 2) or pH 8 (lane 9)

Selected samples No. 1, 7, 15, 41, 47 and 55 were tested (see FIG. 4). Since a fairly big difference in their chromatographic behaviour became obvious, all 30 samples were studied for their pI (see FIG. 5-8). The results of these studies are summarized in Table 8.

TABLE 8 pI range of various diphtheria toxoids

| Sample description | pI range |
|---|---|
| Toxoids from conventional production | 4.8-3.5 |
| New detoxification, without lysine | 4.8-4.0 |
| New detoxification, with 0.025M lysine | 5.0-4.1 |
| New detoxification, with 0.05M lysine | 5.2-4.3 |
| New detoxification, with 0.1M lysine | 5.4-4.4 |
| CRM, failing the potency test | 5.4-4.6 |

In agreement with theoretical considerations, the more FA treatment was applied (as achieved by high FA concentrations and low lysine concentrations), the lower was the pI.

TABLE 10

Results of the turbidity test after dialysis

| Sample No. | Theoretical Value [Lf/mL] | 14 days [Lf/mL] | 28 days [Lf/mL] | 42 days [Lf/mL] |
|---|---|---|---|---|
| 1 | 500 | 216 | 276 | 244 |
| 2 | 2000 | 1454 | 1354 | 1196 |
| 3 | 5000 | 4493 | 3014 | 3058 |
| 4 | 500 | 492 | 478 | 374 |
| 5 | 1000 | 1097 | 1066 | 946 |
| 6 | 2000 | 2236 | 2016 | 2035 |
| 7 | 3000 | 3089 | 3170 | 2860 |
| 8 | 5000 | 5158 | 5980 | 5736 |
| 9 | 2000 | 2080 | 1939 | 2285 |
| 10 | 2000 | 2028 | 2184 | 2215 |
| 11 | 2000 | 1830 | 1716 | 1716 |
| 12 | 2000 | 2010 | 1792 | 1980 |

The samples that had been detoxified with formaldehyde and lysine showed no loss of activity (Lf/mL) even after 42 days. Samples without lysine showed lower Lf/mL values than comparable samples with lysine. The biggest decrease in activity was seen after 14 days. After 28 and 42 days the activity decreased only slightly.

All samples were tested for residual toxicity in the Vero cell assay described above and were compared with purified toxin and a standard. The samples gave $ED_{50}$ values between 100 and 300 Lf/mL which are $10^5$-$10^6$ times higher than the values for the toxins. Diphtheria toxoid produced by existing processes give values between 50-500 Lf/mL. No time dependency of the detoxification process was observed. It seems that detoxification was complete after 14 days. The results of the Vero cell assay for samples 1-12 are summarized in Table 11.

TABLE 11

Results of the toxicity assay using Vero cells

| | 14 days 50% value [Lf/mL] | 28 days 50% value [Lf/mL] | 42 days 50% value [Lf/mL] |
|---|---|---|---|
| 1 | 167.20 | 146.74 | 238.44 |
| 2 | 187.19 | 192.86 | 174.16 |
| 3 | 391.50 | 176.66 | 260.2 |
| 4 | 138.66 | 122.95 | 135.03 |
| 5 | 203.20 | 165.04 | 200.06 |
| 6 | 206.27 | 140.82 | 241.65 |
| 7 | 231.74 | 200.30 | 259.97 |
| 8 | 217.26 | 196.18 | 308.04 |
| 9 | 149.81 | 184.65 | 306.23 |
| 10 | 128.67 | 167.13 | 231.52 |
| 11 | 164.14 | 151.70 | 239.53 |
| 12 | 116.40 | 128.29 | 190.53 |
| Standard | 0.00031 | 0.00017 | 0.00071 |
| Standard | 0.00045 | 0.00162 | 0.00041 |
| Toxin | 0.00055 | 0.00665 | 0.01234 |
| Toxin | 0.00168 | 0.00682 | 0.00046 |

This finding is also supported by the results obtained after determination of free formaldehyde. After 14 days of detoxification all samples showed a lower free formaldehyde concentration compared to the initial concentration, but no further formaldehyde was consumed over the following 30 days. The results of the assay for determining the free formaldehyde concentration of samples 1-12 before dialysis are summarized in Table 12.

TABLE 12

Free formaldehyde concentration

| | Theoretical Starting Value | 14 days [g/l] | 28 days [g/l] | 42 days [g/l] |
|---|---|---|---|---|
| 1 | 3.8 | 3.6 | 3.0 | 3.6 |
| 2 | 3.8 | 3.5 | 2.9 | 3.4 |
| 3 | 3.8 | 3.2 | 2.7 | 3.3 |
| 4 | 3.8 | 2.4 | 1.9 | 2.0 |
| 5 | 3.8 | 2.3 | 1.9 | 1.9 |
| 6 | 3.8 | 2.2 | 1.9 | 1.9 |
| 7 | 3.8 | 2.4 | 1.8 | 1.8 |
| 8 | 3.8 | 2.0 | 1.6 | 1.7 |
| 9 | 7.6 | 4.8 | 4.2 | 4.4 |
| 10 | 7.6 | 3.2 | 3.1 | 2.6 |
| 11 | 15.2 | 11.9 | 10.7 | 11.7 |
| 12 | 15.2 | 7.3 | 6.2 | 6.3 |

Analysis of the samples by SEC also showed no further reaction after 14 days detoxification (see FIG. 9-11). The SEC analysis clearly uncovered the influence of higher toxin concentrations during detoxification in the presence and the absence of lysine. The higher the toxin concentration was, the higher was the fraction of dimers and multimers (see FIG. 9-11). Dimer and multimer formation was observed in the presence and absence of lysine. However, lysine significantly inhibited the cross-linking reaction resulting in the formation of far less dimers than in its absence (33% dimers in absence of lysine vs. 10% in the presence of 0.025 mM lysine at 2000 Lf/ml; see Table 11, samples 2 and 6). The percentage of dimers in each of samples 1-12 is shown in Table 13.

TABLE 13

Percentage of dimers

| | 14 days Dimer [%] | 28 days Dimer [%] | 42 days Dimer [%] |
|---|---|---|---|
| 1 | 9 | 10 | 12 |
| 2 | 28 | 32 | 33 |
| 3 | 51 | 56 | 58 |
| 4 | 2 | 2 | 2 |
| 5 | 5 | 5 | 5 |
| 6 | 10 | 10 | 10 |
| 7 | 14 | 14 | 15 |
| 8 | 23 | 23 | 24 |
| 9 | 9 | 9 | 10 |
| 10 | 9 | 8 | 8 |
| 11 | 9 | 10 | 10 |
| 12 | 9 | 9 | 9 |

Connecting a light scattering detector with the SEC to look at the molecular weight of the separated peaks confirmed that the major peak was the monomer with a molecular weight of ca. 60 kDa. The minor peaks were dimers with 120 kDa, and in some samples, trimers with 180 kDa or even multimers could be detected.

Example 6

Potency of the Diphtheria Toxoid Prepared by the New Processes

Potency studies were carried out in accordance with the requirements of the European Pharmacopoeia (1997, third edition, Council of Europe, Strasbourg, France, Assay of diphtheria vaccine (adsorbed), pp. 113-115).

The crude diphtheria toxin was prepared as described in the preceding examples. To further purify and detoxify the crude diphtheria toxin, the purification process described in Example 4 was combined with the optimized detoxification process described in Example 5 resulting in the combined process shown in FIG. 12.

The diphtheria toxin was purified by anion exchange chromatography as described above. The toxin concentration of the eluate was adjusted to 5000 Lf/mL. The concentrated diphtheria toxin solution was detoxified in phosphate buffer pH 7.5 by addition of FA (40% solution) to a final concentration of 1% in the presence of 0.025M lysine (final concentration) as described in Example 5. The resulting diphtheria toxoid was diluted and subsequently adsorbed to aluminium hydroxide. The composition of the final vaccine formulations are shown in Table 14.

Potency of the vaccine formulations was tested in guinea pigs. Pediatric vaccines pass the potency test when the lower confidential limit is at least 30 IU/dose. The results of the potency studies are summarized in Table 14.

TABLE 14

Composition of the vaccine formulations and potency test data

| Sample | Diphtheria toxin [Lf/mL] | Tetanus toxin [Lf/mL] | IPV | $Al(OH)_3$ [mg/mL] | Osmolality [mosm/kg] | pH | Potency [IU/dose] |
|---|---|---|---|---|---|---|---|
| D vaccine (paediatric) | 50 | — | — | 3.24 | 266 | 6.20 | 39 pass |
| D vaccine (paediatric) | 50 | — | — | 3.15 | 267 | 6.40 | 48 pass |
| D vaccine (paediatric) | 50 | — | — | 3.15 | 267 | 6.40 | 35 pass |
| Td-IPV (adult) | 4 | 10 | 80/16/64 | 1.95 | 290 | 6.86 | 5 pass |
| Dt vaccine (paediatric) | 34 | 20 | — | 3.28 | 271 | 6.37 | 33 pass |
| DT concentrate* | 167 | 67 | — | 7.36 | 314 | 6.30 | 39 pass |

*for the potency test, the concentrate was diluted to 50 Lf/mL of diphtheria toxin and 30 Lf/mL of tetanus toxin

Example 7

Analysis of Diphtheria Toxoid Composition

A composition comprising diphtheria toxoid prepared according to the process outline in FIG. 12 was stored at +2-8° C. for 0, 6 and 12 months. No preservatives were added to the composition during the entire production process. After each time point, aliquots of the sample were used for potency testing, purity analysis, flocculation assay, HPLC analytics, pH measurement, toxicity and sterility testing and chemical analysis of free lysine, formaldehyde, sodium chloride, sulphate and phosphate content. Potency and toxicity was tested in guinea pigs. The results are summarized in Table 15.

At all time points, the composition widely exceeded purity requirements and potency requirements. Likewise, the residual formaldehyde concentration was below the allowable limit of 0.2 mg/ml.

TABLE 15

Stability data and Composition

| Test Items | Requirements | Storage Period (months) 0 | 6 | 12 |
|---|---|---|---|---|
| Potency Diphtheria *e.p. (I.U/ml) | 1.1. >= 2.0 | 10 | 10 | |
| 1.1-u.1 | | 6-15 | 8-14 | |
| Nitrogen Antigenic Purity (Lf/mg N) | >=1500 | 2710 | 2740 | 2128 |
| Nitrogen Antigenic Purity (Lf/mg N)/ new method | >=1500 | 2865 | 2825 | 2279 |
| Lf content (Lf) | — | 10000 | 10000 | 8000 |
| Nitrogen first test (mg/ml) | Calculation from Lf/mgN and Lf | 3.69 | 3.65 | 3.76 |
| Nitrogen second test (mg/ml)/new method | Calculation from Lf/mgN and Lf | 3.49 | 3.54 | 3.51 |
| Lysin content (nmol/ml) | <=550 | 555 | n.t | 876 |
| HPLC analytic | — | Meets spec | Meets spec | Meets spec |
| pH | 7.2-7.8 | 7.54 | 7.7 | 7.7 |
| Sodium chloride (mg/ml) | 8-9 | 7.94 | 8.0 | 7.95 |

TABLE 15-continued Stability data and Composition

| Test Items | Requirements | Storage Period (months) | | |
|---|---|---|---|---|
| | | 0 | 6 | 12 |
| Formaldehyde (mg/ml) | <=0.2 | 0.100 | 0.143 | 0.163 |
| Phosphat (µg/ml) | <=15 | <=0.10 | 0.10 | <=0.10 |
| Sulfat | Not detectable | Meets spec | Meets spec | Meets spec |
| Abnormal toxicity negative test | Acc. to Ph. Eur | Meets spec | Meets spec | Meets spec |
| Toxicity (survivals of 5) | 5 (no toxicity) | 5 | 5 | 5 |
| Sterility test | Acc. to Ph. Eur | Meets spec | Meets spec | Meets spec | e.p. = estimated potency
n.t. = not tested
meets spec = meets specification
l.l. = lower limit-upper limit
*= Potency is determined as a pre-vaccine composition like an adsorbed diphtheria vaccine for adults It will be understood that the invention has been described by way of example only and modifications may be made whilst remaining within the scope and spirit of the invention.

REFERENCES

[1] *Vaccines*. (eds. Plotkin & Orenstein). 4th edition, 2004, ISBN: 0-7216-9688-0.
[2] *New Generation Vaccines* (eds. Levine et al.) 2nd edition, 1997. ISBN: 0-8247-0061-9.
[3] Kattan et al. (May 2011), *J. Allergy. Clin. Immunol.* 128(1):215-218
[4] Orhan & Sekerel (2003), *Allergy* 58(2):127-131
[5] European patent 1849860
[6] WO2005/056773
[7] WO2006/042542
[8] WO00/50449
[9] UK Patent Application GB-969772
[10] Frech et al. (2000) *Dev. Biol. Basel, Karger* 103:205-215
[11] Metz et al. (2003) *Vaccine* 22:156-167
[12] U.S. Pat. No. 3,889,006
[13] EP-A-2228437
[14] Stainer & Scholte (1973) *Biotechnol. Bioeng. Symp.* 4:283-293
[15] Holmes (2000) *J. Infect. Dis.* 181 Suppl 1:S156-67
[16] Anonymous (January 2002) *Research Disclosure,* 453077.
[17] Giannini et al. (1984) *Nucl Acids Res* 12:4063-9.
[18] WO2011/138682
[19] WO 2007/052163
[20] NIBSC code: TEFT.
[21] Sesardic et al. (2002) *Biologicals* 30:49-68.
[22] NIBSC code: 98/552.
[23] Rappuoli et al. (1991) *TIBTECH* 9:232-238.
[24] NIBSC code: 66/303.
[25] Ramsay et al. (2001) *Lancet* 357(9251):195-196.
[26] Lindberg (1999) *Vaccine* 17 Suppl 2:S28-36.
[27] Buttery & Moxon (2000) *J R Coll Physicians Lond* 34:163-168.
[28] Ahmad & Chapnick (1999) *Infect Dis Clin North Am* 13:113-133, vii.
[29] Goldblatt (1998) *J. Med. Microbiol.* 47:563-567.
[30] European patent 0 477 508.
[31] U.S. Pat. No. 5,306,492.
[32] WO98/42721.
[33] *Conjugate Vaccines* (eds. Cruse et al.) ISBN 3805549326, particularly vol. 10:48-114.
[34] Hermanson (1996) *Bioconjugate Techniques* ISBN: 0123423368 or 012342335X.
[35] WO96/40242.
[36] Giuliani et al. (2006) *PNAS USA* 103:10834-9.
[37] *W.H.O. Tech. Rep. Ser.* 594:51, 1976.
[38] Zielen et al. (2000) *Infect. Immun.* 68:1435-1440.
[39] Darkes & Plosker (2002) *Paediatr Drugs* 4:609-630.
[40] Watson (2000) *Pediatr Infect Dis J* 19:331-332.
[41] Rubin (2000) *Pediatr Clin North Am* 47:269-285, v.
[42] Jedrzejas (2001) *Microbiol Mol Biol Rev* 65:187-207.
[43] Vanlandschoot et al. (2005) *J Gen Virol* 86:323-31.
[44] WO2007/054820.
[45] WO03/066094.
[46] Module 6 of WHO's *The immunological basis for immunization series* (Robertson)
[47] WO2008/028956.
[48] WO2008/028957.
[49] Anderson (1983) *Infect Immun* 39(1):233-238.
[50] Anderson et al. (1985) *J Clin Invest* 76(1):52-59.
[51] EP-A-0372501.
[52] EP-A-0378881.
[53] EP-A-0427347.
[54] WO93/17712
[55] WO94/03208.
[56] WO98/58668.
[57] EP-A-0471177.
[58] WO91/01146
[59] Falugi et al. (2001) *Eur J Immunol* 31:3816-24.
[60] Baraldo et al. (2004) *Infect Immun* 72:4884-87.
[61] EP-A-0594610.
[62] WO00/56360.
[63] WO02/091998.
[64] Kuo et al. (1995) *Infect Immun* 63:2706-13.
[65] WO01/72337
[66] WO00/61761.
[67] WO04/041157.
[68] *Vaccine Design: The Subunit and Adjuvant Approach* (eds. Powell & Newman) Plenum Press 1995 (ISBN 0-306-44867-X).
[69] WO97/00697.
[70] WO02/00249.
[71] U.S. Pat. No. 6,013,264.
[72] U.S. Pat. No. 4,624,918.
[73] Nony et al. (2001) *Vaccine* 27:3645-51.

[74] Module 1 of WHO's *The immunological basis for immunization series* (Galazka).
[75] Lyng (1990) *Biologicals* 18:11-17.
[76] NIBSC code: 69/017.
[77] NIBSC code: DIFT.
[78] Kuhmlann & Rieger (1995) *Immunol Infect Dis* 5:10-4.
[79] Sesardic et al. (2001) *Biologicals* 29:107-22.
[80] NIBSC code: 98/560.

The invention claimed is:

1. A composition suitable for human vaccination, comprising a formaldehyde-linked diphtheria toxoid which is free from formaldehyde-linked animal-derived components, wherein the diphtheria toxoid was inactivated by formaldehyde crosslinking of diphtheria toxin that was at least 90% pure during detoxification, and wherein the diphtheria toxoid has (i) a specific purity of at least 1500 Lf/mg diphtheria toxin protein nitrogen during detoxification, and (ii) a potency of at least 60 IU/ml.

2. The composition of claim 1, wherein the monomer:dimer ratio of the diphtheria toxoid in the range of 3:1 to 8:1.

3. The composition of claim 1 or 2, comprising a protective antigen from at least one pathogen other than *Corynebacterium diphtheriae*.

4. The composition of claim 3, wherein the non-diphtheria protective antigen is selected from hepatitis B virus surface antigen (HBsAg), tetanus toxoid (T), a pertussis antigen, a conjugated *Haemophilus influenzae* type B capsular saccharide (Hib), a conjugated *Neisseria meningitidis* capsular saccharide, a conjugated *Streptococcus pneumoniae* capsular saccharide, and/or an inactivated poliovirus.

5. The composition of claim 4, wherein the HBsAg is free from animal-derived components.

6. The composition of claims 4, wherein the composition is composed of:
   the formaldehyde-linked diphtheria toxoid (D), T, HBsAg;
   D, T, a cellular Pertussis antigen or a whole cell Pertussis antigen (Pw), HBsAg;
   D, T, Pw, HBsAg, Hib;
   D, T, Pw, HBsAg, Hib, an *N. meningitidis* serogroup A capsular saccharide (MenA), an *N. meningitidis* serogroup C capsular saccharide (MenC);
   D, T, Pw, HBsAg, Hib, MenA, MenC, an *N. meningitidis* serogroup W135 capsular saccharide (MenW135);
   D, T, Pw, HBsAg, Hib, MenA, MenC, an *N. meningitidis* serogroup Y capsular saccharide (MenY);
   D, T, Pw, HBsAg, Hib, MenA, MenC, MenW135, MenY;
   D, T, an acellular Pertussis antigen (Pa), HBsAg;
   D, T, Pa, HBsAg, Hib;
   D, T, Pa, HBsAg, poliovirus;
   D, T, Pa, HBsAg, poliovirus, Hib;
   D, T, Pa, HBsAg, poliovirus, Hib, MenC;
   D, T, Pa, HBsAg, poliovirus, Hib, MenC, MenA;
   D, T, Pa, HBsAg, poliovirus, Hib, MenC, MenY;
   D, T, Pa, HBsAg, poliovirus, Hib, MenC, MenW135; or
   D, T, Pa, HBsAg, poliovirus, Hib, MenC, MenA, MenW135, MenY.

7. A composition suitable for human vaccination, comprising (i) a formaldehyde-linked diphtheria toxoid which is free from formaldehyde-linked animal-derived components, wherein the diphtheria toxoid was inactivated by formaldehyde crosslinking of diphtheria toxin that was at least 90% pure during detoxification, and (ii) a protective antigen from at least one pathogen other than *Corynebacterium diphtheriae*, wherein the diphtheria toxoid has (a) a specific purity of at least 1500 Lf/mg diphtheria toxin protein nitrogen, and (b) a potency of at least 60 IU/ml.

8. The composition of claim 7, wherein the non-diphtheria protective antigen is selected from hepatitis B virus surface antigen, tetanus toxoid, a pertussis antigen, a conjugated *H. influenzae* type B capsular saccharide, a conjugated *N. meningitidis* capsular saccharide, a conjugated *S. pneumoniae* capsular saccharide, and/or an inactivated poliovirus.

9. The composition of claim 8, wherein the HBsAg is free from animal-derived components.

10. The composition of claims 8, wherein the composition is composed of:
    D, T, HBsAg;
    D, T, Pw, HBsAg;
    D, T, Pw, HBsAg, Hib;
    D, T, Pw, HBsAg, Hib, MenA, MenC;
    D, T, Pw, HBsAg, Hib, MenA, MenC, MenW135;
    D, T, Pw, HBsAg, Hib, MenA, MenC, MenY;
    D, T, Pw, HBsAg, Hib, MenA, MenC, MenW135, MenY;
    D, T, Pa, HBsAg;
    D, T, Pa, HBsAg, Hib;
    D, T, Pa, HBsAg, poliovirus;
    D, T, Pa, HBsAg, poliovirus, Hib;
    D, T, Pa, HBsAg, poliovirus, Hib, MenC;
    D, T, Pa, HBsAg, poliovirus, Hib, MenC, MenA;
    D, T, Pa, HBsAg, poliovirus, Hib, MenC, MenY;
    D, T, Pa, HBsAg, poliovirus, Hib, MenC, MenW135; or
    D, T, Pa, HBsAg, poliovirus, Hib, MenC, MenA, MenW135, MenY.

11. A diphtheria toxoid obtainable by a process comprising:
    (i) growing a culture of a strain of *Corynebacterium diphtheriae* expressing a diphtheria toxin in a fermentation medium free of animal-derived components;
    (ii) purifying the diphtheria toxin from the fermentation medium to obtain a diphtheria toxin solution that was at least 90% pure;
    (iii) adjusting the concentration of diphtheria toxin in the diphtheria toxin solution to at least 3000 Lf/mL to obtain a concentrated solution;
    (iv) adding to the concentrated solution (a) an amino acid at a final concentration of no more than 0.025 M and (b) formaldehyde at a final concentration in the range of 0.75-1% to obtain a detoxification solution; and
    (v) incubating the detoxification solution to obtain the diphtheria toxoid.

12. A composition suitable for human vaccination, comprising the diphtheria toxoid of claim 11.

13. A diphtheria toxoid for use in human vaccination, obtained by a process comprising:
    (i) growing a strain of *Corynebacterium diphtheriae* expressing a diphtheria toxin or a derivative thereof in at least 100 L of a fermentation medium that is free from animal-derived components, optionally wherein the fermentation medium comprises yeast extract;
    (ii) purifying the diphtheria toxin or derivative from the fermentation medium to obtain a purified diphtheria toxin or derivative, wherein the purified toxin or derivative is at least 90% pure;
    (iii) adding formaldehyde to the purified diphtheria toxin or derivative; and
    (iv) incubating the purified diphtheria toxin or derivative from step (iii) to obtain the diphtheria toxoid,
wherein the diphtheria toxoid is cross-linked by formaldehyde to at least one component of the fermentation medium.

14. A diphtheria toxoid for use in human vaccination, obtained by a process comprising:
  (i) growing a culture of a strain of *Corynebacterium diphtheriae* expressing a diphtheria toxin in a fermentation medium free of animal-derived components;
  (ii) purifying the diphtheria toxin from the fermentation medium to obtain a diphtheria toxin solution that was at least 90% pure;
  (iii) adjusting the concentration of diphtheria toxin in the diphtheria toxin solution to at least 2000 Lf/mL to obtain a concentrated solution;
  (iv) adding to the concentrated solution (a) an amino acid at a final concentration of no more than 0.025 M and (b) formaldehyde at a final concentration in the range of 0.75-1% to obtain a detoxification solution; and
  (v) incubating the detoxification solution to obtain the diphtheria toxoid,
wherein the diphtheria toxoid is cross-linked by formaldehyde to at least one component of the fermentation medium.

15. A diphtheria toxoid obtainable by a process comprising:
  (i) growing a strain of *Corynebacterium diphtheriae* expressing a diphtheria toxin or a derivative thereof in at least 100 L of a fermentation medium that is free from animal-derived components, optionally wherein the fermentation medium comprises yeast extract;
  (ii) purifying the diphtheria toxin or derivative from the fermentation medium to obtain a purified diphtheria toxin or derivative, wherein the purified toxin or derivative is at least 90% pure;
  (iii) adding formaldehyde to the purified diphtheria toxin or derivative; and
  (iv) incubating the purified diphtheria toxin or derivative from step (iii) to obtain the diphtheria toxoid.

16. The composition of claim 1, wherein the diphtheria toxoid has an isoelectric point in the range of 4.0 to 5.0.

17. The composition of claim 1, wherein at least 70% of the diphtheria toxoid is in monomeric form.

18. The composition of claim 1, wherein the formaldehyde-linked diphtheria toxoid is not conjugated to a saccharide as a carrier protein.

19. The composition of claim 7, wherein the formaldehyde-linked diphtheria toxoid is not conjugated to a saccharide as a carrier protein.

20. The diphtheria toxoid of claim 11, wherein the diphtheria toxoid is not conjugated to a saccharide as a carrier protein.

21. The diphtheria toxoid of claim 13, wherein the diphtheria toxoid is not conjugated to a saccharide as a carrier protein.

22. The diphtheria toxoid of claim 15, wherein the diphtheria toxoid is not conjugated to a saccharide as a carrier protein.

23. The diphtheria toxoid of claim 15, wherein the diphtheria toxoid is not conjugated to a saccharide.

* * * * *